United States Patent
Greenhalgh

(10) Patent No.: US 10,940,014 B2
(45) Date of Patent: *Mar. 9, 2021

(54) FIXATION DEVICE AND METHOD

(71) Applicant: Stout Medical Group, L.P., Quakertown, PA (US)

(72) Inventor: E. Skott Greenhalgh, Gladwyne, PA (US)

(73) Assignee: Stout Medical Group, L.P., Warrington, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/384,767

(22) Filed: Apr. 15, 2019

(65) Prior Publication Data

US 2019/0240043 A1 Aug. 8, 2019

Related U.S. Application Data

(63) Continuation of application No. 15/975,631, filed on May 9, 2018, now abandoned, which is a continuation
(Continued)

(51) Int. Cl.
*A61F 2/44* (2006.01)
*A61B 17/70* (2006.01)
(Continued)

(52) U.S. Cl.
CPC ........ *A61F 2/4425* (2013.01); *A61B 17/7064* (2013.01); *A61F 2/4405* (2013.01); *A61F 2/4455* (2013.01); *A61F 2/4611* (2013.01); *A61F 2002/305* (2013.01); *A61F 2002/3008* (2013.01); *A61F 2002/30062* (2013.01); *A61F 2002/30387* (2013.01); *A61F 2002/30471* (2013.01); *A61F 2002/30492* (2013.01); *A61F 2002/30515* (2013.01); *A61F 2002/30522* (2013.01); *A61F 2002/30538* (2013.01);
(Continued)

(58) Field of Classification Search
CPC .................................. A61F 2/44–447
See application file for complete search history.

(56) References Cited

U.S. PATENT DOCUMENTS

| 646,119 A | 3/1900 | Clamer et al. |
| 4,204,531 A | 5/1980 | Aginsky |

(Continued)

FOREIGN PATENT DOCUMENTS

| DE | 19710392 | 7/1999 |
| EP | 0734702 | 10/1996 |

(Continued)

OTHER PUBLICATIONS

Choi, G. et al., "Percutaneous Endoscopic Lumbar Discemtomy by Transiliac Approach," *Spine*, 34(12):E443-446, May 20, 2009.
(Continued)

*Primary Examiner* — Nicholas J Plionis
(74) *Attorney, Agent, or Firm* — Levine Bagade Han LLP

(57) ABSTRACT

An implantable orthopedic stability device is disclosed. The device can have a contracted and an expanded configuration. A method of using the device between adjacent facet surfaces for support and/or fixation of either or both of the adjacent vertebrae is also disclosed.

20 Claims, 55 Drawing Sheets

Related U.S. Application Data of application No. 15/202,405, filed on Jul. 5, 2016, now abandoned, which is a continuation of application No. 12/617,663, filed on Nov. 12, 2009, now Pat. No. 9,408,708.

(60) Provisional application No. 61/113,691, filed on Nov. 12, 2008.

(51) Int. Cl.
 *A61F 2/46* (2006.01)
 *A61F 2/30* (2006.01)

(52) U.S. Cl.
 CPC .............. *A61F 2002/30579* (2013.01); *A61F 2002/30594* (2013.01); *A61F 2002/30841* (2013.01); *A61F 2002/4627* (2013.01); *A61F 2002/4677* (2013.01); *A61F 2210/0004* (2013.01); *A61F 2220/0025* (2013.01); *A61F 2220/0091* (2013.01); *A61F 2230/0086* (2013.01); *A61F 2250/0006* (2013.01); *A61F 2250/0098* (2013.01); *A61F 2310/00017* (2013.01); *A61F 2310/00023* (2013.01); *A61F 2310/00029* (2013.01); *A61F 2310/0097* (2013.01); *A61F 2310/00101* (2013.01); *A61F 2310/00137* (2013.01); *A61F 2310/00796* (2013.01); *A61F 2310/00952* (2013.01); *A61F 2310/00976* (2013.01)

(56) References Cited

U.S. PATENT DOCUMENTS

| | | |
|---|---|---|
| 4,541,423 A | 9/1985 | Barber |
| 4,569,338 A | 2/1986 | Edwards |
| 4,636,217 A | 1/1987 | Ogilvie et al. |
| 4,653,489 A | 3/1987 | Tronzo |
| 4,716,893 A | 1/1988 | Fischer et al. |
| 4,725,264 A | 2/1988 | Glassman |
| 4,733,665 A | 3/1988 | Palmaz |
| 4,759,769 A | 7/1988 | Hedman et al. |
| 4,763,644 A | 8/1988 | Webb |
| 4,863,476 A | 9/1989 | Shepperd |
| 4,886,062 A | 12/1989 | Wiktor |
| 4,911,718 A | 3/1990 | Lee et al. |
| 4,932,975 A | 6/1990 | Main et al. |
| 4,941,466 A | 7/1990 | Romano |
| 4,969,888 A | 11/1990 | Scholten et al. |
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,192,327 A | 3/1993 | Brantigan |
| 5,217,483 A | 6/1993 | Tower |
| 5,258,031 A | 11/1993 | Salib et al. |
| 5,306,278 A | 4/1994 | Dahl et al. |
| 5,324,295 A | 6/1994 | Shapiro, III |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | Mckay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,895,387 A | 4/1999 | Guerrero et al. |
| 5,902,475 A | 5/1999 | Trozera et al. |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 5,993,483 A | 11/1999 | Gianotti |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,158 A | 6/2000 | Lin |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,619 A | 8/2000 | Truebe et al. |
| 6,102,950 A | 8/2000 | Vaccaro |
| 6,113,628 A | 9/2000 | Borghi |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |
| 6,132,465 A | 10/2000 | Ray et al. |
| 6,140,452 A | 10/2000 | Felt et al. |
| 6,146,417 A | 11/2000 | Ischinger |

(56) References Cited

U.S. PATENT DOCUMENTS

| | | |
|---|---|---|
| 6,159,244 A | 12/2000 | Suddaby |
| 6,159,245 A | 12/2000 | Meriwether et al. |
| 6,168,616 B1 | 1/2001 | Brown |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |
| 6,224,607 B1 | 5/2001 | Michelson |
| 6,235,043 B1 | 5/2001 | Reiley et al. |
| 6,241,734 B1 | 6/2001 | Scribner et al. |
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,296,644 B1 | 10/2001 | Saurat et al. |
| 6,302,914 B1 | 10/2001 | Michelson |
| 6,332,895 B1 | 12/2001 | Suddaby |
| 6,371,989 B1 | 4/2002 | Chauvin et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | Cox et al. |
| 6,475,237 B2 | 11/2002 | Drasler et al. |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |
| 6,514,255 B1 | 2/2003 | Ferree |
| 6,520,991 B2 | 2/2003 | Huene |
| 6,533,817 B1 | 3/2003 | Norton et al. |
| 6,551,342 B1 | 4/2003 | Shen et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,736,818 B2 | 5/2004 | Perren et al. |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Cragg |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 6,988,710 B2 | 1/2006 | Igarashi |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |

(56) References Cited

U.S. PATENT DOCUMENTS

| | | |
|---|---|---|
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,452,371 B2 | 11/2008 | Pavcnik et al. |
| 7,488,337 B2 | 2/2009 | Saab et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,625,395 B2 | 12/2009 | Mückter |
| 7,628,807 B2 | 12/2009 | Flanagan |
| 7,722,674 B1 | 5/2010 | Grotz |
| 7,749,228 B2 | 7/2010 | Lieberman |
| 7,763,028 B2 | 7/2010 | Lim et al. |
| 7,771,463 B2 | 8/2010 | Ton et al. |
| 7,828,849 B2 | 11/2010 | Lim |
| 7,837,734 B2 | 11/2010 | Zucherman et al. |
| 7,846,206 B2 | 12/2010 | Oglaza et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 8,007,498 B2 | 8/2011 | Mische |
| 8,034,110 B2 | 10/2011 | Garner et al. |
| 8,062,375 B2 | 11/2011 | Glerum et al. |
| 8,105,382 B2 | 1/2012 | Olmos et al. |
| 8,142,507 B2 | 3/2012 | McGuckin |
| 8,162,943 B2 | 4/2012 | Justin et al. |
| 8,206,423 B2 | 6/2012 | Siegal |
| 8,246,622 B2 | 8/2012 | Siegal et al. |
| 8,262,737 B2 | 9/2012 | Bagga et al. |
| 8,425,570 B2 | 4/2013 | Reiley |
| 8,465,524 B2 | 6/2013 | Siegal |
| 8,486,149 B2 | 7/2013 | Saidha et al. |
| 8,512,408 B2 | 8/2013 | Miller et al. |
| 8,518,120 B2 | 8/2013 | Glerum et al. |
| 8,535,380 B2 | 9/2013 | Greenhalgh et al. |
| 8,551,171 B2 | 10/2013 | Johnson et al. |
| 8,556,979 B2 | 10/2013 | Glerum et al. |
| 8,579,912 B2 | 11/2013 | Isaza et al. |
| 8,591,582 B2 | 11/2013 | Anderson et al. |
| 8,672,968 B2 | 3/2014 | Stone et al. |
| 8,672,977 B2 | 3/2014 | Siegal et al. |
| 8,679,183 B2 | 3/2014 | Glerum et al. |
| 8,685,098 B2 | 4/2014 | Glerum et al. |
| 8,709,042 B2 | 4/2014 | Greenhalgh et al. |
| 8,777,993 B2 | 7/2014 | Siegal et al. |
| 8,845,731 B2 | 9/2014 | Weiman |
| 8,845,734 B2 | 9/2014 | Weiman |
| 9,050,112 B2 | 6/2015 | Greenhalgh et al. |
| 9,149,286 B1 | 10/2015 | Greenhalgh et al. |
| 9,216,095 B2 | 12/2015 | Glerum et al. |
| 9,259,329 B2 | 2/2016 | Greenhalgh et al. |
| 9,314,349 B2 | 4/2016 | Greenhalgh et al. |
| 9,402,739 B2 | 8/2016 | Weiman et al. |
| 9,408,708 B2 * | 8/2016 | Greenhalgh .......... A61F 2/4425 |
| 9,510,885 B2 | 12/2016 | Burger et al. |
| 9,770,339 B2 | 9/2017 | Greenhalgh et al. |
| 10,070,968 B2 | 9/2018 | Greenhalgh et al. |
| 10,285,819 B2 | 5/2019 | Greenhalgh |
| 10,285,820 B2 | 5/2019 | Greenhalgh |
| 10,292,828 B2 | 5/2019 | Greenhalgh |
| 10,758,289 B2 | 9/2020 | Greenhalgh et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0038767 A1 | 4/2002 | Trozera |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0171813 A1 | 9/2003 | Kiester |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | Mcguckin |
| 2003/0199981 A1 | 10/2003 | Ferree |
| 2003/0204189 A1 | 10/2003 | Cragg |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |

(56) References Cited

U.S. PATENT DOCUMENTS

| | | |
|---|---|---|
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | Mckay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087947 A1 | 5/2004 | Lim et al. |
| 2004/0087950 A1 | 5/2004 | Teitelbaum |
| 2004/0092933 A1 | 5/2004 | Shaolian et al. |
| 2004/0092946 A1 | 5/2004 | Bagga et al. |
| 2004/0092988 A1 | 5/2004 | Shaolian et al. |
| 2004/0097927 A1 | 5/2004 | Yeung et al. |
| 2004/0102848 A1 | 5/2004 | Michelson |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1* | 8/2004 | Lim ............... A61F 2/4465 606/53 |
| 2004/0153146 A1 | 8/2004 | Lashinski et al. |
| 2004/0167625 A1 | 8/2004 | Beyar et al. |
| 2004/0172019 A1 | 9/2004 | Ferree |
| 2005/0010292 A1 | 1/2005 | Carrasco |
| 2005/0015152 A1 | 1/2005 | Sweeney |
| 2005/0022839 A1 | 2/2005 | Savas et al. |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0228472 A1 | 10/2005 | Case et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261695 A1 | 11/2005 | Cragg et al. |
| 2005/0261768 A1 | 11/2005 | Trieu |
| 2005/0261781 A1 | 11/2005 | Sennett et al. |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0022180 A1 | 2/2006 | Selness |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | Mckinley |
| 2006/0058880 A1 | 3/2006 | Wysocki et al. |
| 2006/0079898 A1 | 4/2006 | Ainsworth et al. |
| 2006/0085069 A1 | 4/2006 | Kim |
| 2006/0085070 A1 | 4/2006 | Kim |
| 2006/0089715 A1 | 4/2006 | Truckai et al. |
| 2006/0095123 A1 | 5/2006 | Flanagan |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0129244 A1 | 6/2006 | Ensign |
| 2006/0142858 A1 | 6/2006 | Colleran et al. |
| 2006/0142859 A1 | 6/2006 | Mcluen |
| 2006/0149239 A1 | 7/2006 | Winslow et al. |
| 2006/0149349 A1 | 7/2006 | Garbe |
| 2006/0149385 A1 | 7/2006 | Mckay |
| 2006/0155379 A1 | 7/2006 | Heneveld et al. |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0184248 A1 | 8/2006 | Edidin et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0235414 A1 | 10/2006 | Lim et al. |
| 2006/0235423 A1 | 10/2006 | Cantu |
| 2006/0241764 A1 | 10/2006 | Michelson |
| 2006/0253201 A1 | 11/2006 | Mcluen |
| 2006/0264968 A1 | 11/2006 | Frey et al. |
| 2006/0265077 A1 | 11/2006 | Zwirkoski |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055201 A1 | 3/2007 | Seto et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123877 A1 | 5/2007 | Goldin et al. |
| 2007/0123986 A1 | 5/2007 | Schaller |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0219634 A1 | 9/2007 | Greenhalgh et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0260315 A1 | 11/2007 | Foley et al. |
| 2007/0270956 A1 | 11/2007 | Heinz |
| 2007/0270968 A1* | 11/2007 | Baynham ............... A61F 2/447 623/17.11 |
| 2007/0276377 A1 | 11/2007 | Yundt |
| 2007/0276382 A1 | 11/2007 | Mikhail et al. |
| 2007/0282342 A1 | 12/2007 | Niederberger et al. |
| 2007/0288028 A1 | 12/2007 | Gorensek et al. |
| 2008/0015694 A1 | 1/2008 | Tribus |
| 2008/0021558 A1 | 1/2008 | Thramann |

(56) References Cited

U.S. PATENT DOCUMENTS

| | | |
|---|---|---|
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0082162 A1 | 4/2008 | Boismier et al. |
| 2008/0124865 A1 | 5/2008 | Lutze et al. |
| 2008/0125864 A1 | 5/2008 | De Villiers et al. |
| 2008/0125865 A1 | 5/2008 | Abdelgany |
| 2008/0133012 A1 | 6/2008 | Mcguckin |
| 2008/0140082 A1 | 6/2008 | Erdem et al. |
| 2008/0140179 A1 | 6/2008 | Ladisa |
| 2008/0140207 A1* | 6/2008 | Olmos ............... A61F 2/4611 623/17.16 |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0208255 A1 | 8/2008 | Siegal |
| 2008/0221687 A1 | 9/2008 | Viker |
| 2008/0243254 A1 | 10/2008 | Butler |
| 2008/0243255 A1 | 10/2008 | Butler et al. |
| 2008/0249625 A1 | 10/2008 | Waugh et al. |
| 2008/0249628 A1 | 10/2008 | Altarac et al. |
| 2008/0281346 A1 | 11/2008 | Greenhalgh et al. |
| 2008/0294205 A1 | 11/2008 | Greenhalgh et al. |
| 2008/0312743 A1 | 12/2008 | Vila et al. |
| 2008/0312744 A1 | 12/2008 | Vresilovic et al. |
| 2009/0005871 A1 | 1/2009 | White et al. |
| 2009/0012564 A1 | 1/2009 | Chirico et al. |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0054991 A1 | 2/2009 | Biyani et al. |
| 2009/0076511 A1 | 3/2009 | Osman |
| 2009/0143859 A1 | 6/2009 | Mcclellan et al. |
| 2009/0149956 A1 | 6/2009 | Greenhalgh et al. |
| 2009/0163918 A1 | 6/2009 | Levy et al. |
| 2009/0177207 A1 | 7/2009 | Schaller |
| 2009/0182336 A1 | 7/2009 | Brenzel et al. |
| 2009/0182431 A1 | 7/2009 | Butler et al. |
| 2009/0198338 A1 | 8/2009 | Phan |
| 2009/0222100 A1* | 9/2009 | Cipoletti ............... A61F 2/4611 623/17.16 |
| 2009/0234398 A1 | 9/2009 | Chirico et al. |
| 2009/0240335 A1 | 9/2009 | Arcenio et al. |
| 2009/0292323 A1 | 11/2009 | Chirico et al. |
| 2009/0299378 A1 | 12/2009 | Knopp |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0168748 A1 | 7/2010 | Knopp et al. |
| 2010/0168862 A1 | 7/2010 | Edie et al. |
| 2010/0191336 A1 | 7/2010 | Greenhalgh |
| 2010/0211176 A1 | 8/2010 | Greenhalgh |
| 2010/0262147 A1 | 10/2010 | Siegal et al. |
| 2010/0292796 A1 | 11/2010 | Greenhalgh et al. |
| 2010/0324560 A1 | 12/2010 | Suda |
| 2011/0009869 A1 | 1/2011 | Marino et al. |
| 2011/0009969 A1 | 1/2011 | Puno |
| 2011/0029083 A1 | 2/2011 | Hynes et al. |
| 2011/0046737 A1 | 2/2011 | Teisen |
| 2011/0054621 A1 | 3/2011 | Lim |
| 2011/0087296 A1 | 4/2011 | Reiley et al. |
| 2011/0106260 A1 | 5/2011 | Laurence et al. |
| 2011/0118785 A1 | 5/2011 | Reiley |
| 2011/0125266 A1 | 5/2011 | Rodgers et al. |
| 2011/0153019 A1 | 6/2011 | Siegal |
| 2011/0166575 A1 | 7/2011 | Assell et al. |
| 2011/0184519 A1 | 7/2011 | Trieu |
| 2011/0218626 A1 | 9/2011 | Krinke et al. |
| 2011/0230884 A1 | 9/2011 | Mantzaris et al. |
| 2011/0230966 A1 | 9/2011 | Trieu |
| 2011/0257684 A1 | 10/2011 | Sankaran |
| 2011/0282387 A1 | 11/2011 | Suh et al. |
| 2011/0282398 A1 | 11/2011 | Overes et al. |
| 2011/0282453 A1 | 11/2011 | Greenhalgh et al. |
| 2011/0319898 A1 | 12/2011 | O'Neil et al. |
| 2011/0320000 A1 | 12/2011 | O'Neil et al. |
| 2012/0004726 A1 | 1/2012 | Greenhalgh et al. |
| 2012/0004731 A1 | 1/2012 | Viker |
| 2012/0029518 A1 | 2/2012 | Blackwell et al. |
| 2012/0071962 A1 | 3/2012 | Huang et al. |
| 2012/0071980 A1 | 3/2012 | Purcell et al. |
| 2013/0035723 A1 | 2/2013 | Donner |
| 2013/0053852 A1 | 2/2013 | Greenhalgh et al. |
| 2013/0085535 A1 | 4/2013 | Greenhalgh et al. |
| 2013/0138214 A1 | 5/2013 | Greenhalgh et al. |
| 2013/0173004 A1 | 7/2013 | Greenhalgh et al. |
| 2013/0304224 A1 | 11/2013 | Schmidt et al. |
| 2014/0088713 A1 | 3/2014 | Greenhalgh et al. |
| 2014/0155980 A1 | 6/2014 | Turjman et al. |
| 2015/0230931 A1 | 8/2015 | Greenhalgh |
| 2015/0265417 A1 | 9/2015 | Greenhalgh et al. |
| 2015/0351930 A1 | 12/2015 | Greenhalgh et al. |
| 2016/0022429 A1 | 1/2016 | Greenhalgh et al. |
| 2016/0030099 A1 | 2/2016 | Greenhalgh et al. |
| 2016/0058572 A1 | 3/2016 | Greenhalgh et al. |
| 2016/0310291 A1 | 10/2016 | Greenhalgh |
| 2019/0231549 A1 | 8/2019 | Greenhalgh et al. |
| 2019/0254714 A1 | 8/2019 | Greenhalgh et al. |

FOREIGN PATENT DOCUMENTS

| | | |
|---|---|---|
| EP | 0758541 | 2/1997 |
| EP | 1804733 | 7/2007 |
| FR | 2874814 | 11/2007 |
| FR | 2900814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| JP | 2012-522961 | 9/2012 |
| SU | 662082 | 5/1979 |
| WO | WO 1988/003781 | 6/1988 |
| WO | WO 1992/014423 | 9/1992 |
| WO | WO 1995/031945 | 11/1995 |
| WO | WO 1996/003092 | 2/1996 |
| WO | WO 1997/000054 | 1/1997 |
| WO | WO 2000/025706 | 5/2000 |
| WO | WO 2000/030523 | 6/2000 |
| WO | WO 2000/044319 | 8/2000 |
| WO | WO 2000/044321 | 8/2000 |
| WO | WO 2001/032099 | 5/2001 |
| WO | WO 2001/078625 | 10/2001 |
| WO | WO 2001/095838 | 12/2001 |
| WO | WO 2002/013700 | 2/2002 |
| WO | WO 2002/032347 | 4/2002 |
| WO | WO 2003/003943 | 1/2003 |
| WO | WO 2003/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/068682 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116760 | 11/2006 |
| WO | WO 2006/116761 | 11/2006 |
| WO | WO 2006/132945 | 12/2006 |

(56) References Cited

FOREIGN PATENT DOCUMENTS

| | | |
|---|---|---|
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041665 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/073488 | 6/2007 |
| WO | WO 2007/075411 | 7/2007 |
| WO | WO 2007/076308 | 7/2007 |
| WO | WO 2007/076374 | 7/2007 |
| WO | WO 2007/076376 | 7/2007 |
| WO | WO 2007/076377 | 7/2007 |
| WO | WO 2007/079021 | 7/2007 |
| WO | WO 2007/084239 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/113808 | 10/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/016598 | 2/2008 |
| WO | WO 2008/036505 | 3/2008 |
| WO | WO 2008/070863 | 6/2008 |
| WO | WO 2009/039430 | 3/2009 |
| WO | WO 2009/067568 | 5/2009 |
| WO | WO 2009/114381 | 9/2009 |
| WO | WO 2009/130824 | 10/2009 |
| WO | WO 2010/013188 | 2/2010 |
| WO | WO 2010/121002 | 10/2010 |
| WO | WO 2011/014502 | 2/2011 |
| WO | WO 2011/049949 | 4/2011 |
| WO | WO 2011/142761 | 11/2011 |
| WO | WO 2011/149557 | 12/2011 |
| WO | WO 2012/027490 | 3/2012 |
| WO | WO 2012/040272 | 3/2012 |
| WO | WO 2012/083173 | 6/2012 |
| WO | WO 2013/028808 | 2/2013 |
| WO | WO 2013/119332 | 8/2013 |

OTHER PUBLICATIONS

Database WPI, Week 198004, Thomson Scientific, London, GB; AN 1980-A8866C, XP002690114, -& SU 662 082 A1 (Tartus Univ) May 15, 1979 (May 15, 1979), abstract, figures 1,2.

Franklin, I.J. et al., "Uptake of Tetracycline by Aortic Aneurysm Wall and Its Effect on Inflammation and Proteolysis," *Brit. J. Surger*, 86(6):771-775, Jun. 1999.

Pyo, R. et al., "Targeted Gene Disruption of Matrix Metalloproteinase-9 (Gelatinase B) Suppresses Development of Experimental Abdominal Aortic Aneurysms," *J. Clinical Investigation*,105(11):1641-1649, Jun. 2000.

Tambiah, J. et al., "Provocation of Experimental Aortic Inflammation Mediators and Chlamydia Pneumoniae," *Brit., J. Surgery*, 88(7):935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

\* cited by examiner

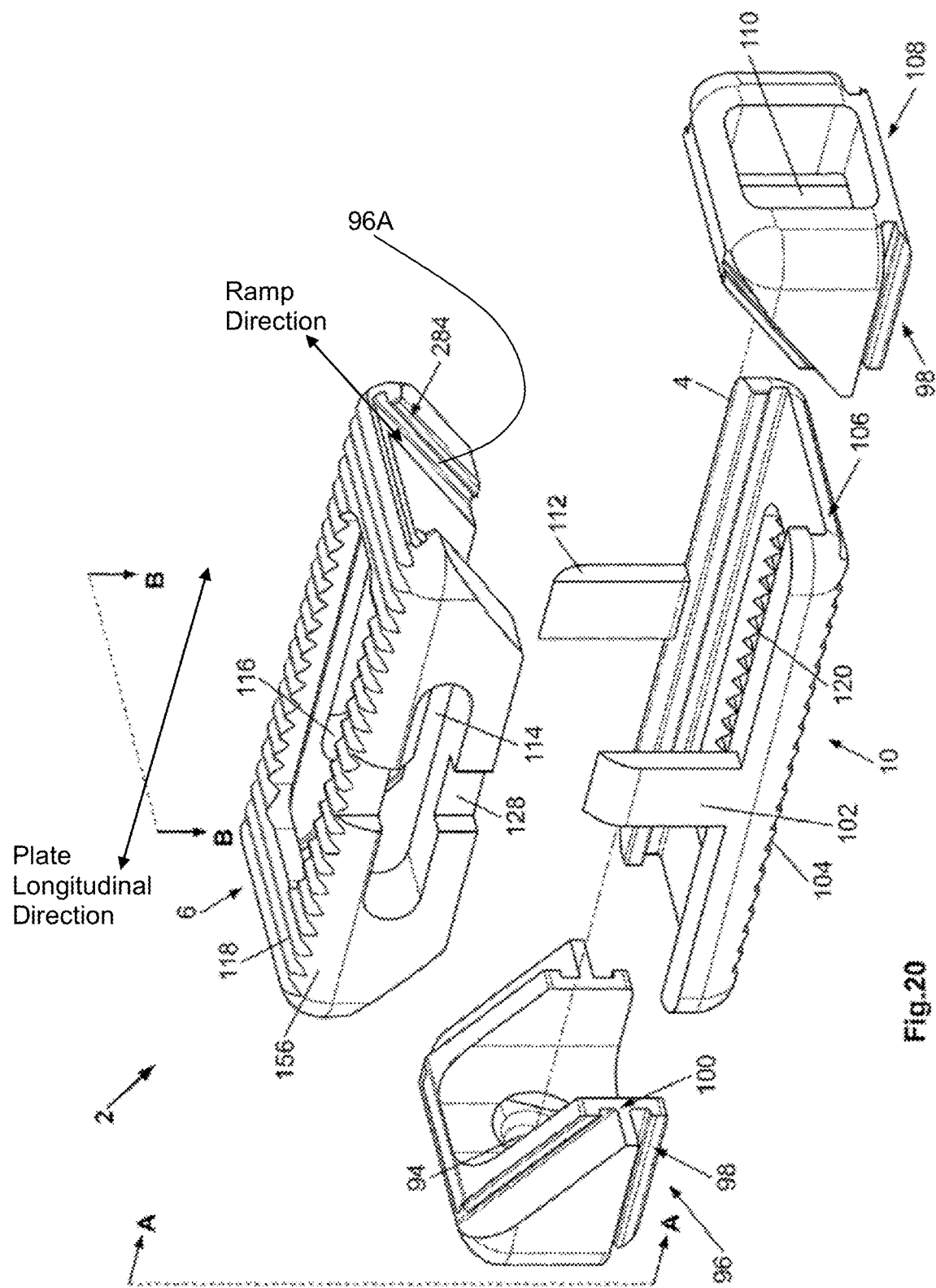

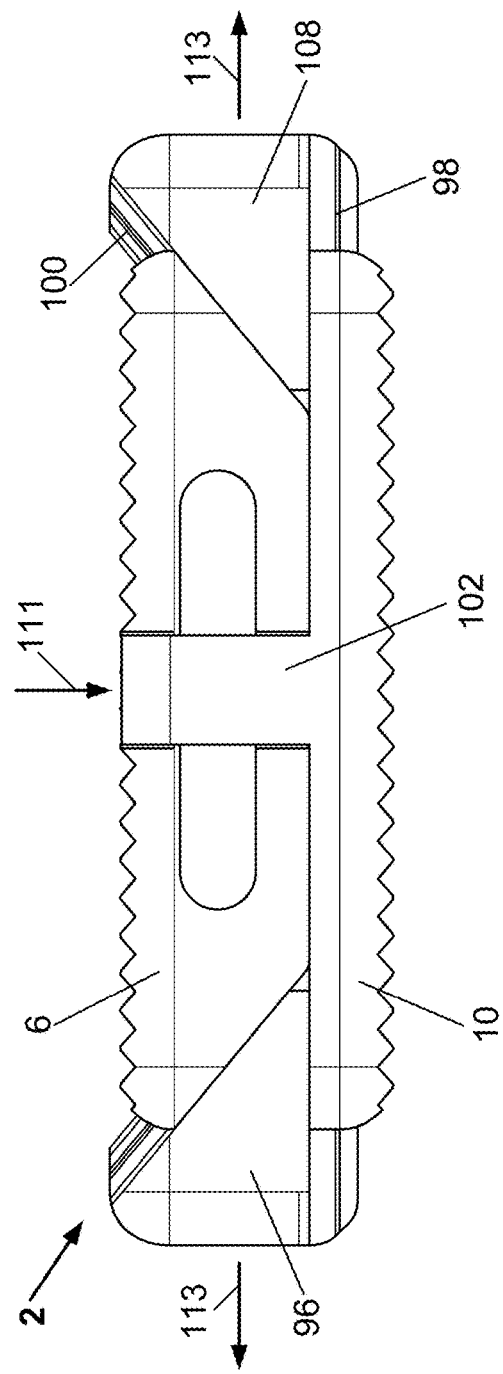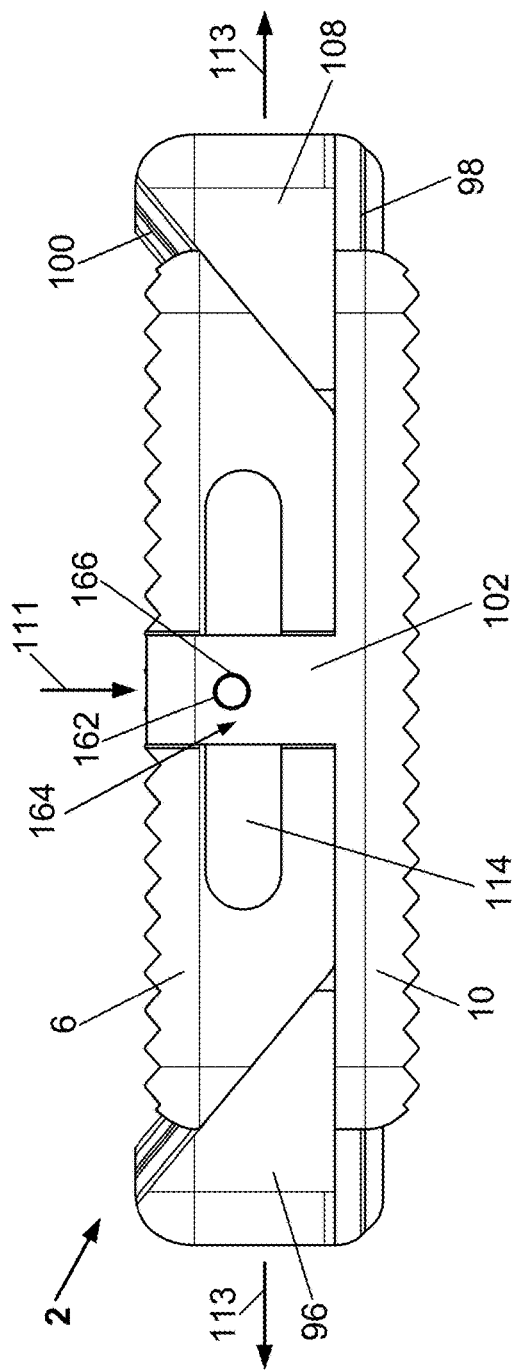

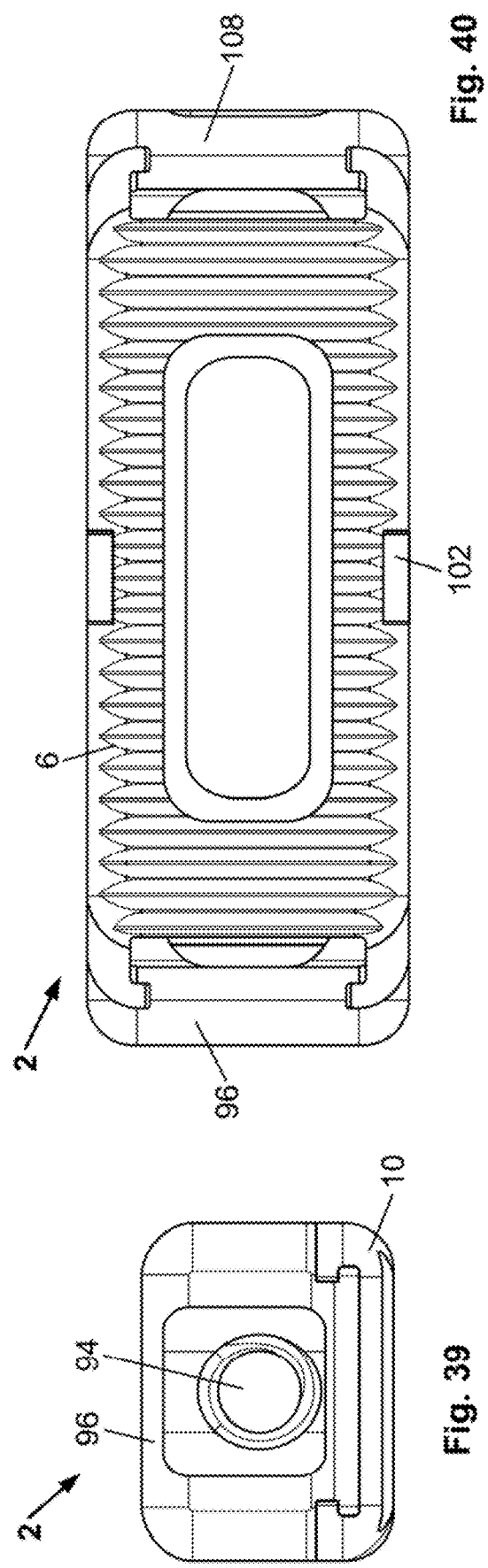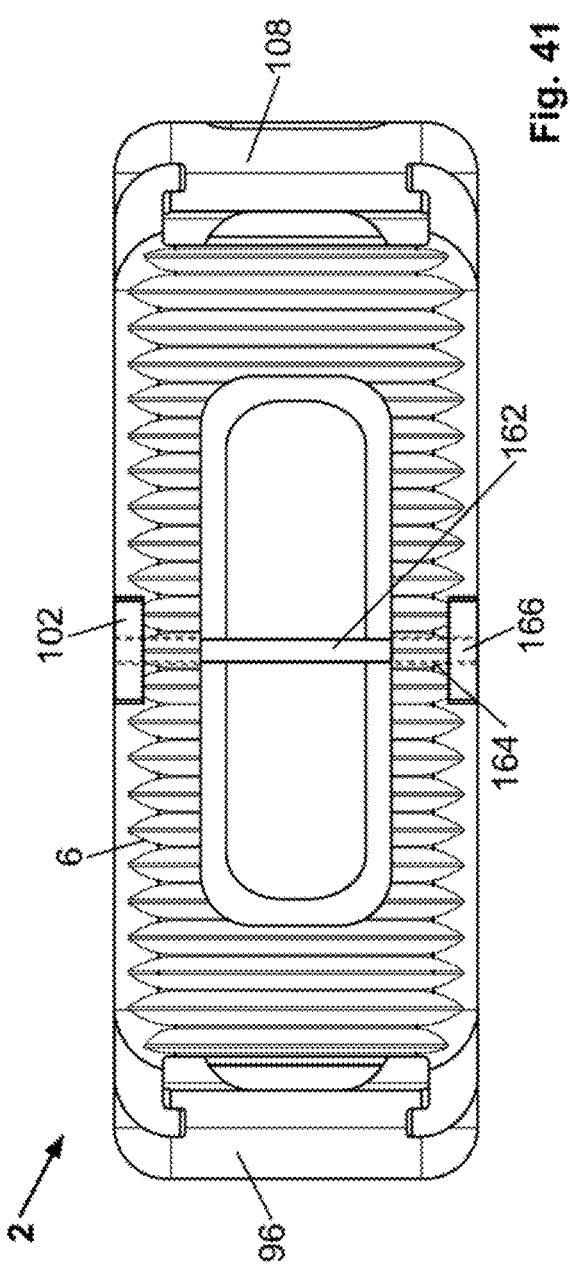

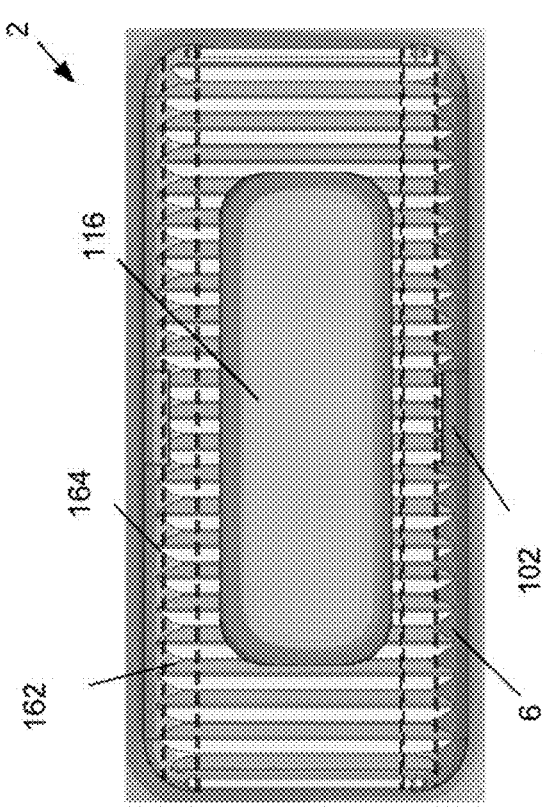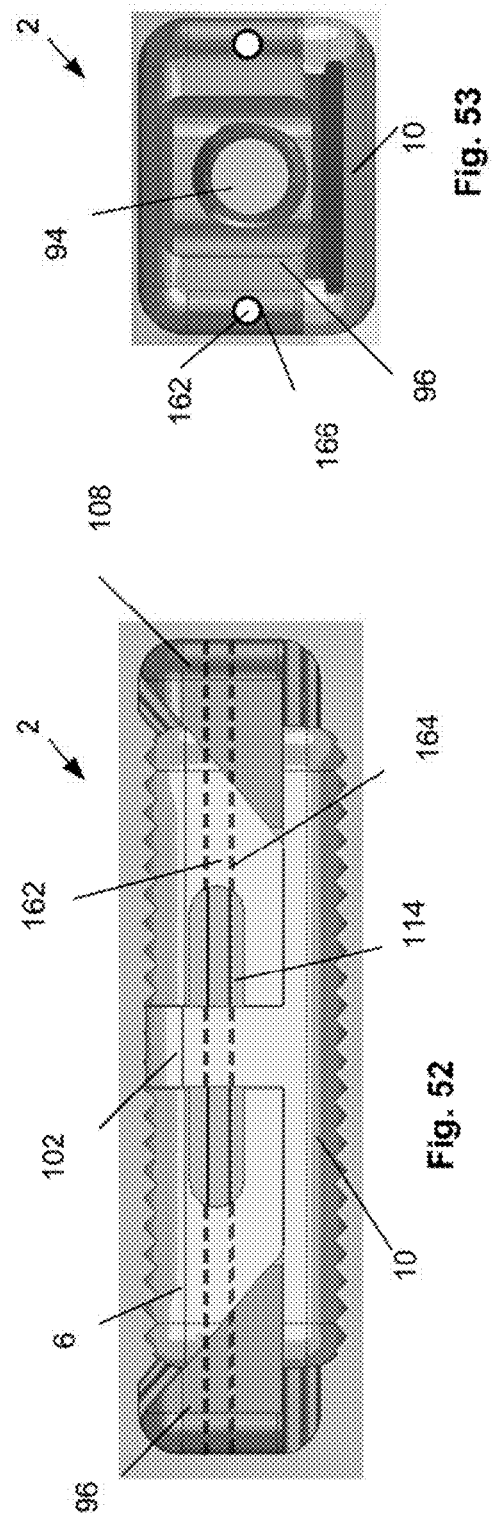

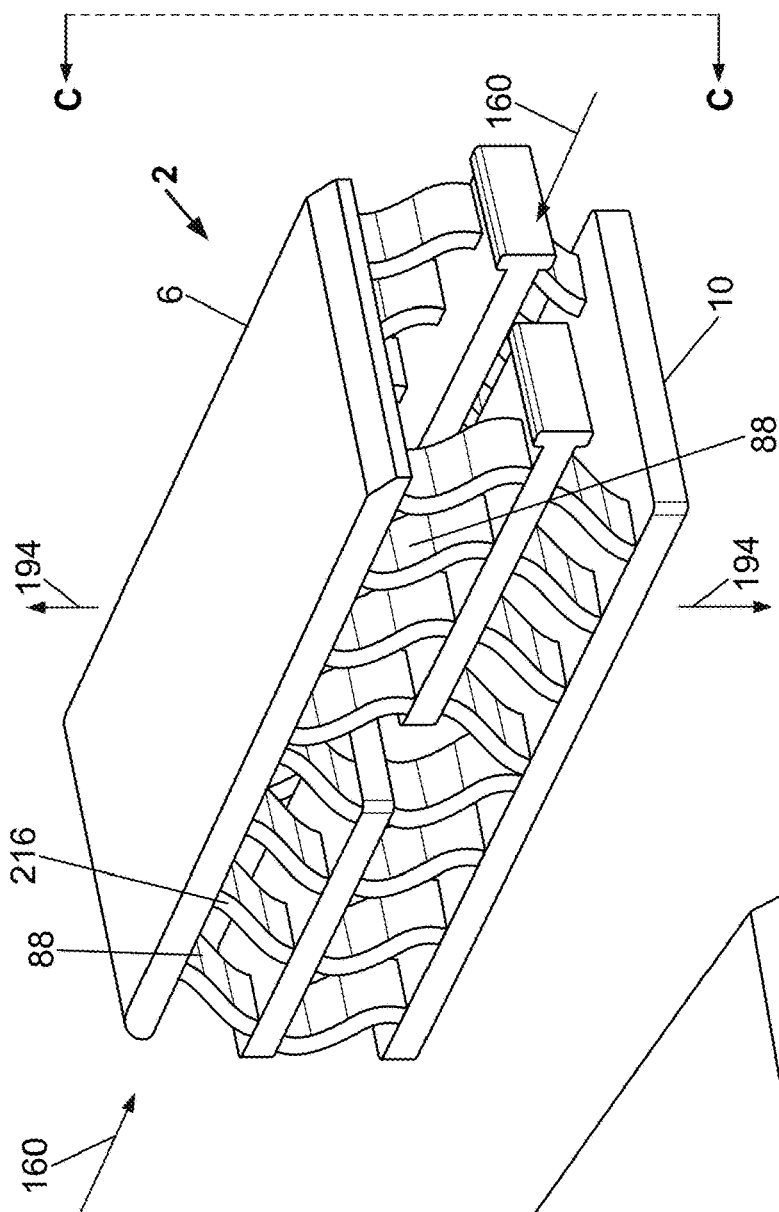
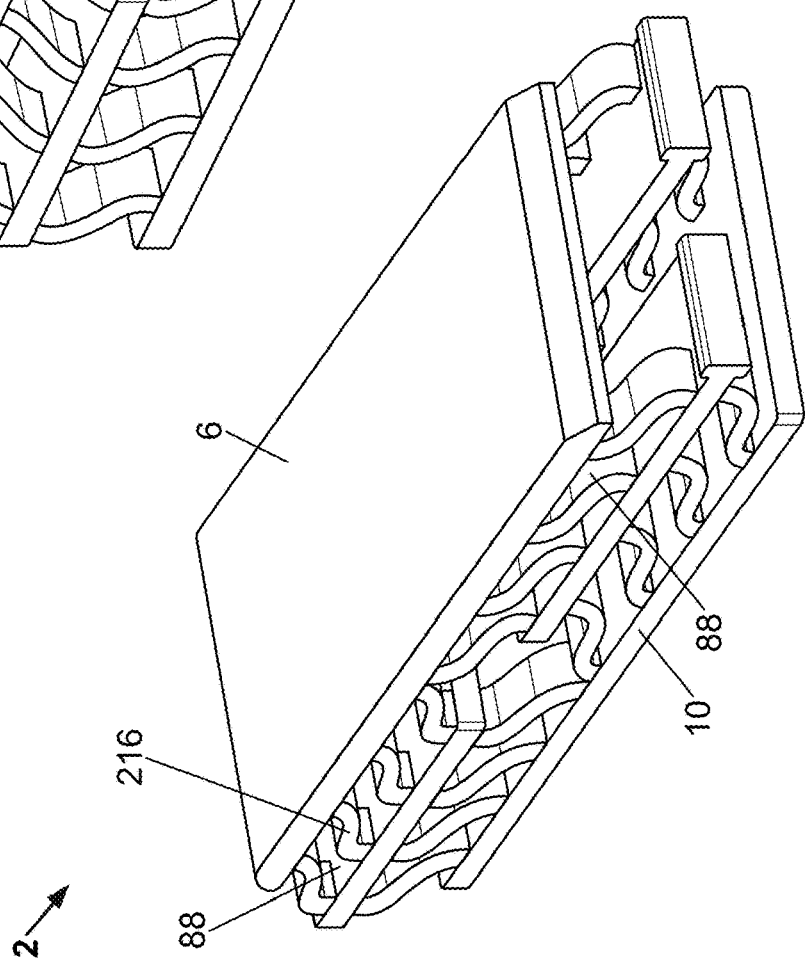
Fig. 66b
Fig. 66a

US 10,940,014 B2

FIXATION DEVICE AND METHOD

CROSS-REFERENCE TO RELATED APPLICATIONS

This application is a continuation of U.S. patent application Ser. No. 15/975,631, filed May 9, 2018, which is a continuation of U.S. patent application Ser. No. 15/202,405, filed Jul. 5, 2016, now abandoned, which is a continuation of U.S. patent application Ser. No. 12/617,663, filed Nov. 12, 2009, now U.S. Pat. No. 9,408,708, which claims the benefit of U.S. Patent Application No. 61/113,691, filed Nov. 12, 2008, each of which is incorporated herein by reference in their entirety.

BACKGROUND OF THE INVENTION

1. Technical Field

Devices and methods for fixation of tissue are disclosed. More specifically, the devices and methods can be for inter facet fusion of vertebrae or fusion of other bones to one another.

2. Background of the Art

Spinal fusion is typically performed by a screw or rod system with an allograft, Titanium, or PEEK device placed between vertebral bodies. Facet screws have been used for many years but have not had favor due to lacking the ability to create bone growth across the facet joint. A typical facet screw is described in Sasso, Rick C., et al. "Translaminar Facet Screw Fixation", World Spine Journal (WSJ). 2006; 1(1):34-39, <http://www.worldspine.org/Documents/WSJ/1-1/Sasso_TLFS.pdf> which is incorporated by reference in its entirety.

SUMMARY OF THE INVENTION

A device that can replace or supplement the screw or rod elements of a typical fusion system is disclosed. The device can be placed in the inter-facet space to fuse adjacent vertebrae and/or create a bone mass within the facet joint in a patient's spine.

The device can be less invasive than typical existing devices. For example, the device can be in a compacted (i.e., small) configuration when inserted into a patient and transformed into an expanded (i.e., large) configuration when positioned at the target site. For example, the device can be expanded when the device is between the inferior and superior facet surfaces. The device can create less soft tissue (e.g., bone) disruption than a typical fusion system. The device in an expanded configuration can improve anchoring within the joint, structural stability, and create an environment for bone healing and growth leading to fusion between adjacent vertebrae.

During deployment into tissue (e.g., bone), one, two or more holes can be drilled into the target site to create a deployment hole in which to insert the device. The deployment hole can be round or non-round (e.g., by drilling more than one overlapping or adjacent hole, or crafting a square or rectangular hole), for example to substantially match the transverse cross-section of the device in a contracted configuration.

The device can be cannulated, for example having a lateral (i.e., transverse or latitudinal) and/or lengthwise (i.e., longitudinal) channel through the device. The device can be deployed over a wire or leader, such as a guidewire. The device can be slid over the guidewire, with the guidewire passing through the longitudinal channel of the device.

BRIEF DESCRIPTION OF THE DRAWINGS

FIG. 1b is a variation of cross-section A-A of FIG. 1a.

FIG. 2a is side view of a variation of cross-section A-A of FIG. 1a.

FIG. 3a is a variation of cross-section A'-A' of FIG. 1a.

FIG. 20 is an exploded view of a variation of the expandable support device.

FIGS. 36, 37, 39 and 40 are perspective, side, end and top views, respectively, of the variation of the device of FIG. 20 in a pre-deployment configuration.

FIGS. 38 and 41 are side and top views, respectively, of a variation of the device of FIG. 20 in a pre-deployment configuration.

FIG. 41 is illustrated with the top and the base in see-through views for illustrative purposes.

FIGS. 51, 52 and 53 are top, side and end views, respectively, of a variation of the device with the locking pin.

FIG. 66a illustrates a variation of the device in a contracted configuration.

FIG. 66b illustrates the device of FIG. 66a in an expanded configuration.

DETAILED DESCRIPTION

Figure 1A:
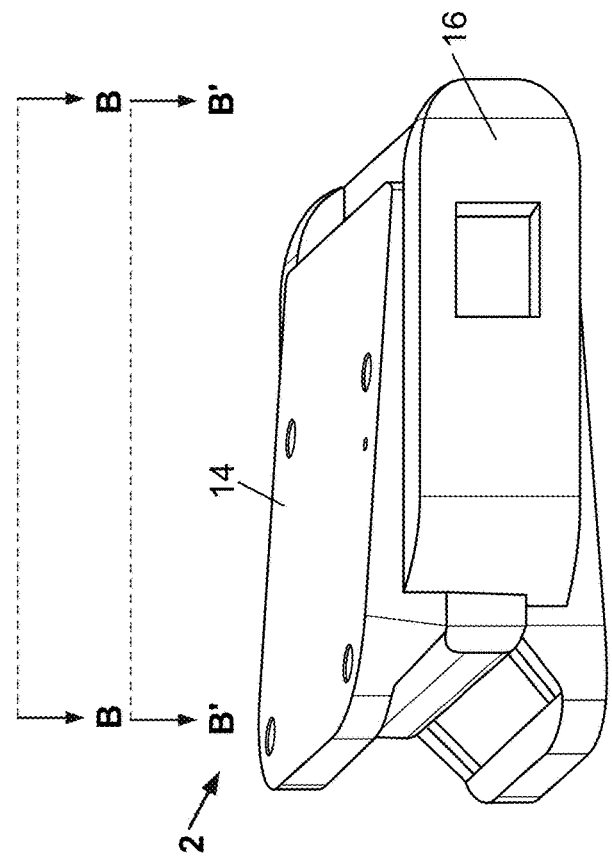
FIG. 1a is a side perspective view of a variation of the device in a contracted configuration.
Figure 1C:
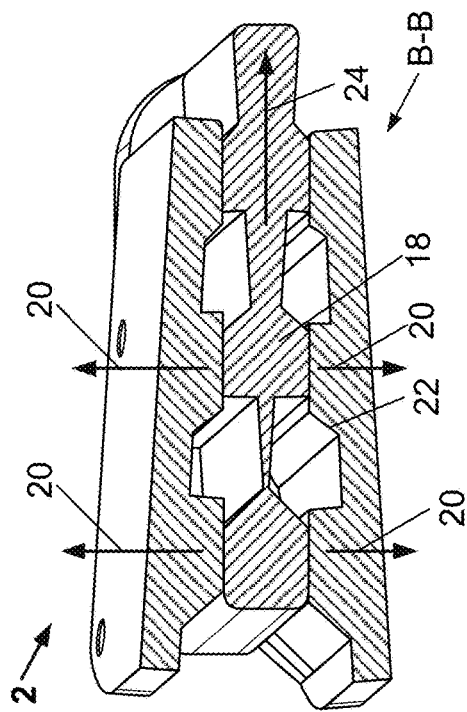
FIG. 1c is a side perspective view of the device of FIG. 1a in an expanded configuration.
Figure 1B:
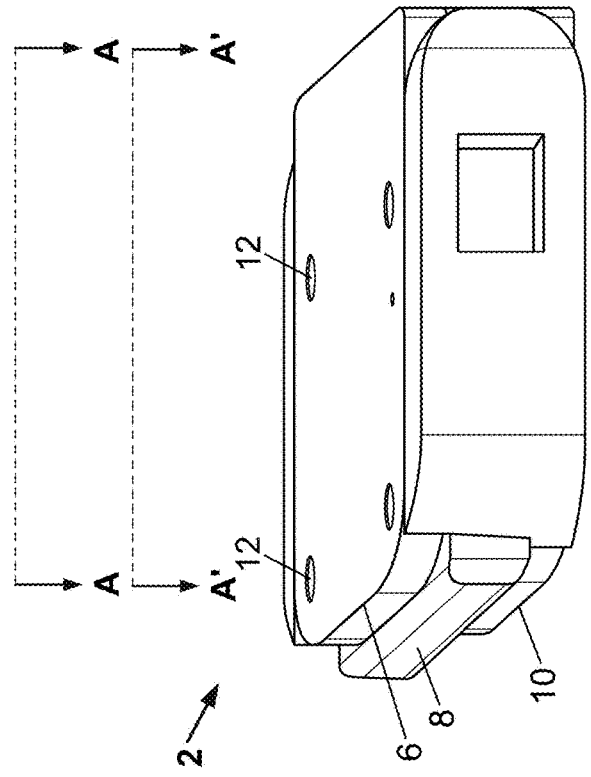
Figure 1D:
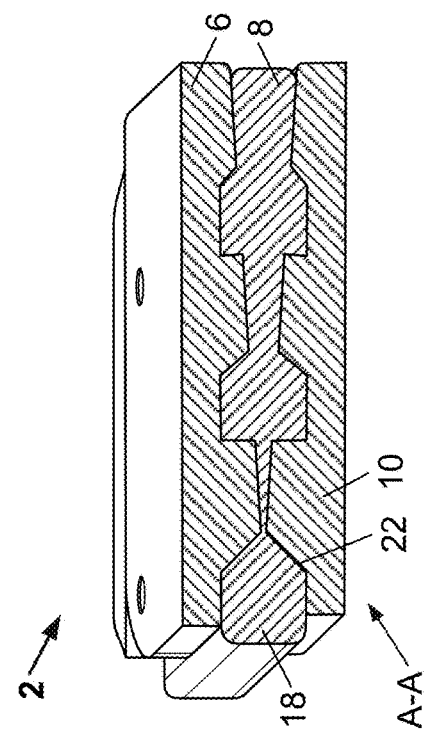
FIG. 1d is a variation of cross-section B-B of FIG. 1c.
Figure 2A:
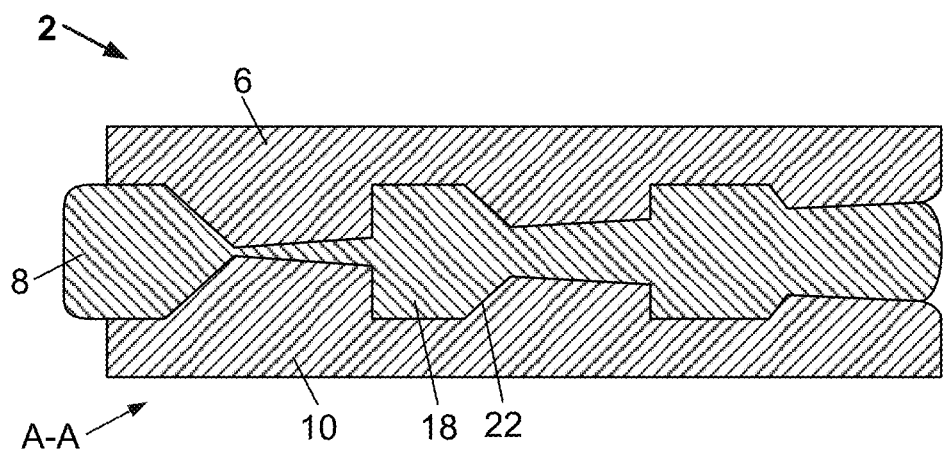
Figure 2B:
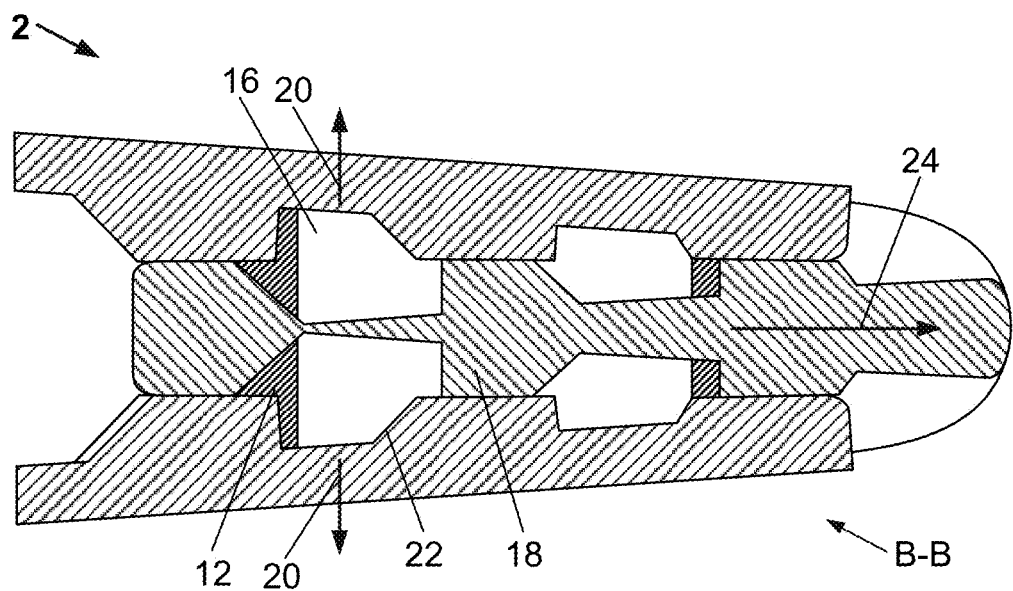
FIG. 2b is side view of a variation of cross-section B-B of FIG. 1b.

A device 2 is disclosed that can be inserted into a target site with the device 2 in a compressed or contracted (i.e., small) configuration. Once positioned in the deployment site, the device 2 can be transformed into an expanded (i.e., larger, bigger) configuration. The device 2 can be inserted and expanded in orthopedic target sites for fixation and/or support. For example, the device 2 can be inserted and expanded over a guidewire between adjacent vertebral facet surfaces (i.e., within a facet joint).

FIGS. 1a through 3c illustrate that the device 2 can have a top plate 6 attached to a bottom plate 10. The top plate 6 can be attached to the bottom plate 10 by one, two, three four or more pins 12. The plates can have a substantially flat external surface facing outward from the device 2. The pin longitudinal axes 4 can be substantially perpendicular to the plate surface planes 32 of the external surfaces of the top and bottom plates 6, 10 when the device 2 is in a contracted configuration, and perpendicular to the device longitudinal axis 4.

The device 2 can have a middle plate 8 positioned between the top plate 6 and the bottom plate 10. The middle plate 8 can be slidably attached to the top plate 6 and the bottom plate 10. The pins 12 can be in pin slots 14 in the top and/or bottom and/or middle plates 6, 10, 8. The pin slots 14 in the middle plate 8 can fix the pins 12 with respect to the position of the middle plate 8 in the direction of a device longitudinal axis 4. The pin slots 14 in the top and bottom plates 6, 10 can allow the pins 12 to move along a device longitudinal axis 4 with respect to the top and bottom plates 6, 10 to the extent of the pin slots 14, at which point the pin slots 14 will interference fit against the pins 12 to prevent further motion of the top and bottom plates 6, 10. Accordingly, the top and bottom plates 6, 10 can slide with respect to each other and to the middle plate 8 in the direction of the device longitudinal axis 4 (and/or the middle plate longitudinal axis).

The top plate 6 can have one or more angled and/or curved ramps 22 on the middle plate-side of the top plate 6. The bottom plate 10 can have one or more angled and/or curved ramped 22 on the middle plate-side of the bottom plate 10. The middle plate 8 can have angled and/or curved wedges 18 on the top plate-side and/or bottom plate-side of the middle plate 8. The wedges 18 can interface with the ramps 22. For example, the top and bottom plates 6, 10 can be in a contracted, compressed, or otherwise non-expanded configuration when the middle plate 8 is in a first position relative to the top and bottom plates 6, 10. The top and/or bottom plates 6, 10 can be in an expanded 20, radially spread, or enlarged configuration when the middle plate 8 is in a second position (e.g., pulled away) relative to the top and/or bottom plates 6, 10.

The middle plate 8 can have no, one or two side walls 16. The side walls 16 can extend to about the height of the top plate 6 and/or bottom plate 10 when the device 2 is in a contracted or expanded 20 configuration.

The top plate 6, bottom plate 10, side plates and combinations thereof can have ingrowth channels 28, windows, or ports. The ingrowth channels 28 can be configured to encourage bone growth into the ingrowth channel 28. For example, the ingrowth channels 28 can have textured surface and/or be coated and/or partially or completely filled with one or more osteogenic or osteoinductive material, for example any of those disclosed below.

Figure 3A:
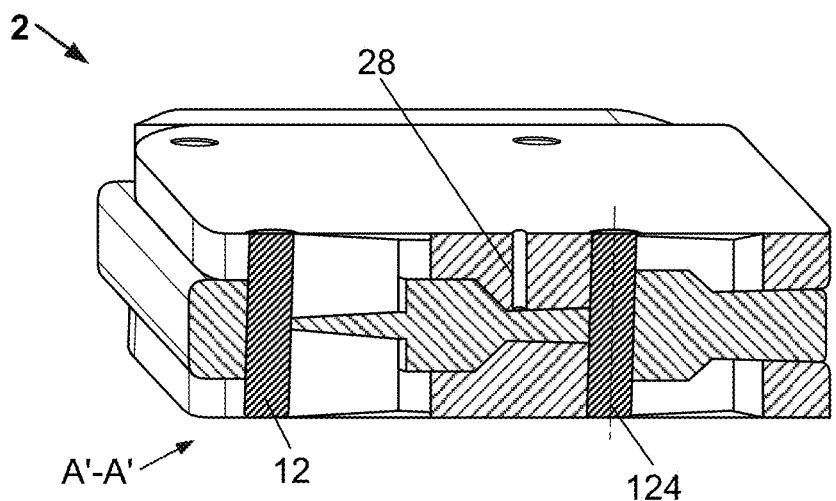
Figure 3B:
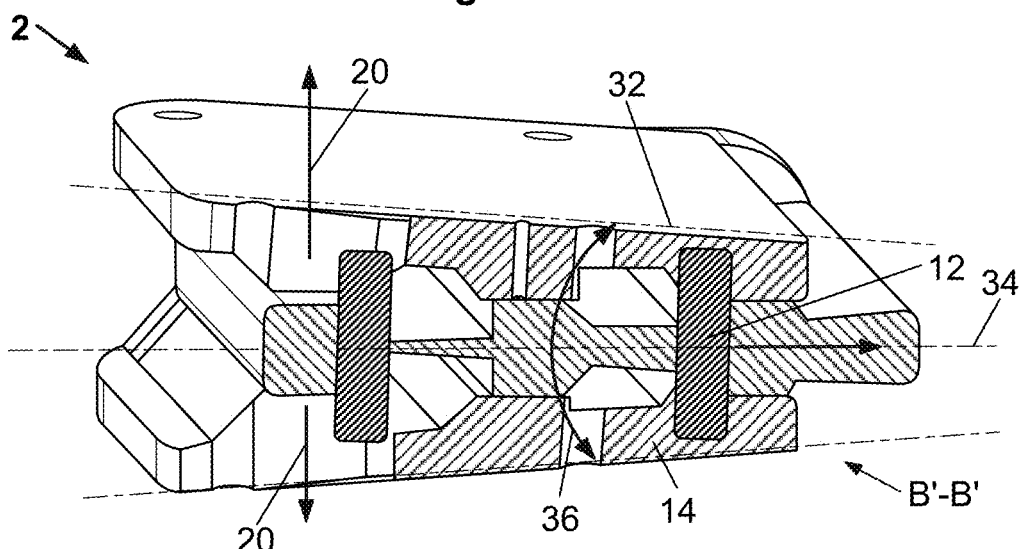
FIG. 3b is a variation of cross-section B'-B' of FIG. 1b.
Figure 3C:
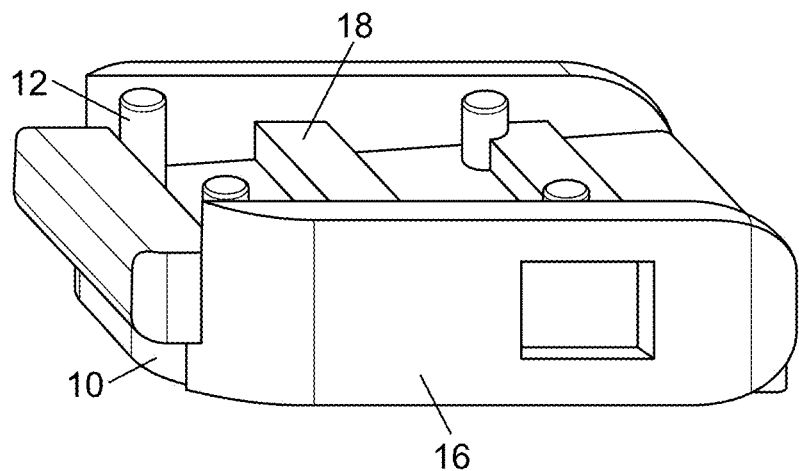
FIG. 3c is a variation of FIG. 1a with the top plate absent.
Figure 4:
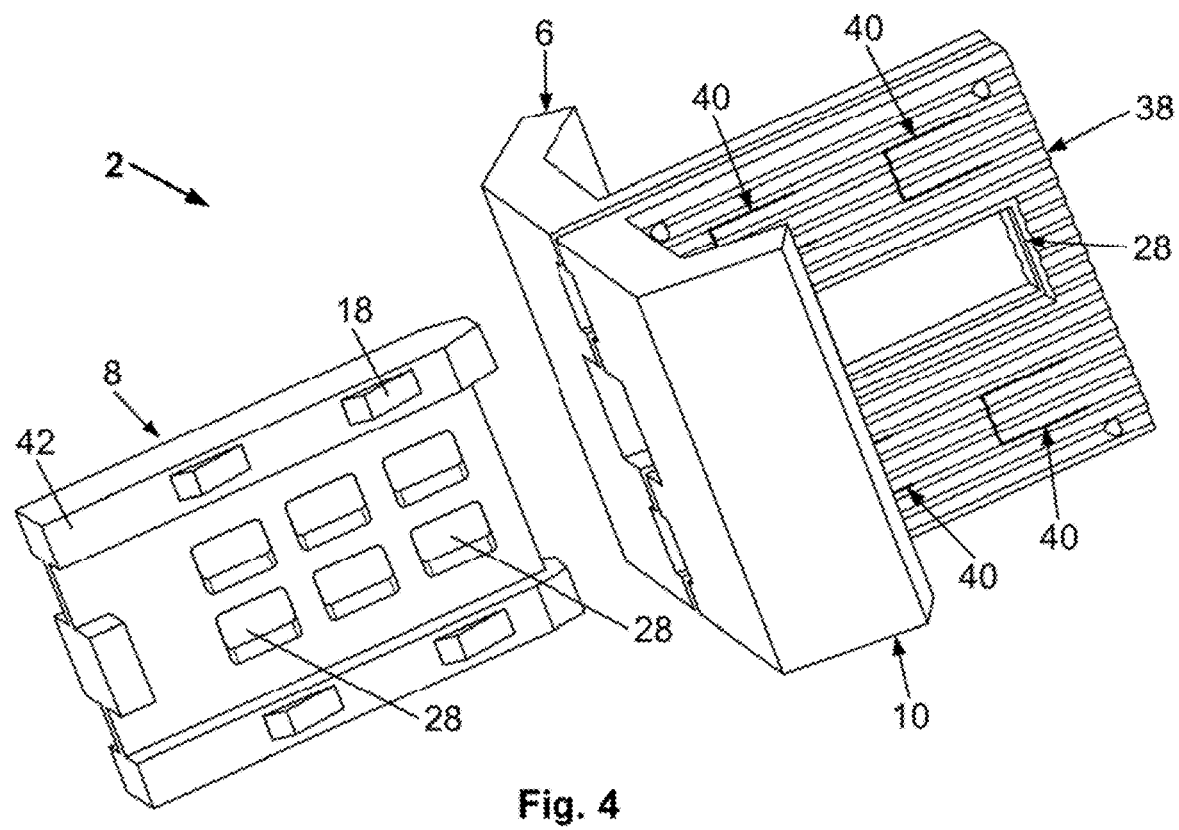
FIGS. 4 through 8 illustrate various views and configurations of a variation of the device.
Figure 5:
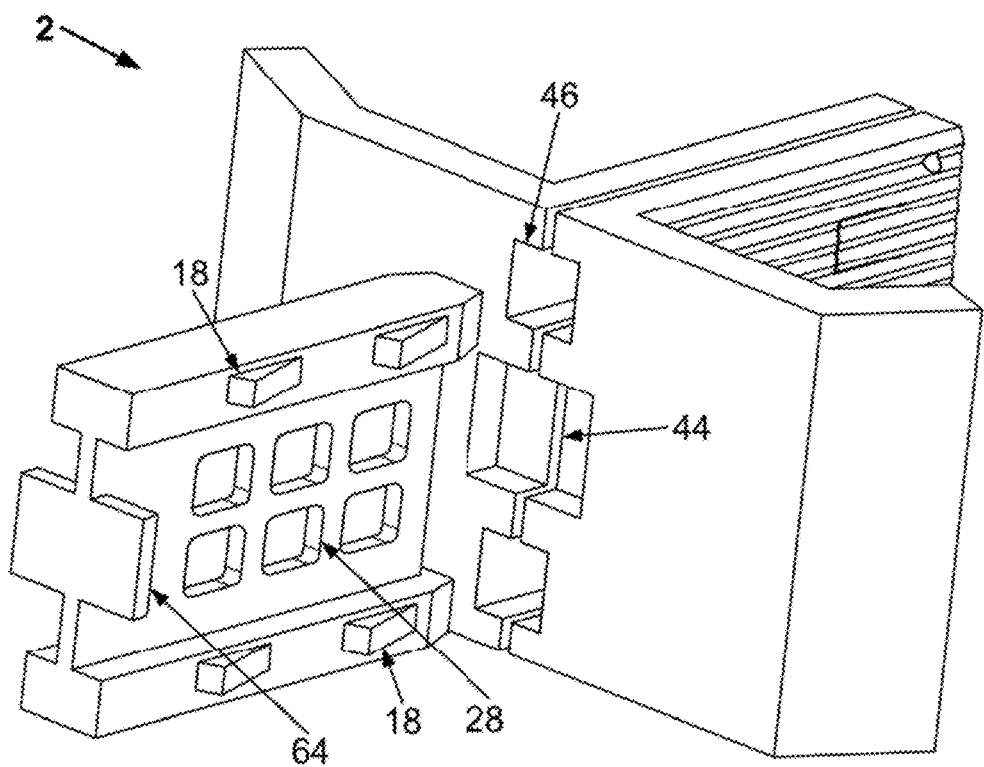

FIGS. 3a and 3b illustrate that the pins 12 can be contained by the top and bottom plates 6, 10 during expansion of the device 20. The pins 12 can be radiopaque and/or anti-torque. The side walls 16 can brace or otherwise interference fit the top and/or bottom plates 6, 10, for example to minimize lateral movement of the top and/or bottom plates 6, 10 relative to the middle plate 8.

When the device 2 is in an expanded configuration 20, the top plate surface plane 32 and the bottom plate surface plane can form a device expansion angle 36. The device expansion angle 36 can be from about 1° to about 45°, more narrowly from about 2° to about 20°. For example, the device expansion angle 36 can be about 5° or about 10°. The device 2 can have a ratchet, or steps or teeth on the ramp 22 and wedges 18 to allow the device expansion angle 36 to be expanded at discrete increments, such as increased at increments of about 0.25°, about 0.5°, about 1°, or about 2°.

FIGS. 4 through 8 illustrate that the top and/or bottom plates 6, 10 can have inner panels that are adjacent to and oppose each other. The top and/or bottom plates 6, 10 can have respective deployment stop panels 52, 62 and/or wing panels 50, 60. The deployment stop panels 52, 62 can extend at substantially perpendicular angles (e.g., from about 80° to about 100°, for example about 90°) from the inner panels 54, 58. The wing panels 50, 60 can extend at angles from the ends of the deployment stop panels 52, 62 away from the side of the inner panels 54, 58. For example, the wing panels 50, 60 can extend from the deployment stop panels 52, 62 at about 0° to about 60°, more narrowly from about 5° to about 45°, for example about 30°.

During use, the deployment stop panels 52, 62 and/or the wing panels 50, 60 can interference fit against the outside of the bone (e.g., the facet) to prevent overinsertion or misplacement of the device 2 into the target site. The deployment stop panels 52, 62 and/or wing panels 50, 60 can contact the facets and/or vertebral body side wall when implanted in the vertebral body disc space. The deployment stop panels 52, 62 and/or wing panels 50, 60 can abut and interference fit against the bone outside of the joint of the target site to prevent the device 2 from being inserted too far into the joint space. Additional anchoring elements, such as drive screws, can be inserted through the deployment stop panel 52, 62 and/or wing panel 50, 60 and the adjacent tissue (e.g., into the vertebral side wall and/or facet) before, during or after the device 2 is expanded to fix the device 2 to the target site. The device 2 can be retrieved or repositioned, for example, by grabbing and pulling on the deployment stop panel 52, 62 and/or wing panel 50, 60.

Figure 6:
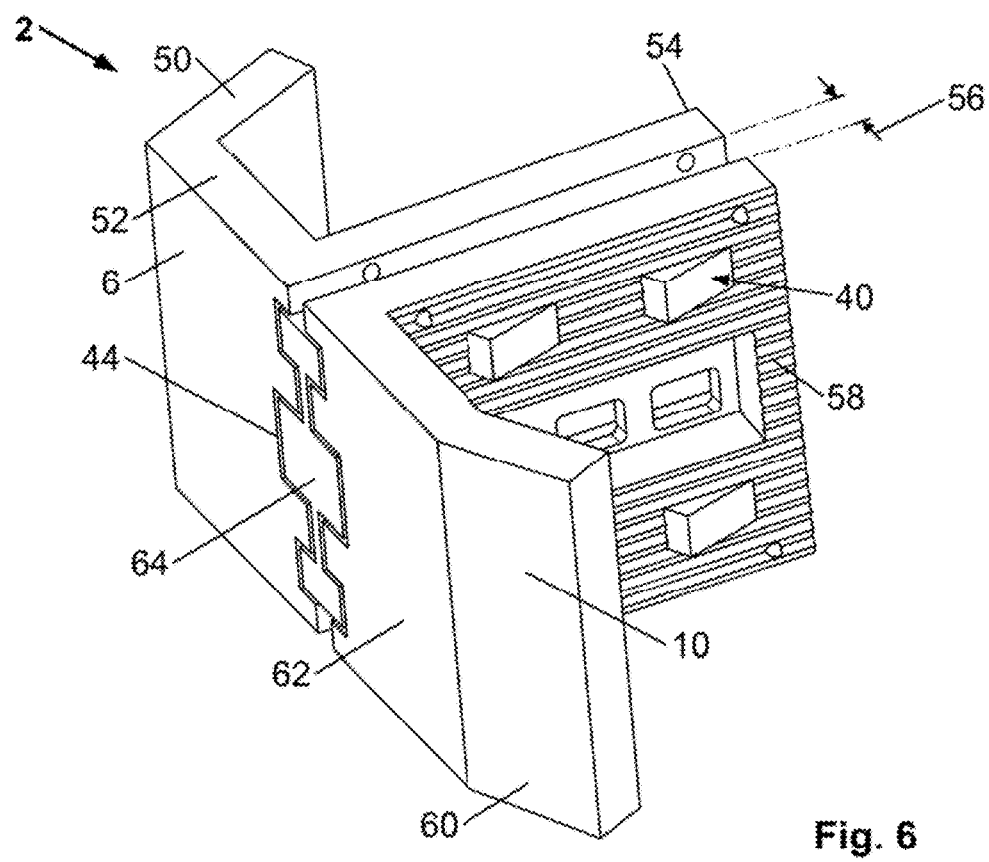
Figure 7:
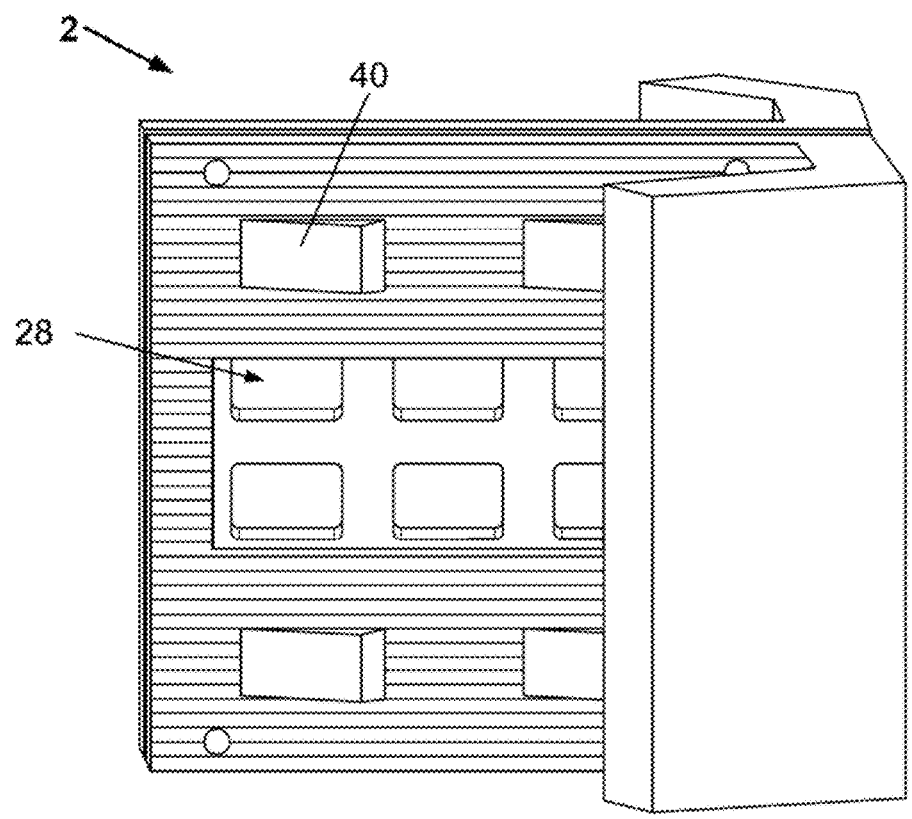

The top plate 6 and/or bottom plate 10 can have surface texturing, for example coring or gripping teeth on the outward-facing surface of the inner panels. The top and/or bottom plates 6, 10 can have ramps 22 and/or slots 46 and tabs 40. The ramps 22 can be on the inward-facing surfaces of the tabs 40. The tabs 40 can be partially bendable away from the plane of the inner panel. For example, as shown in FIG. 6, when the wedges 18 of the middle plate 8 are received by the ramps 22 of the inner panels, the wedges can push the tabs outwardly to extend from the plane of the inner panels 54, 58. During use, the extended tabs 40 can interference fit against the surrounding tissue (e.g., bone).

The top plate 6 and/or bottom plate 10 can have a stop seat 44 formed into the top and/or bottom plate 6, 10 along the outer surface of the deployment stop panels 52, 62. The stop seat 44 can be recessed into the deployment stop panels 52, 62. The stop seat 44 can be configured to receive a middle stop plate 64 on the middle plate 8. As shown in FIG. 6, when the middle plate 8 is fully inserted between the top plate 6 and the bottom plate 10, the middle stop plate 64 can lie flush in the stop seat 44.

The top and/or bottom plates 6, 10 can have grooves formed along the inner-surface of the inner panels 54 extending to the top plates 6. The grooves can form slots 46 when the top plate 6 and bottom plate 10 are adjacent to each other.

The middle plate 8 can have one or more rails 42. The rails 42 can be on opposite sides of the middle plate 8. The rails 42 can extend along the length of the middle plate 8.

The rails 42 can be configured to insert and slide through the slots 46 formed in the top and/or bottom plates 6, 10. The leading edge of the rail 42 can be angled, for example to a point or angled but with a flat front surface (as shown).

The rails 42 can have one or more wedges 18. For example, each rail 42 can have two wedges 18 on the side of the rail 42 facing the top plate 6 and two wedges 18 on the side of the rail 42 facing the bottom plate 10. The rails 42 can be spaced longitudinally along the rail.

The middle plate 8 can have one or more ingrowth channels 28. For example, the ingrowth channels 28 on the middle plate 8 can be arranged in a grid of two by three ingrowth channels 28. The ingrowth channels 28 can be located between opposing rails 42.

The middle plate 8 can be inserted between the top and bottom plates 6, 10. The middle plate 8 can be inserted along the length of the space between the top inner panel 54 and bottom inner panel 58 until the middle plate 8 stop interference fits against the stop seat 44. The top-bottom plate gap 56 can expand, for example up to about 100% or, more narrowly, up to about 50% from the contracted top-bottom plate gap 56.

Figure 8:
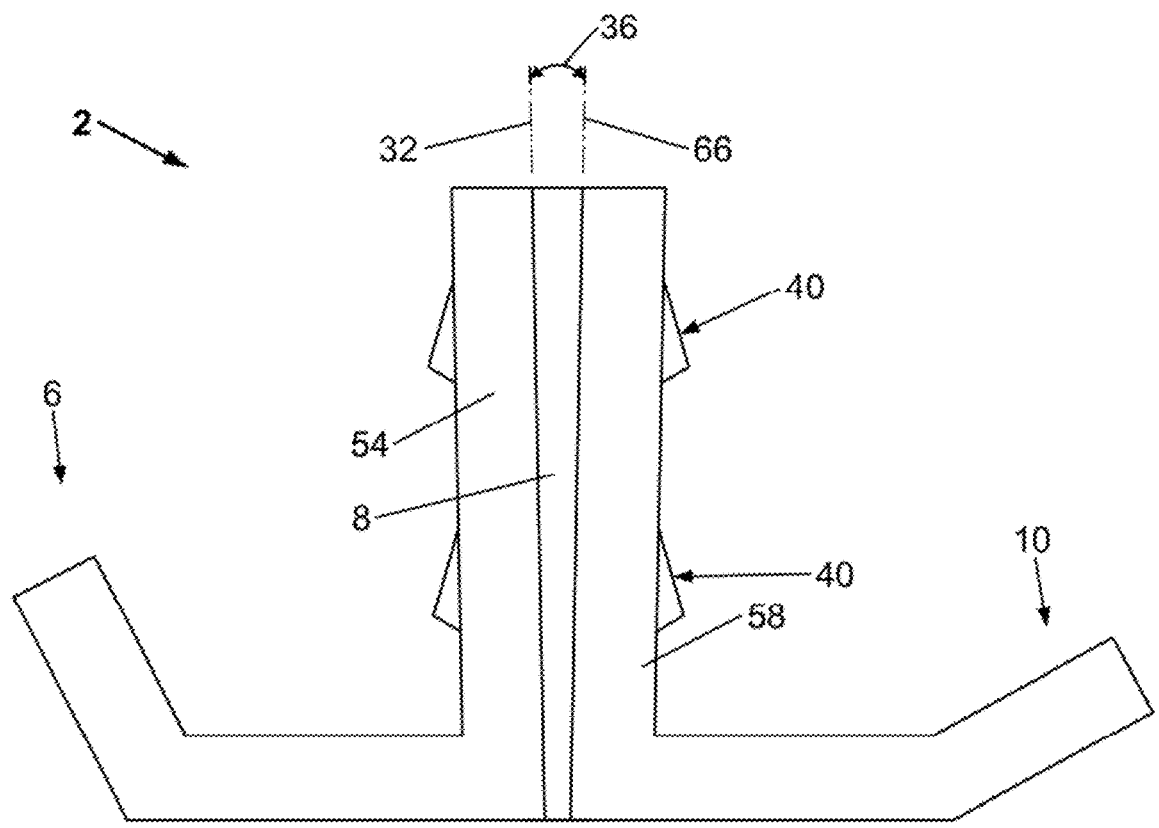

FIG. 8 illustrates that the tabs 40 can be pushed outward by the wedges and/or the top 6 and bottom plates 10 can have ports in place of the tabs 40. The wedges from the middle plate 8 can extend into or out of the outer side of the ports (accordingly, the wedges 18 would be the tabs 40 as labeled in FIG. 8).

The inner surface of the top inner panel 54 and the inner surface of the bottom inner panel 58 can form substantially equal device expansion angles 36 whether the device 2 is in an expanded (i.e., top and bottom plates apart) or contracted (i.e., top and bottom plates together) configuration.

The device 2 can have no pins or pin slots.

Figure 9:
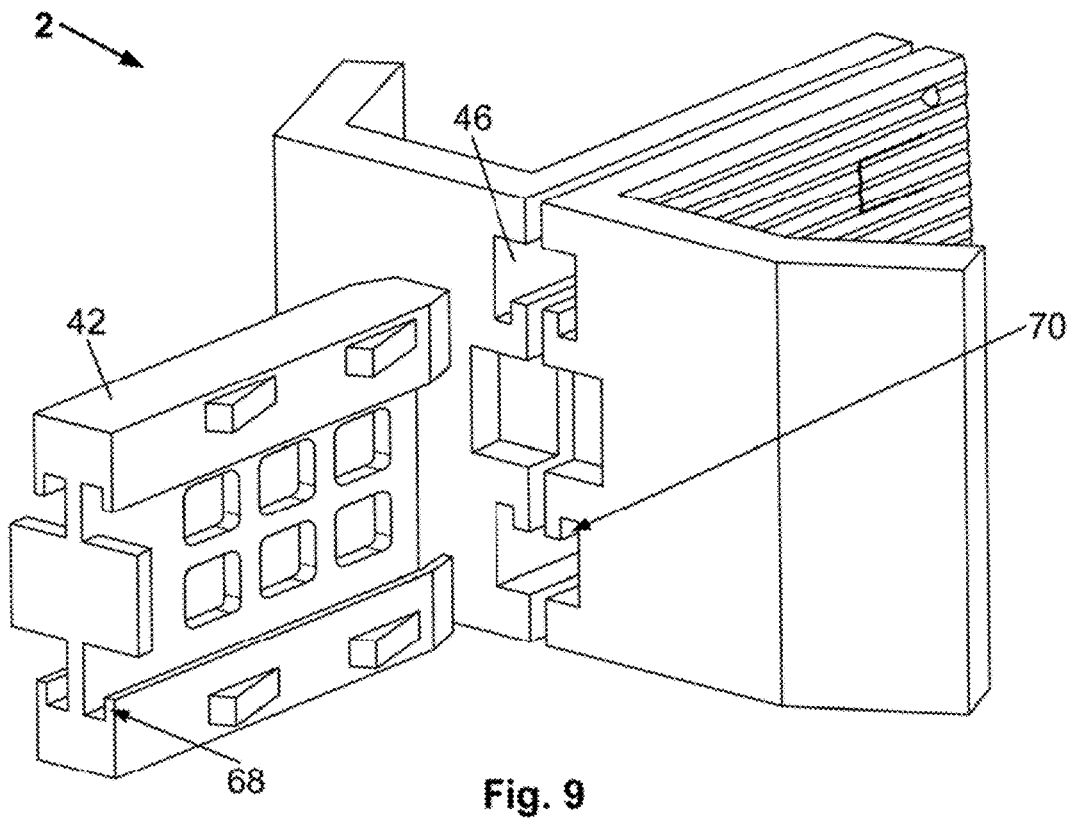
FIG. 9 illustrates a partially unassembled variation of the device.

FIG. 9 illustrates that the rails 42 on the middle plate 8 can have one or more rail extensions 68. For example, each rail 42 can have inwardly extending rail extensions 68 along the length of the rails 42 on one or both sides of the middle plate 8 facing the inner panels. The slots 46 can have slot extensions 70. For example, each slot 46 can have a slot extension 70 corresponding to the rail extensions 68 on the middle plate 8. The slots 46 can be t-slots. The rail extensions 68 can be configured to be slidably received by the slot extensions 70.

Figure 10:
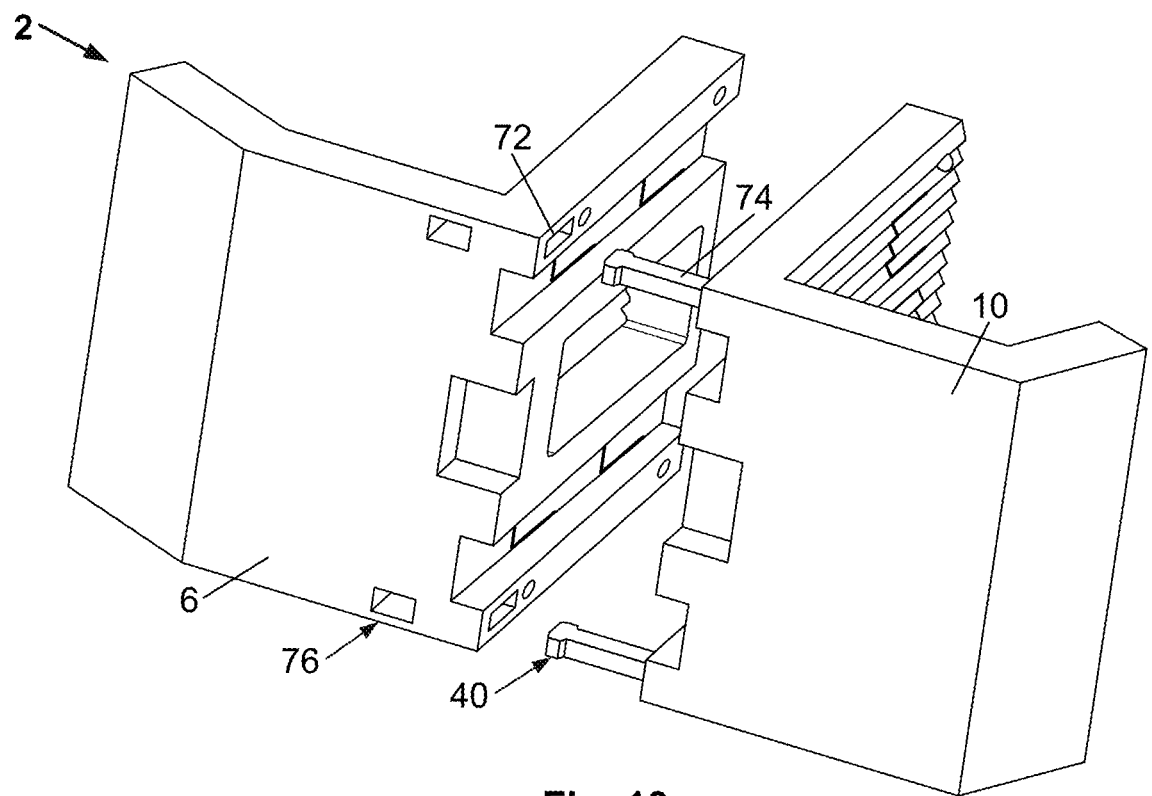
FIGS. 10 and 11 illustrate variations of the top and bottom plates of the device in unassembled and assembled configurations, respectively.
Figure 11:
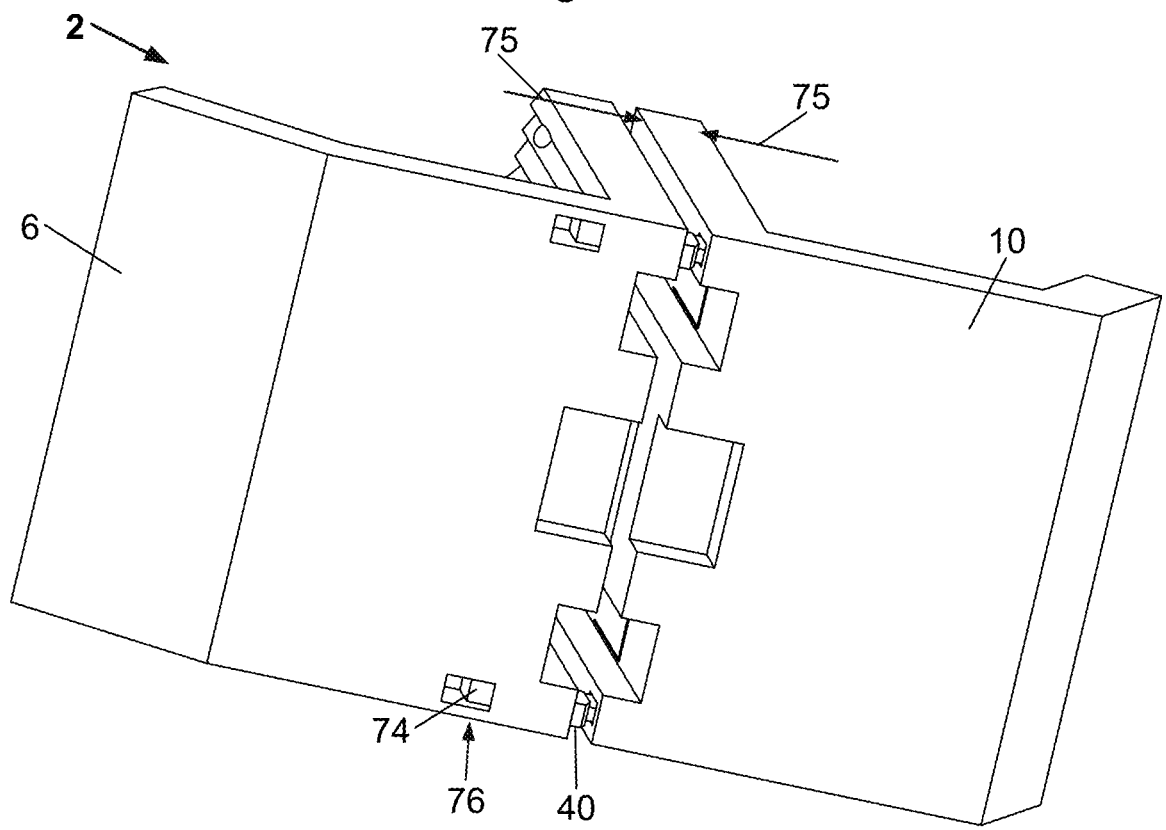
Figure 12:
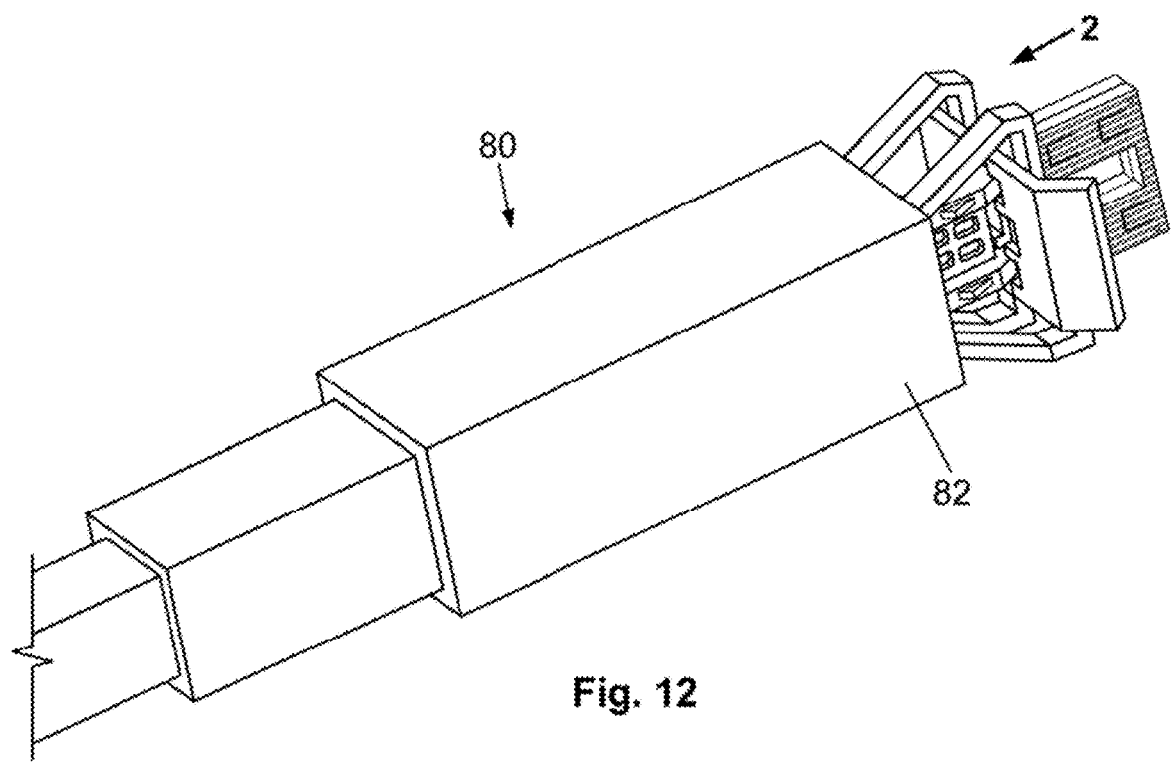
FIGS. 12 through 17 illustrate various views of the device of FIGS. 4 through 8 on a variation of a deployment tool.
Figure 13:
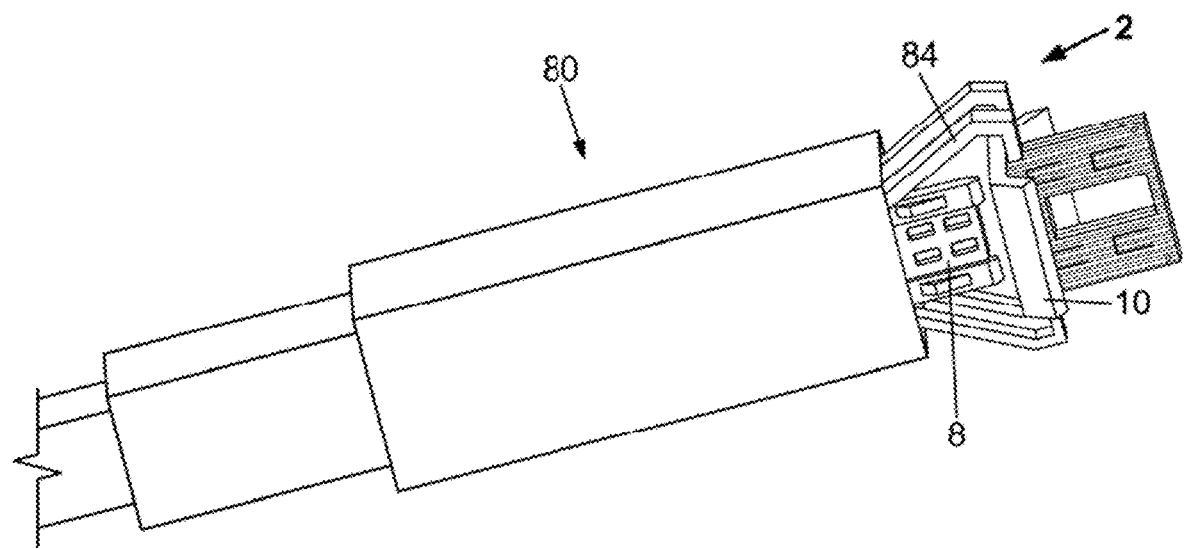
Figure 14:
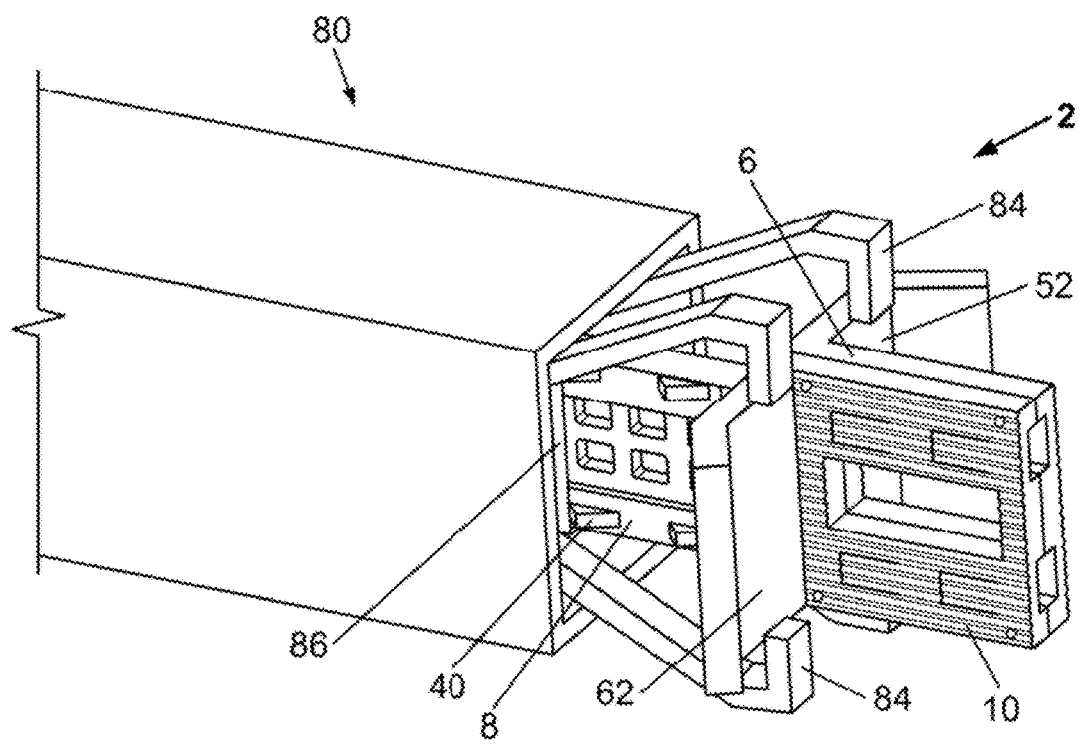
Figure 15:
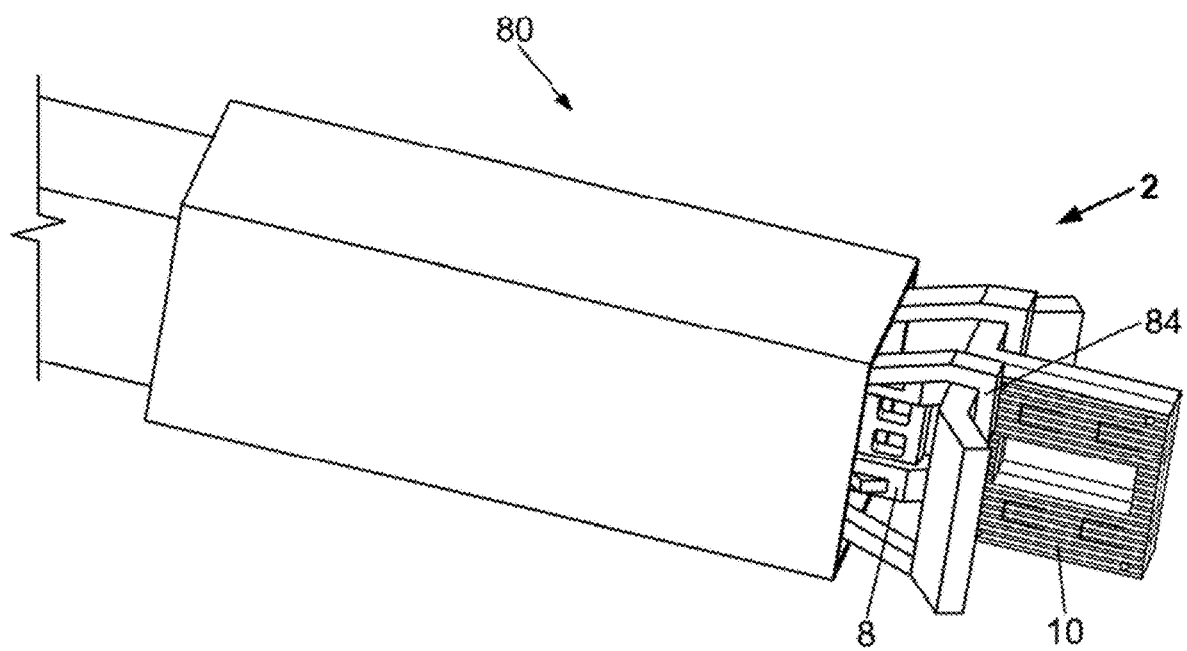
Figure 16:
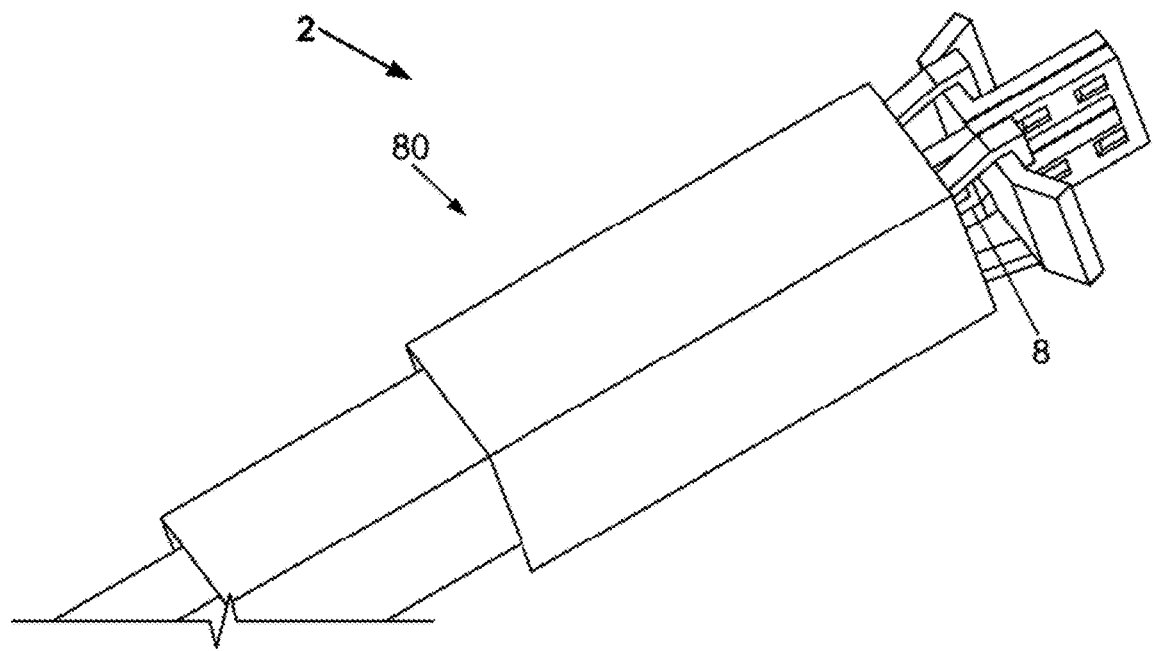

FIGS. 10 and 11 illustrate that the bottom plate 10 (as shown) and/or top plate 6 can have one or more tabs 40 extending in the direction of the top plate 6. The tabs 40 can extend from the deployment stop panels, in the plane of the deployment stop panels, pointed toward the opposing deployment stop panel. The tabs 40 can have tab ends 74 at the termini of the tabs 40. The tab ends 74 can have a locking feature, such as a flared end, brads, and expanded radius, or combinations thereof.

The top plate 6 can have one or more tab slots 72, corresponding to the positions, shapes, and sizes of the tabs 40. The tab slots 72 can be configured to receive the tabs 40. The tab slots 72 can have tab windows 76. The tab windows 76 can be configured to receive the tab ends 74, for example the locking feature of the tab ends 74. The tab windows 76 can be open to the surface of the corresponding panel in which the tab end 74 is located.

When the top plate 6 and bottom plate 10 are pressed toward each other, as shown by arrows 75 in FIG. 11, the tabs can be slidably received by the tab slots 72. The tab ends 74 can releasably lock into the tab windows 76. The tab windows 76 can be visually inspected to insure the tab end 74 is present, for example, as an indicator that the bottom plate 10 is fully engaged with, and fixedly attached to, the top plate 6.

FIGS. 12 through 16 illustrate that the device 2 can be removably attached to a deployment tool 80. The deployment tool 80 can provide a proximally retracting force (a "pull" deployment) or distally extending force (a "push" deployment) against the device 2 to expand and/or lock the device 2 depending on the design of the device 2 and the deployment tool 80.

The deployment tool 80 can have a deployment tool case 82. The deployment tool 80 can have grasping fingers 84 extending from the distal end of the deployment tool case 82. The grasping fingers 84 can be extended distally away from the deployment tool case 82, radially expanding from the other grasping fingers 84 and releasing the device 2. The grasping fingers 84 can be retracted proximally toward the distal end of the deployment tool case 82, radially contracting toward the other grasping fingers 84 and compressing against and holding the device 2.

Two grasping fingers 84 can releasably attach on opposite sides of the top plate 6, for example against the surface of the top deployment stop panel 52 facing the top inner panel. Two grasping fingers 84 can releasably attach on opposite sides of the bottom plate 10, for example against the surface of the bottom deployment stop panel 62 facing the bottom inner panel. The middle plate 8 can be aligned with the slots 46.

Figure 17:
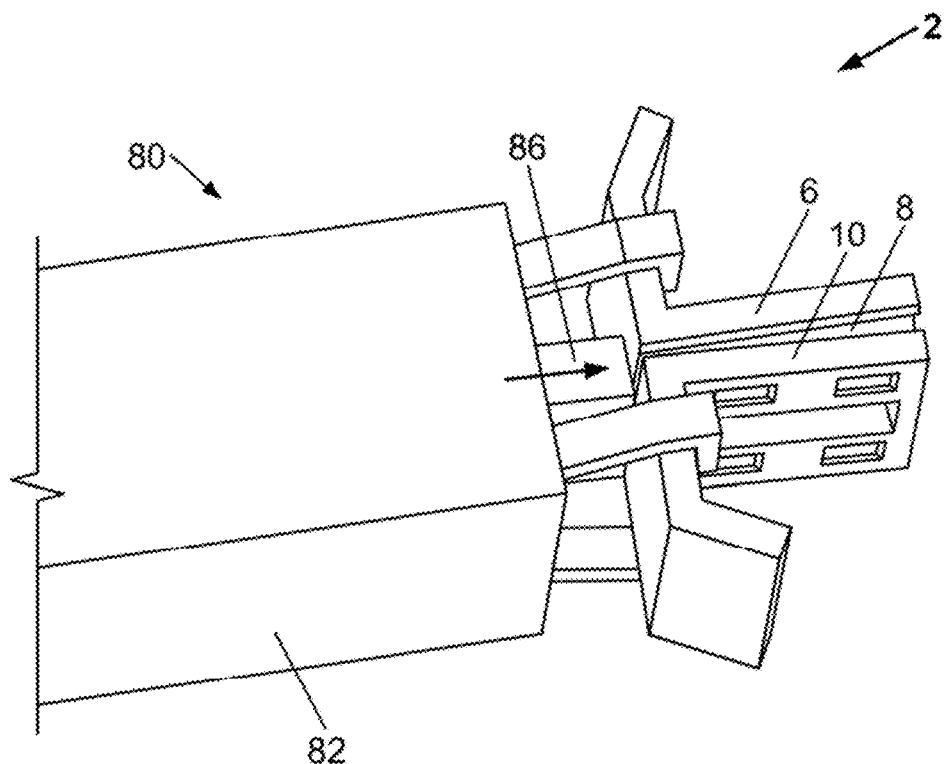

FIG. 17 illustrates that the deployment tool 80 can have an anvil 86. The anvil 86 can hold the middle plate 8 in place, which can transmit the force to the top 6 and bottom plates 10, holding the top 6 and bottom plates 10 in compression against the grasping fingers 42, as shown in FIGS. 12 through 16. Once the device 2 is placed into a target site (e.g., within a facet joint), the anvil 86 can be translated, as shown by arrow, to force the middle plate 8 between the top plate 6 and the bottom plate 10. The device 2 can be expanded. The tabs 40 and/or wedges 18 can then interference fit to prevent the middle plate 8 from retreating and the middle plate 8 can be fixedly attached to the top 6 and bottom plates 10. The grasping fingers 42 can be extended from the deployment tool case 82, radially expand away from one another, and release the device 2. The anvil 86 can be withdrawn into the deployment tool case 82.

Figure 18A:
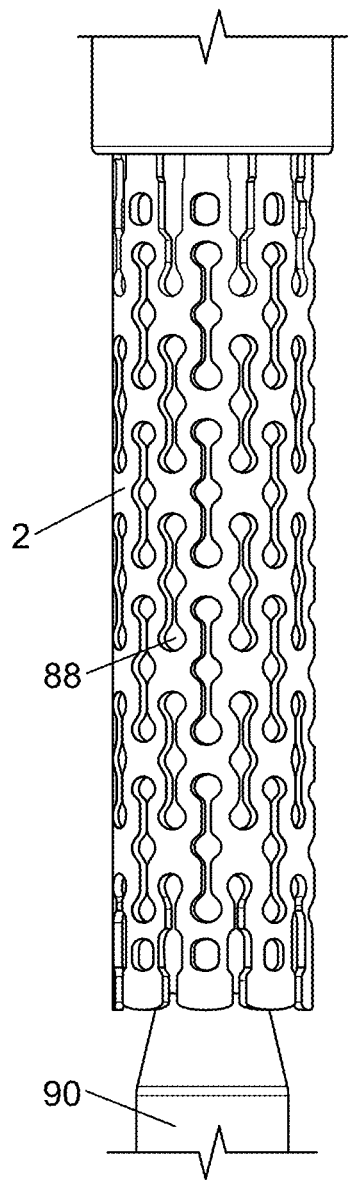
FIG. 18a illustrates a variation of the device in a contracted configuration.
Figure 18B:
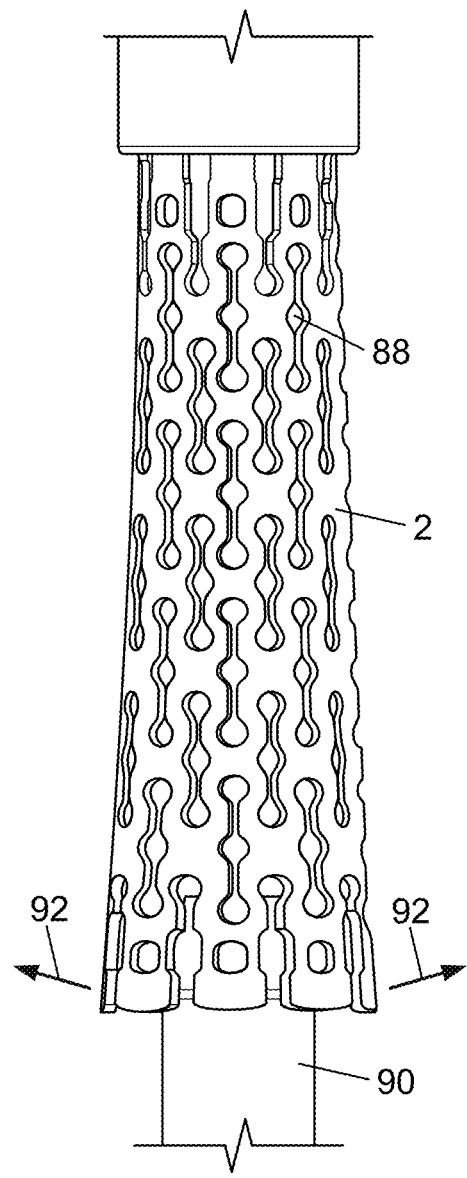
FIG. 18b illustrates the device of FIG. 18a in an expanded configuration.

FIGS. 18a and 18b illustrate that the device 2 can have cells 88 or pores. The cells 88 can be open when the device 2 is in a contracted configuration and/or open when the device 2 is in an expanded configuration so material can pass through the cells 88 to an inner longitudinal channel or lumen inside of the device 2, and/or to the opposite side of the device 2. For example, bone or other tissue growth can occur through the cells 88. The bone growth can pass through and encompass the device 2.

The device 2 can have a round or circular transverse cross-section. The device 2 can be ductile or deformable. The device 2 can be resilient.

FIG. 18a illustrates the device 2 can be loaded on a mandrel or deployment tool 90 in a contracted configuration. FIG. 18b illustrates that a first end of the device 2 can be radially expanded as shown by arrows 92 by the mandrel or other deployment tool 90 while the second end of the device 2 can remain contracted.

Figure 19A:
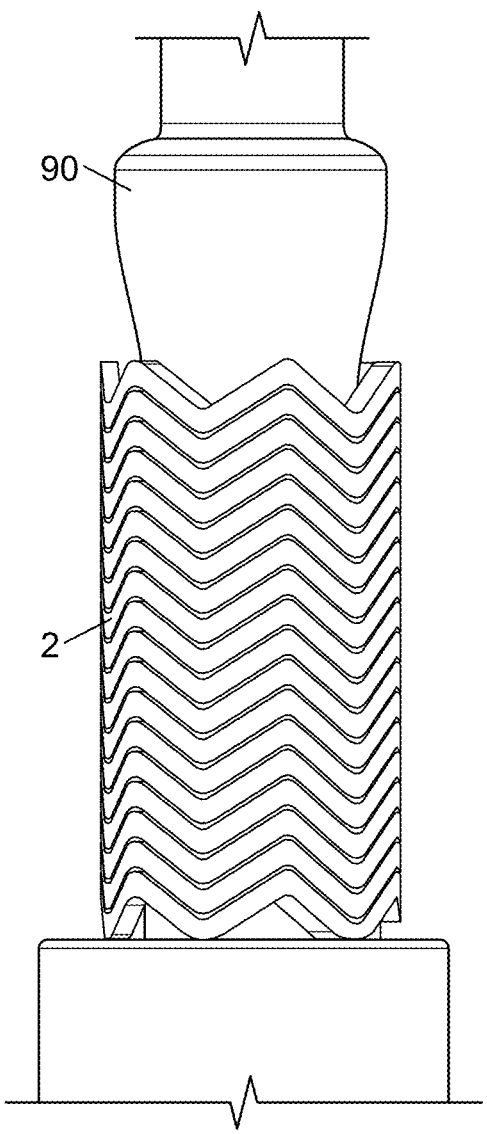
FIG. 19a illustrates a variation of the device in a contracted configuration.
Figure 19B:
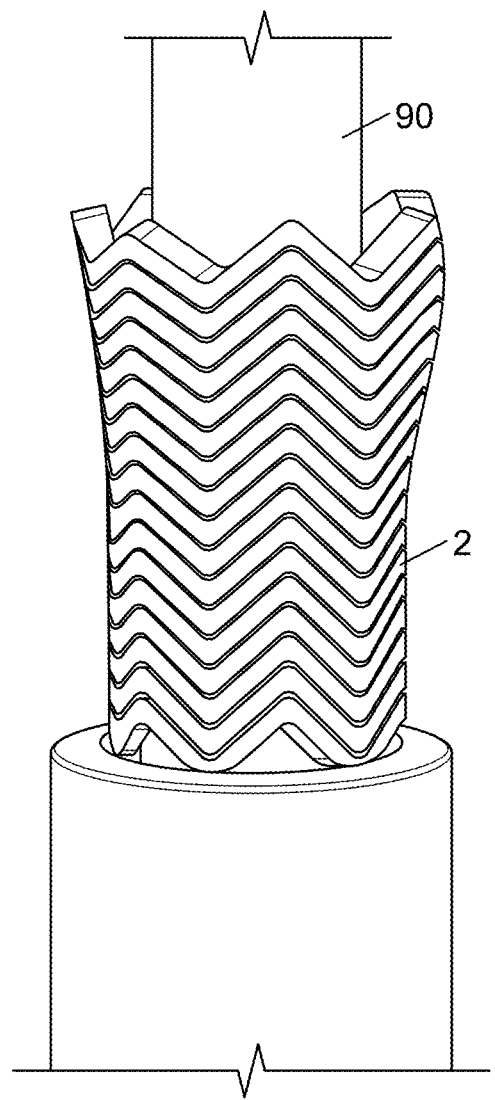
FIG. 19b illustrates the device of FIG. 19a in an expanded configuration.

FIGS. 19a and 19b illustrate that the device 2 can have insubstantial pores or cells 88. For example, substantially no material can flow or otherwise pass through the cells 88 or pores of the device 2.

FIG. 20 illustrates that the device 2 can have a first longitudinal end and a second longitudinal end along a longitudinal axis 4. The device 2 can have a bottom 10 or base plate (bottom 10 and base plate are used interchangeably) and a top plate 6. The base or bottom plate 10 and top plate 6 can be or have plates, panels, struts (e.g., legs), ports, cells, and combinations thereof. The base plate 10 and top plate 6 can be configured to be slidably attachable to the other. For example, the base (or top) plate 6, 10 can have one or more stability bars 102. The top (or base) plate 6, 10 can have one or more stability grooves 128. The stability bars 102 can be configured to be slidably attachable to the stability grooves 128.

The slidable attachment of the top and base plates 6, 10 can permit the base 10 to move radially (with respect to the longitudinal axis 4) relative to the top 6 and vice versa.

The top plate 6 can have a high-friction and/or low-friction texture extending radially away from the base 10. For example, the top plate 6 can have one or numerous rows of top teeth 118. The bottom plate 10 can have a high-friction and/or low-friction texture extending radially away from the base plate 10. For example, the bottom plate 10 can have one or numerous rows of bottom teeth 104. The top teeth 118 and the bottom teeth 104.

The top plate 6 can have one or more side ports 114 and/or top ports 116. The base plate 10 can have one or more base ports 120 and/or side ports 114. The base ports 120, side ports 114, and/or top ports 116 can be ingrowth channels. The ports can be circular, square, triangular, oval, elongated in the longitudinal direction, elongated in the radial direction, or combinations thereof.

The top plate 6 can have a top chamfer 156. The base plate 10 can have a base chamfer. The chamfers can be atraumatic edges. The chamfers can extend along the perimeter of the base and/or top 6, 10.

The device 2 can have one, two or more wedges 18, for example a first side ramp 96 on a first longitudinal side of the base plate 10 and a second side ramp 108 on a second longitudinal side of the base plate 10. The side ramps 96, 108 can be configured to be slidably attachable to the base plate 10.

The ramps 96, 108 and top plate 6 can be brought within proximity of the base plate 10. The ramps 96, 108 can be slidably attached to the base plate 10. The ramps 96, 108 can have ramp second tongues and grooves 98. The base plate 10 can have one or more base tongues and grooves 106. The ramp second tongues and grooves 98 can be configured to slidably attach to the base tongues and grooves 106.

The ramps 96, 108 can be configured to be slidably attachable to the top plate 6. For example, the ramps 96, 108 can have ramp first tongues and grooves 100. The top plate 6 can have top tongues and grooves 284. The ramp first tongues and grooves 100 can slidably engage the top tongues and grooves 284. Groove 284 can comprise groove first side 284A, groove bottom 284B and groove second side 284C. There may further be surface 284D following from groove second side 284D. First side 284A may as illustrated coincide with the planar ramp surface 96A of ramp 96. Similarly, there may be another opposed groove having groove first side 284E, groove bottom 284F, groove second side 284G, and surface 284H. As illustrated, groove sides 284B and 284F may both be parallel with each other, groove sides 284C and 284G may both be parallel to the ramp surface and to groove sides 284A and 284E and may be coplanar with each other, and surfaces 284D and 284H may be parallel with each other.

The first tongues and grooves 100 can be at a ramp angle with respect to the second tongues and grooves 98. The ramp angle can be from about 15° to about 75°, more narrowly from about 30° to about 60°, for example about 45°.

One or more of the ramps can have a ramp locking plate port 110. The ramp locking plate ports 110 can each be configured to receive a ramp locking plate. The ramps can each have ramp ports, such as the threaded ramp ports 94. The threaded ramp ports 94 can pass through the ramps, for example opening into the ramp locking plate port 110.

Figure 21:
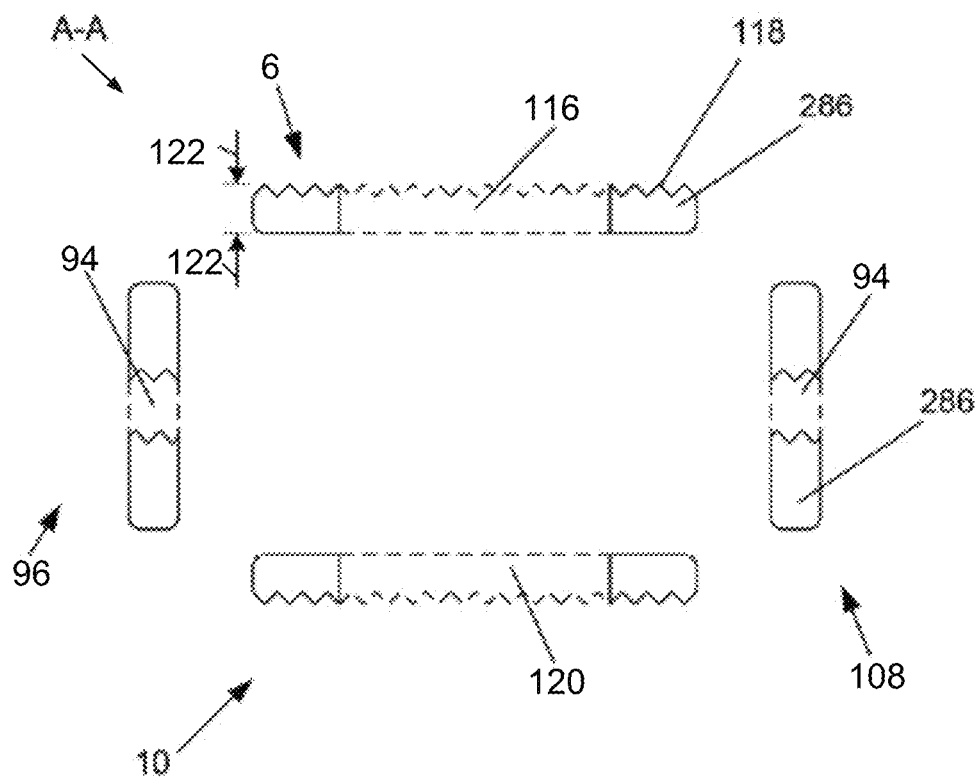
FIGS. 21 through 23 illustrate variations of cross-section A-A of FIG. 1.

FIG. 21 illustrates that each of the top 6, or base or bottom plates 10 can have a plate thickness 122. The plates can be thinned adjacent to some or all ports. The plate thickness 122 can be substantially constant along the length of the top or base 6, 10. The plate thickness 122 can be non-constant, for example along the length and/or width of the top port 116 or base port 120 and the top teeth 118 or base teeth. Each plate 286 of the first side ramp 96 and the second side ramp 108 can have a substantially constant plate thickness 122 along the height of the plate 286 save for the respective ramp ports.

Figure 22:
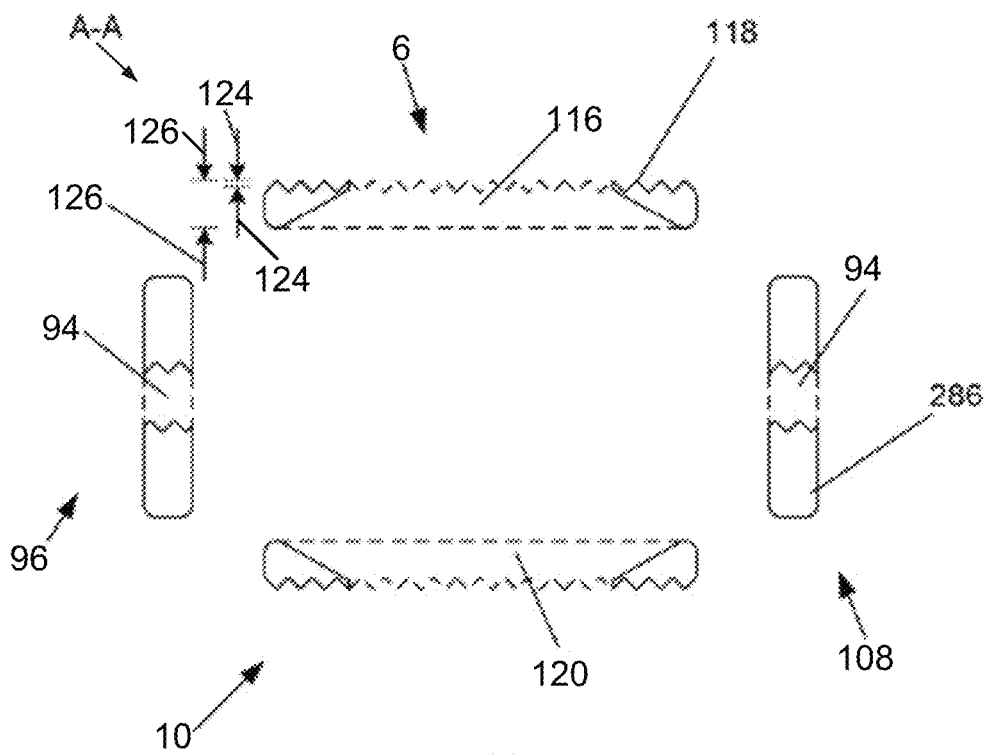

FIG. 22 illustrates that the top 6 and/or bottom plates 10 can thin as the plate 286 nears the port. For example, the plate 286 can have a maximum plate thickness 126 and a minimum plate thickness 124. The maximum plate thickness 126 and minimum plate thickness 124 can be measured with or without accounting for the change in thickness due to the teeth 118. The minimum plate thickness 124 can be substantially less than the maximum plate thickness 126. The minimum plate thickness 124 can be substantially 0. The plate can slope outward (as shown), inward, or a combination of both (e.g., sloping inward and outward concurrently to form the rim of the port at a radius from the longitudinal axis between the radii of the outer and inner surfaces of the plate).

When the device 2 is in a deployed configuration in vivo, the device 2 can be partially or substantially filled with a liquid, gel, or solid (e.g., in small parts or granules) filler material, or combinations thereof, such as bone morphogenic powder or any other material disclosed herein or combinations thereof. The filler material can contact or be in near contact with the surrounding tissue near the edge of the ports, for example where the plate 286 is thinned.

Figure 23:
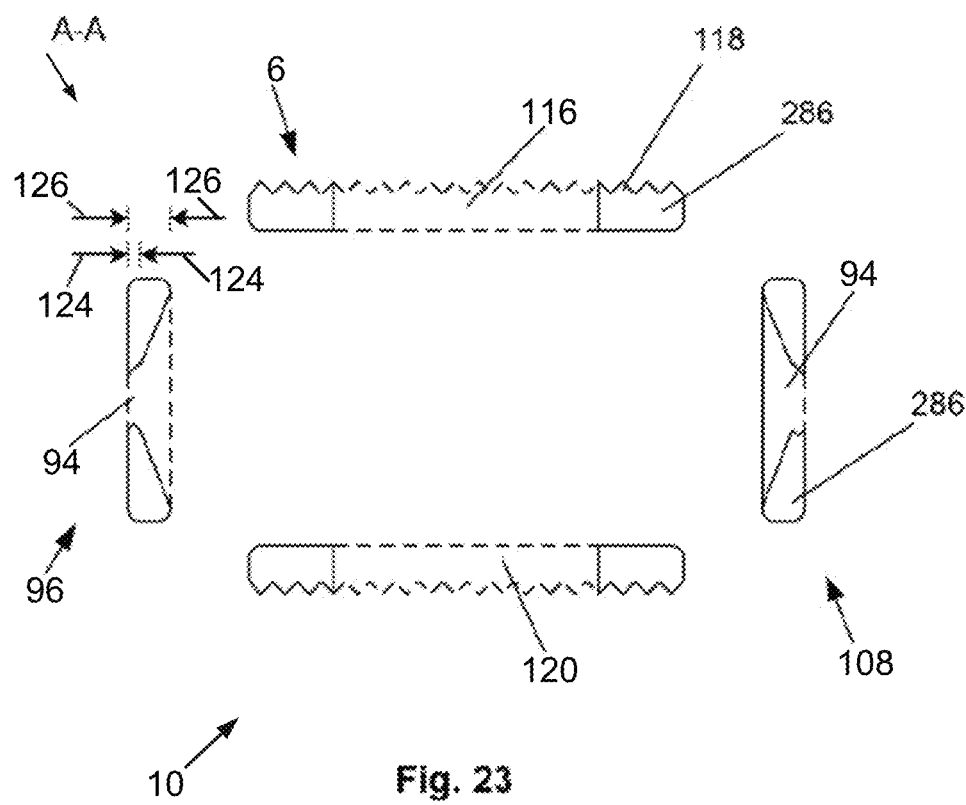

FIG. 23 illustrates that the plates 286 of the first side ramp 96 and/or the second side ramp 108 can thin as the plate 286 nears the threaded ramp port(s) 94. The minimum plate thickness 124 can be substantially less than the maximum plate thickness 126. The minimum plate thickness 124 can be substantially 0. The plate 286 can slope outward (as shown), inward, or a combination of both (e.g., sloping inward and outward concurrently to form the rim of the port at a radius from the longitudinal axis between the radii of the outer and inner surfaces of the plate 286).

Figures 24, 25:
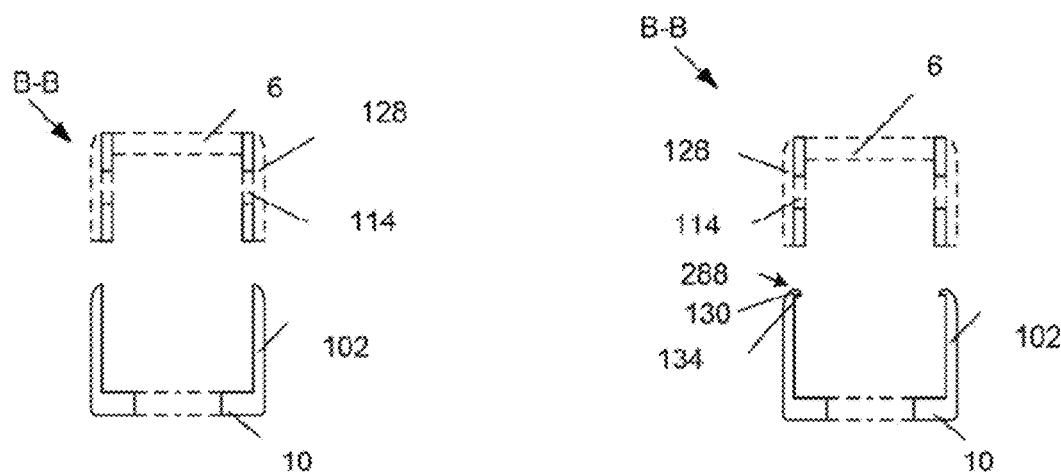
FIGS. 24 and 25 illustrate variations of cross-section B-B of FIG. 20.

FIG. 24 illustrates that the stability bars 102 can be configured to slide into the stability groove 128 when the top 6 and base plates 10 intersect. The radially inner surface of the stability bar 102 can be substantially the same or a greater radius from the longitudinal axis of the expandable support device 2 as the radius of the radially outer surface of the top plate 6 adjacent to the side port 114 (i.e., within the stability groove 128). The stability bar 102 can be configured to not directly attach to the top plate 6 when the top is translated into the base plate 10, or the stability bars 102 can be configured to bias inward against and frictionally hold the top when the top plate 6 is translated into the base plate 10.

FIG. 25 illustrates that the stability bars 102 can have one or more latches 130 along the length of the stability bar 102, for example at the terminal end of the stability bars 102, as shown. The latch 102 can be configured to attach to the top plate 6. The latch 102 can protrude radially inward. The latch 102 can have a latch top 288 and a latch bottom 134.

The latch top 288 can be configured to allow the top to pass over the latch 130. For example, the latch top 288 can be rounded and configured to push radially outward and clear of the top plate 6 when the top is pressed down into the latch top 288. The latch bottom 134 can be configured to grasp or otherwise attach to the top when the top is translated to a particular location into the base plate 10.

The stability bars 102 can be configured to resiliently bend radially outward and/or inward.

Figure 26:
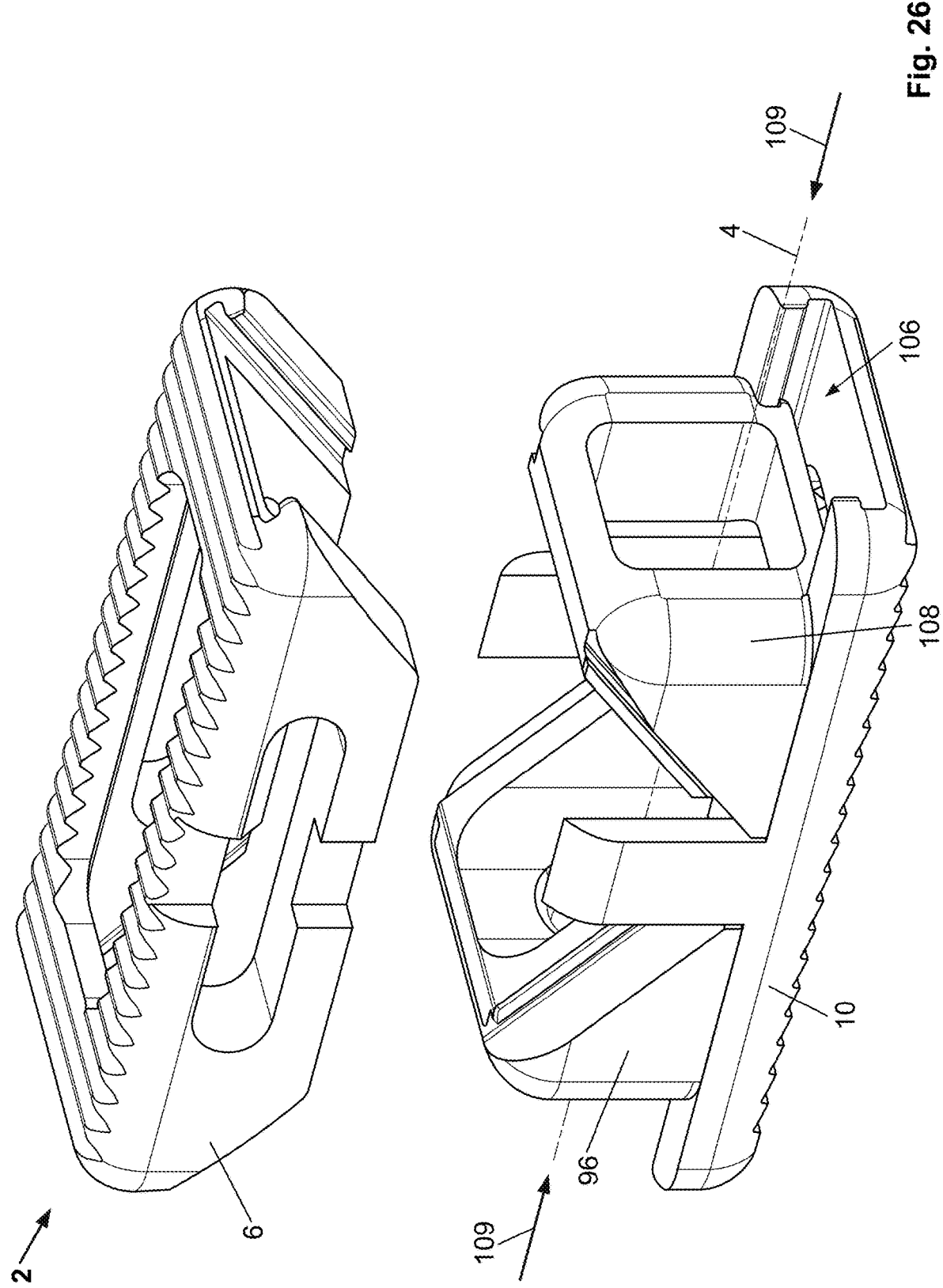
FIG. 26 illustrates the variation of the expandable support device of FIG. 20 with the ramps slidably attached to the base.

FIG. 26 illustrates that the ramps 96, 108 can be slidably attached, as shown by arrows 109, to the base plate 10 before the ramps 96, 108 are slidably attached to the top plate 6. The ramp second tongues and grooves 142, 144 can be slidably engaged with the base tongues and grooves 146, 148, as shown in FIGS. 31, 32 and 33.

Figure 27:
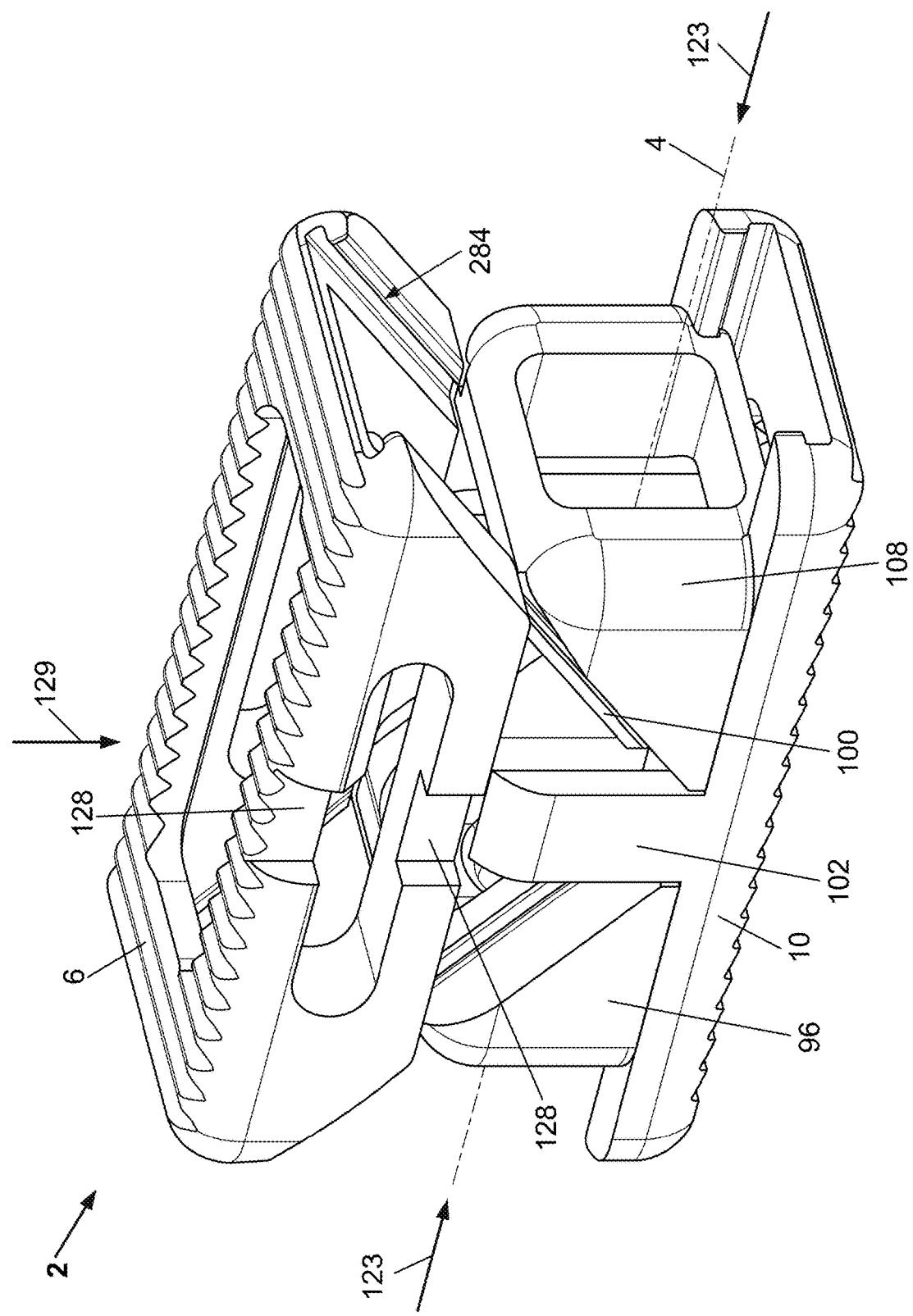
FIGS. 27 and 28 are perspective and side views, respectively, of the variation of the expandable support device of FIG. 26 with the top and ramps in pre-assembly positions.
Figure 28:
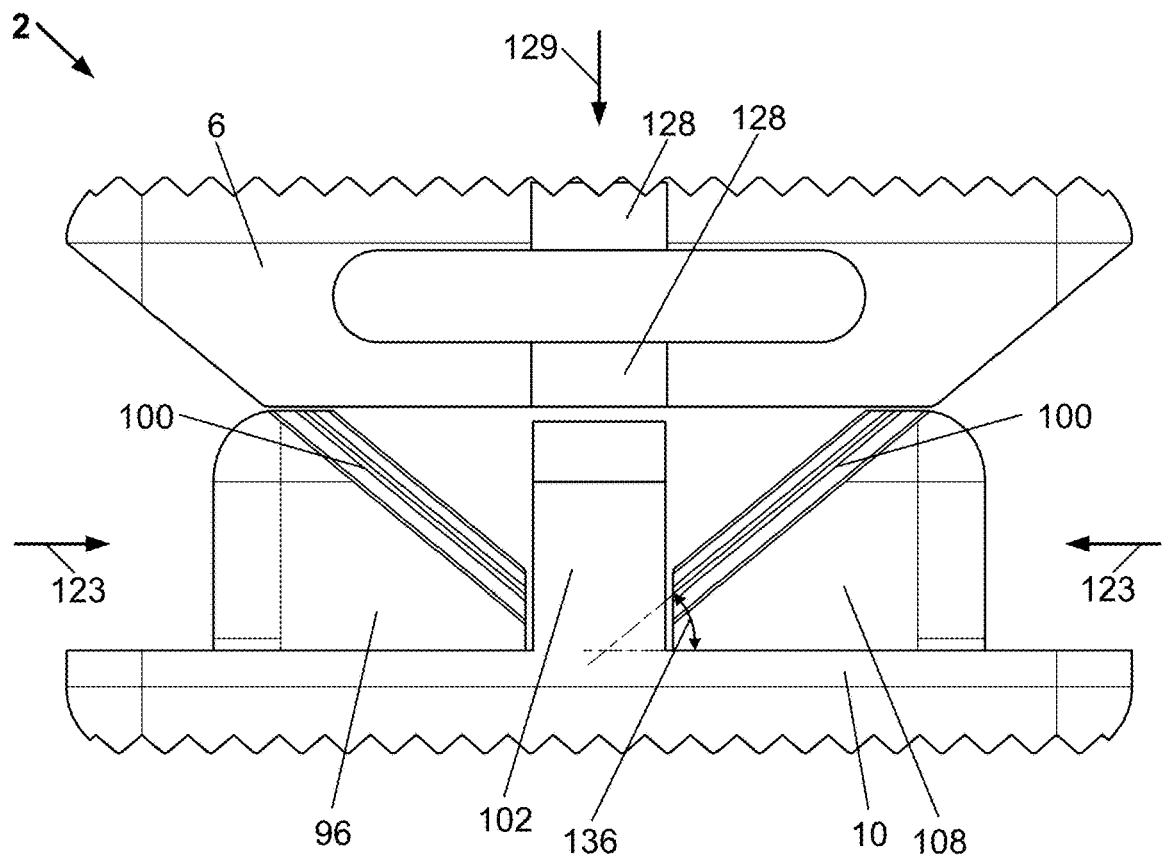

FIGS. 27 and 28 illustrate that the ramps 96, 108 can be positioned, as shown by arrows 123, so that one or both ramp first tongues and grooves 100 can be aligned to slidably engage the top tongues and grooves as the top plate 6 is translated toward the base plate 10, as shown by arrows. The stability bar 102 can be slid into the stability groove 128.

Figure 30:
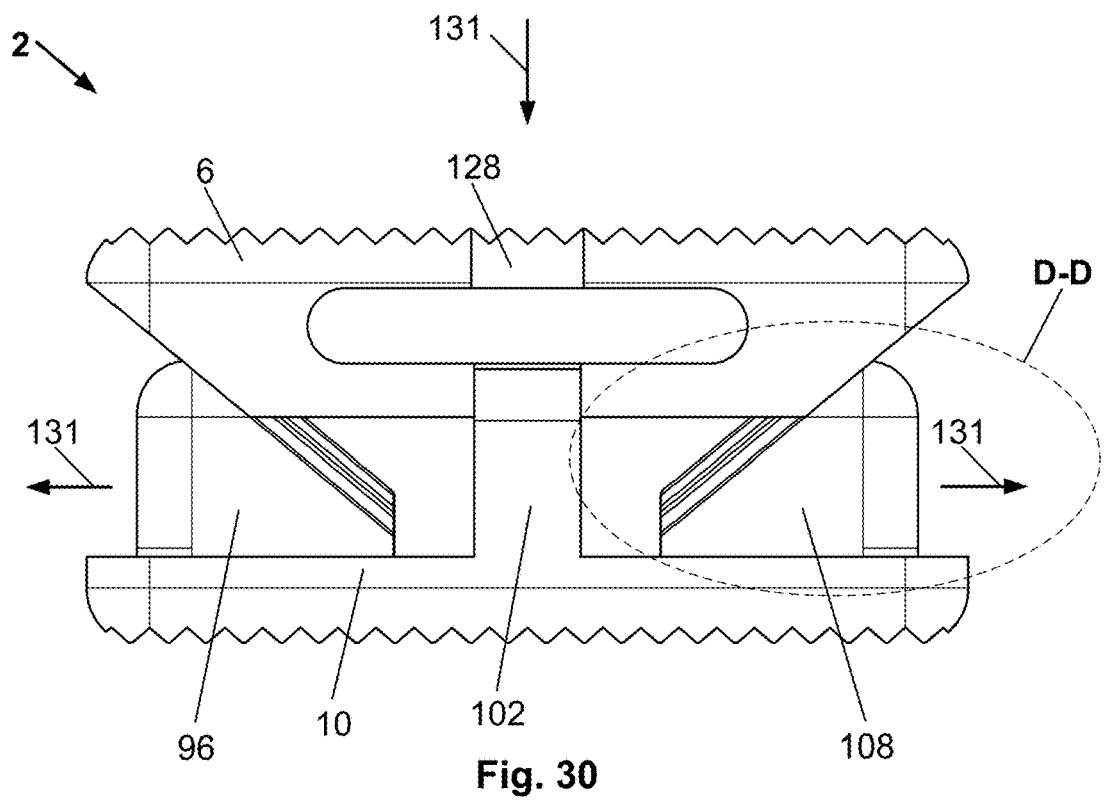
FIGS. 29, 30 and 31 are perspective, side and end views, respectively, of the variation of the device of FIG. 20 in an assembled configuration.
Figure 29:
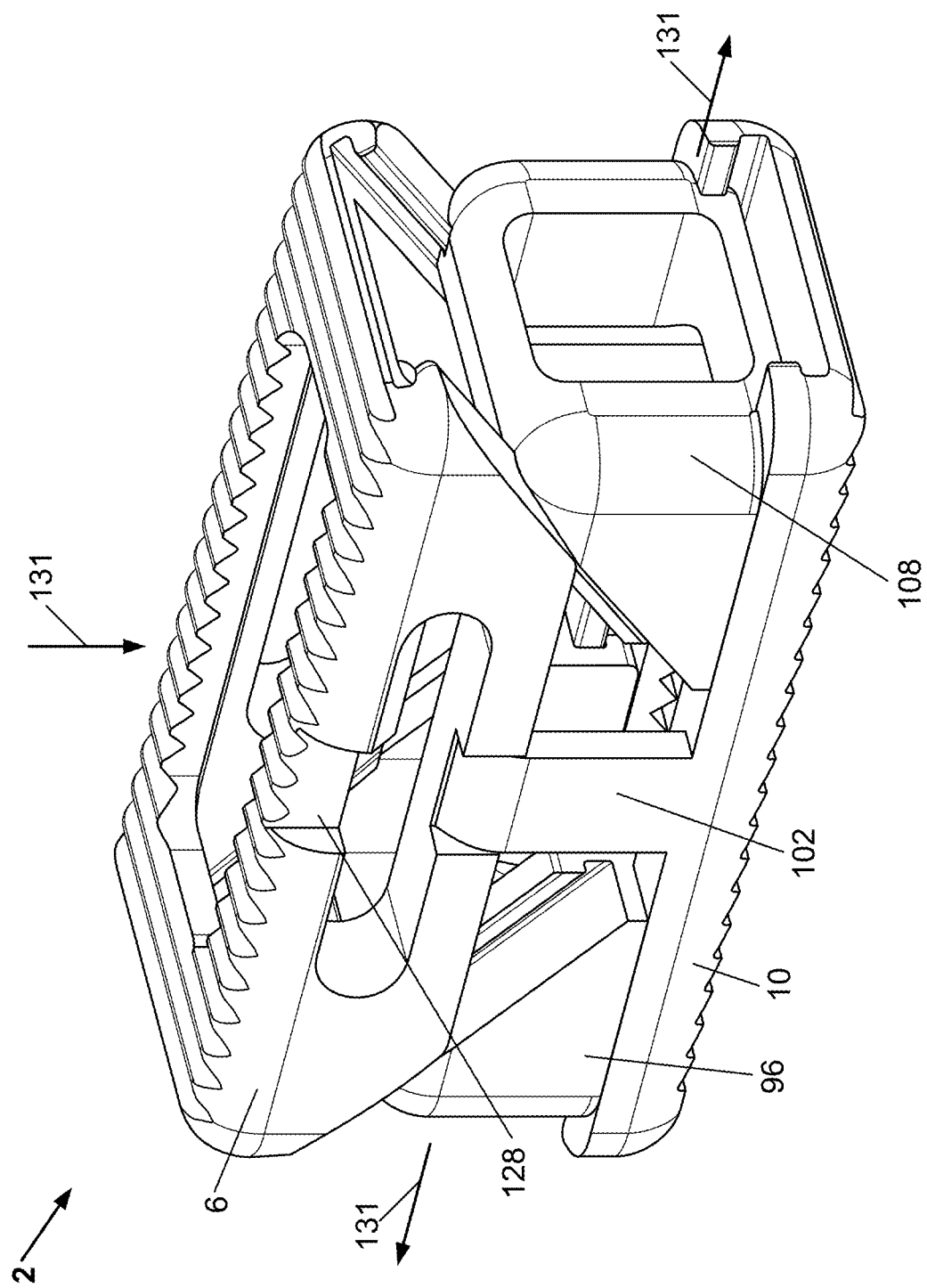
Figure 31:
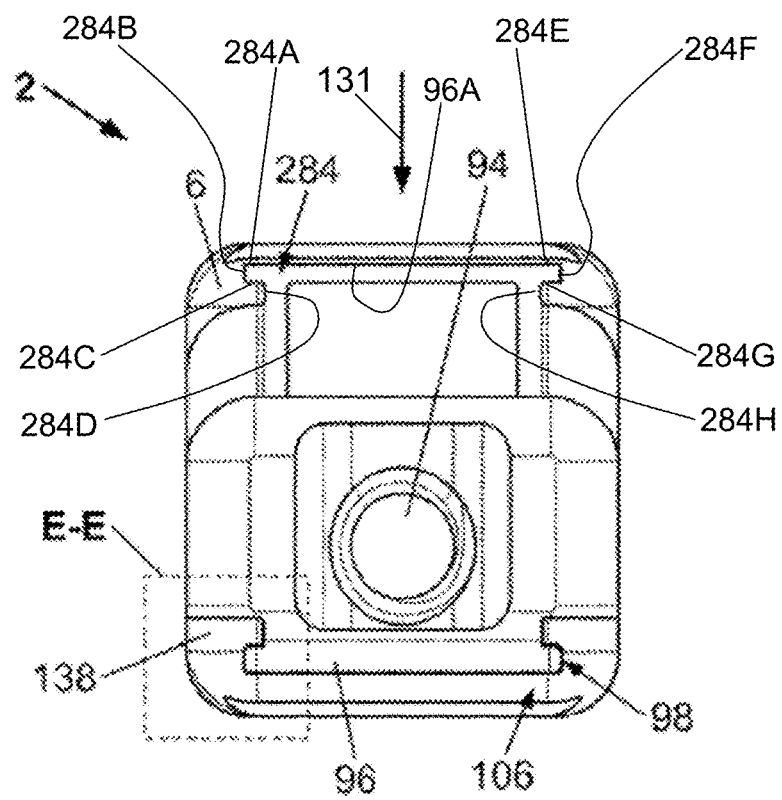

FIGS. 29 through 31 illustrate that as the top plate 6 is translated toward the base plate 10, as shown by arrows 131, the top plate 6 can slidably engage one or more of the ramps 96, 108. The first tongues and grooves can slidably engage the top tongues and grooves 284.

Figure 32:
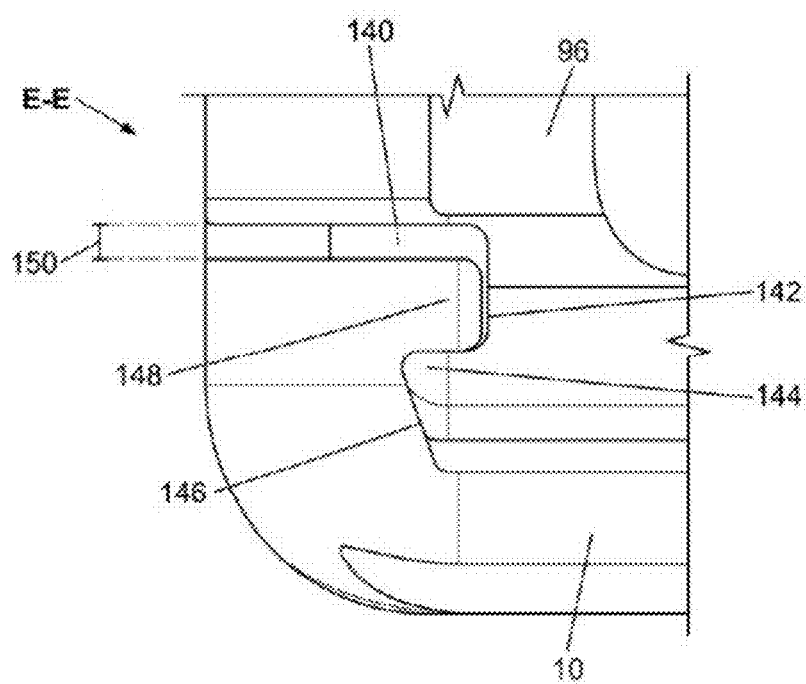
FIG. 32 is a variation of close-up section E-E of FIG. 31 in a first configuration.
Figure 33:
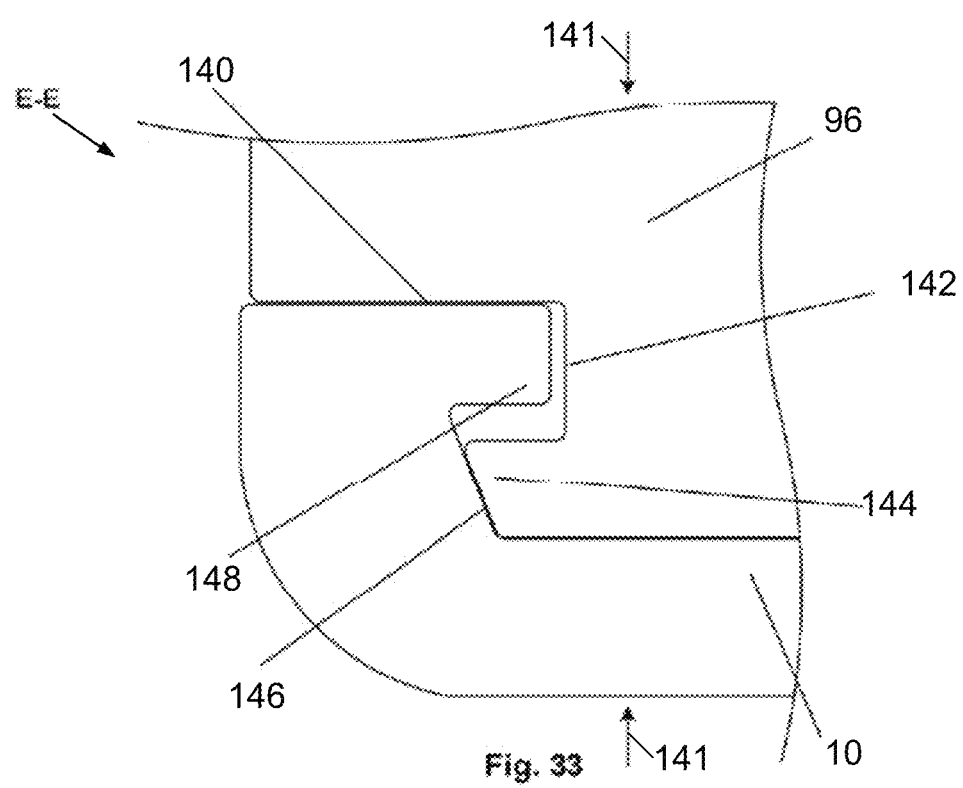
FIG. 33 is a variation of close-up section E-E of FIG. 31 in a second configuration.

FIG. 32 illustrates that there can be a substantial ramp gap 140 between the side ramp and the base plate 10, for example before the expandable support device 2 is completely deployed. The ramp gap 140 can have a ramp gap height 150. The ramp gap height 150 can vary, for example, from about 0 mm (0 in.) to about 4 mm (0.2 in.). The side ramps 96 can substantially slide along the base plate 10. For example, the ramp second tongue and groove 142, 144 can slide along the base tongue and groove 146, 148, separated by the ramp gap 140. Most or all of the friction in this configuration can be created by the ramp second tongue 144 in contact with the base tongue 148 and/or side of the base groove 146.

The wall of the base groove 146 can have an outwardly slanted configuration relative to the height of the wall of the base groove 146 from the bottom of the base plate 10.

FIG. 33 illustrates that the first side ramp 96 and the base 10 can be pressed into or otherwise translated toward each other as shown by arrows 141. For example, after implantation of the device 2, the surrounding tissue in the in vivo environment can naturally compress the device 2.

The ramp gap 140 can be substantially closed. The ramp gap height 150 can be substantially about 0. The side ramps 96 can be substantially friction fit along the base plate 10. For example, the friction in this configuration can be created along the top surface of substantially the entire base plate 10 including the top of the base tongue 148, and the bottom surface of substantially the entire side ramps 96.

As the side ramp 96 is pushed, as shown by arrows, toward the base plate 10, the ramp second tongues 144 can be pressed between the base grooves 146, for example, frictionally fitting the side ramps into the base plate 10. The base grooves 146 can be tapered, as shown, to force the ramp second tongues 144 to wedge fit or press fit into the base grooves 146 when the side ramp is pushed towards the base plate 10.

The side ramps 96 can have less friction with the base plate 10 in the configuration of the expandable support device 2 of FIG. 32 than in the configuration of the expandable support device 2 of FIG. 33.

Figure 34:
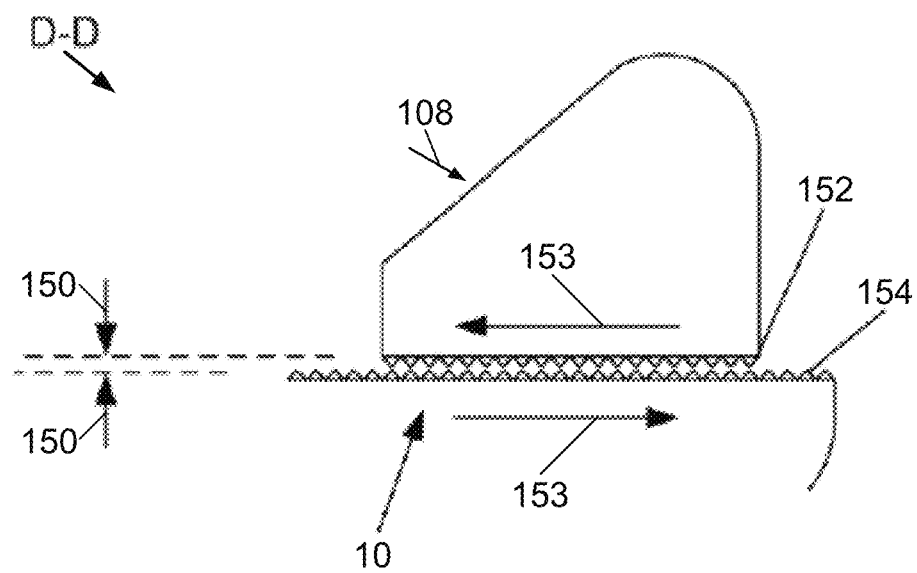
FIGS. 34 and 35 are a variation close-up section D-D of FIG. 30 in first and second configurations, respectively.

FIG. 34 illustrates that the second side ramp 108 (and/or the first side ramp 96, not shown) can have ramp bottom teeth 152 on the side of the second side ramp 108 (and/or first side ramp 96) facing the base plate 10. The ramp bottom teeth 152 can extend into the ramp gap. Either or both side ramps 108 can have teeth on any and/or all sides of the side ramp, for example the surfaces that contact the base plate 10 and the top plate 6. The top plate 6 can have additional teeth, not shown, along surfaces that contact the side ramps 108.

The ramp bottom teeth 152 and/or base interior teeth 154 can be unidirectionally or bidirectionally oriented (i.e., providing additional resistance against movement in one direction, or substantially the same resistance against movement in either direction).

As the side ramp 108 translates, as shown by arrows 153, with respect to the base plate 10, the ramp gap height 150 is substantially non-zero, as shown in FIGS. 32 and 34. When the ramp gap height 150 is substantially non-zero, the ramp bottom teeth 152 can slide over the base interior teeth 154.

Figure 35:
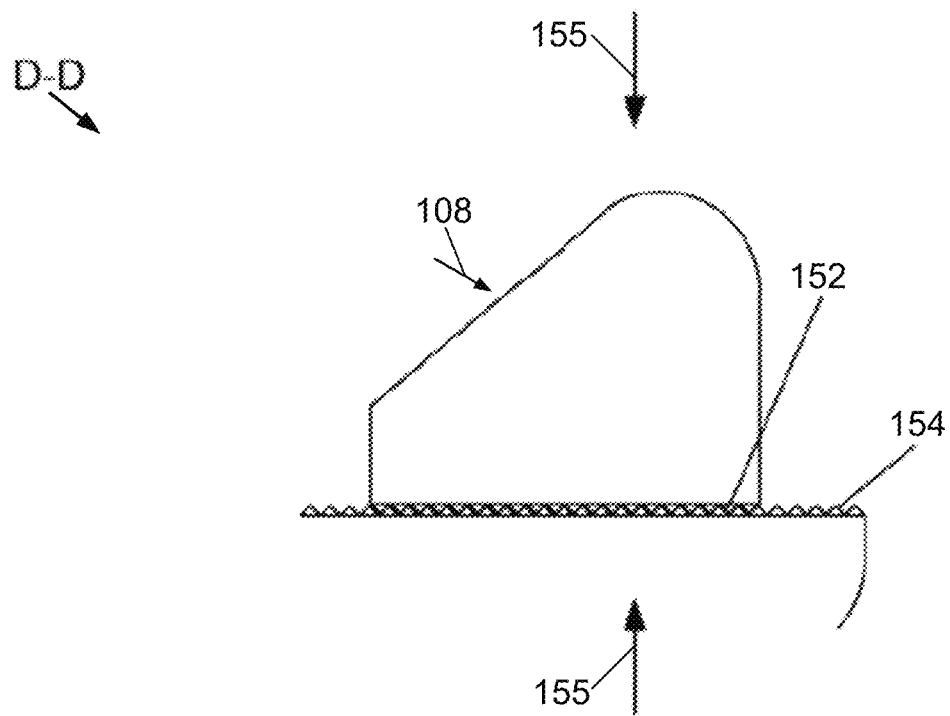

FIG. 35 illustrates that when the side ramp 108 and base plate 10 are pressed together, as shown by arrows 155, for example when deployed in vivo, the ramp gap height 150 can be minimized, for example approaching about 0 mm (0 in.). The ramp bottom teeth 152 can interlock with the base interior teeth 154. The interlocked ramp bottom teeth 152 and base interior teeth 154 can provide an interference fit or otherwise prevent or minimize the side ramp 108 translating relative to the base plate 10.

In place of, or in addition to, the ramp bottom teeth 152 and/or the base top teeth, the respective surfaces can have high friction surfaces, for example a textured (e.g., knurled) surface and/or coated with a high friction material. The respective surfaces can also be smooth, having no teeth or texturing.

The side ramp 108 can be pulled away from the base plate 10 by reducing the compressive force between the side ramp 108 and the base plate 10 and pulling or pushing the side ramp 108.

The side ramp 108 can have a belt and suspenders lock with the base plate 6.

Figure 36:
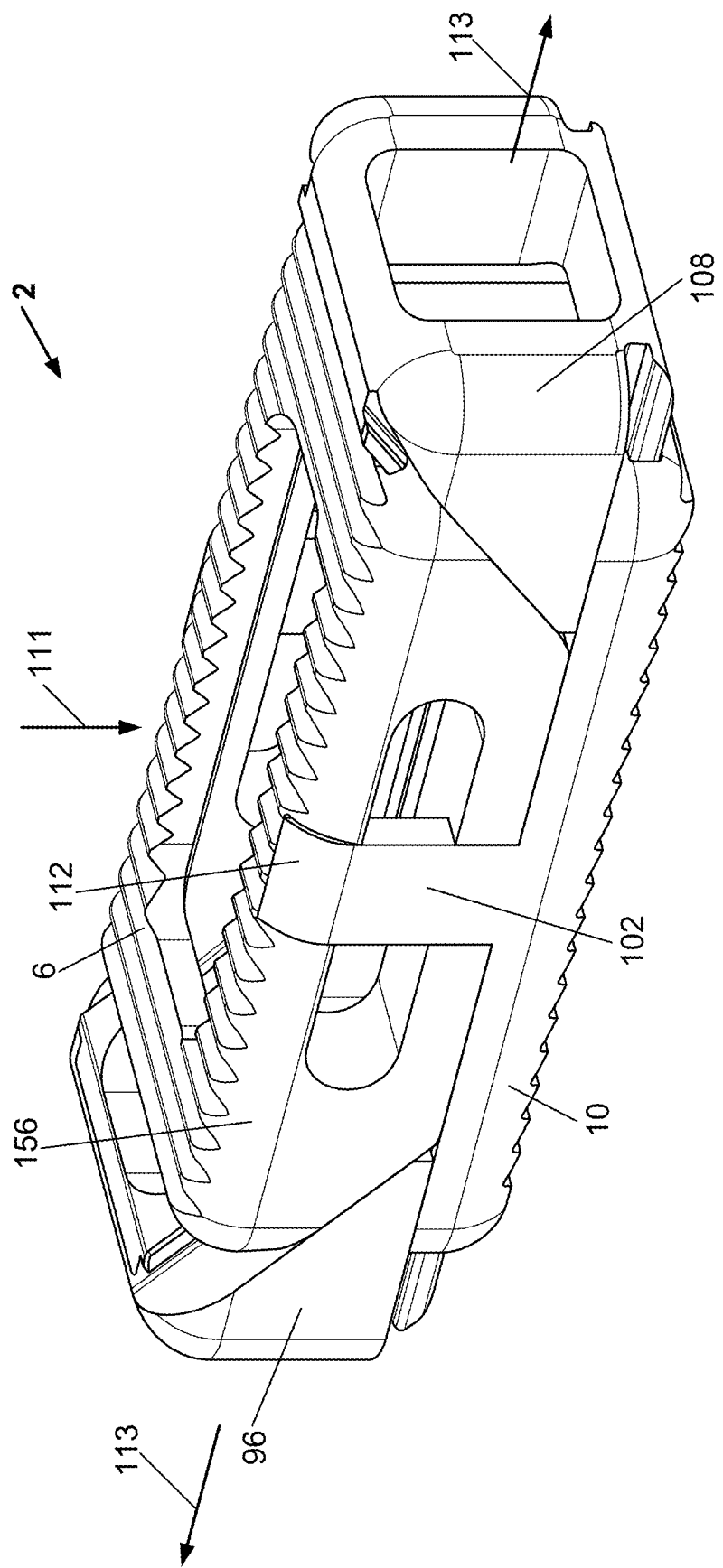

FIGS. 36, 37, and 39 illustrate that the ramps 96, 108 can be pushed outward, as shown by arrows 113, toward each ramp's respective longitudinal side of the base plate 10. The ramps 96, 108 can be pushed outward, for example, by a deployment or other tool. When the ramps 96, 108 are slid outward, as shown, the top plate 6 and base plate 10 can translate toward each other, as shown by arrow 111. The top plate 6 and base plate 10 can then have a radially compressed (e.g., only in the "y"-axis or from the top of the page to the bottom of the page of FIGS. 36, 37, and 39) configuration. The top plate 6 can interference fit against the bottom plate 10 when the expandable support device 2 is fully radially compressed, as shown. The interference fit of the top 6 against the bottom plate 10, and the slidable attachment of the ramps 96, 108 to the top 6 and the bottom plate 10 can lock the top plate 6, base plate 10 and ramps 96, 108 together (e.g., not allowing any to separate). The device 2 can be attached to a deployment tool (e.g., by removably attaching to one or more ramp ports) and/or delivered to a target site in the radially compressed configuration.

FIGS. 38 and 41 illustrate that one or more locking pin channels 164 can be defined transversely through the device 2. A locking pin 162 can be inserted through each locking pin channel 164. The locking pin 162 can be inserted through the locking pin channel 164 after the device 2 has been inserted at the target site and expanded. The locking pin channel 164 can be defined by locking pin ports 166 on the stability bars 102 and the side port. The locking pin ports 166 can be circular, as shown, oval, or combinations thereof.

The locking pin 162 can be configured to limit the vertical expansion of the device 2. For example, the locking pin 162 can be configured to substantially prevent the device 2 from disassembling.

Figure 42:
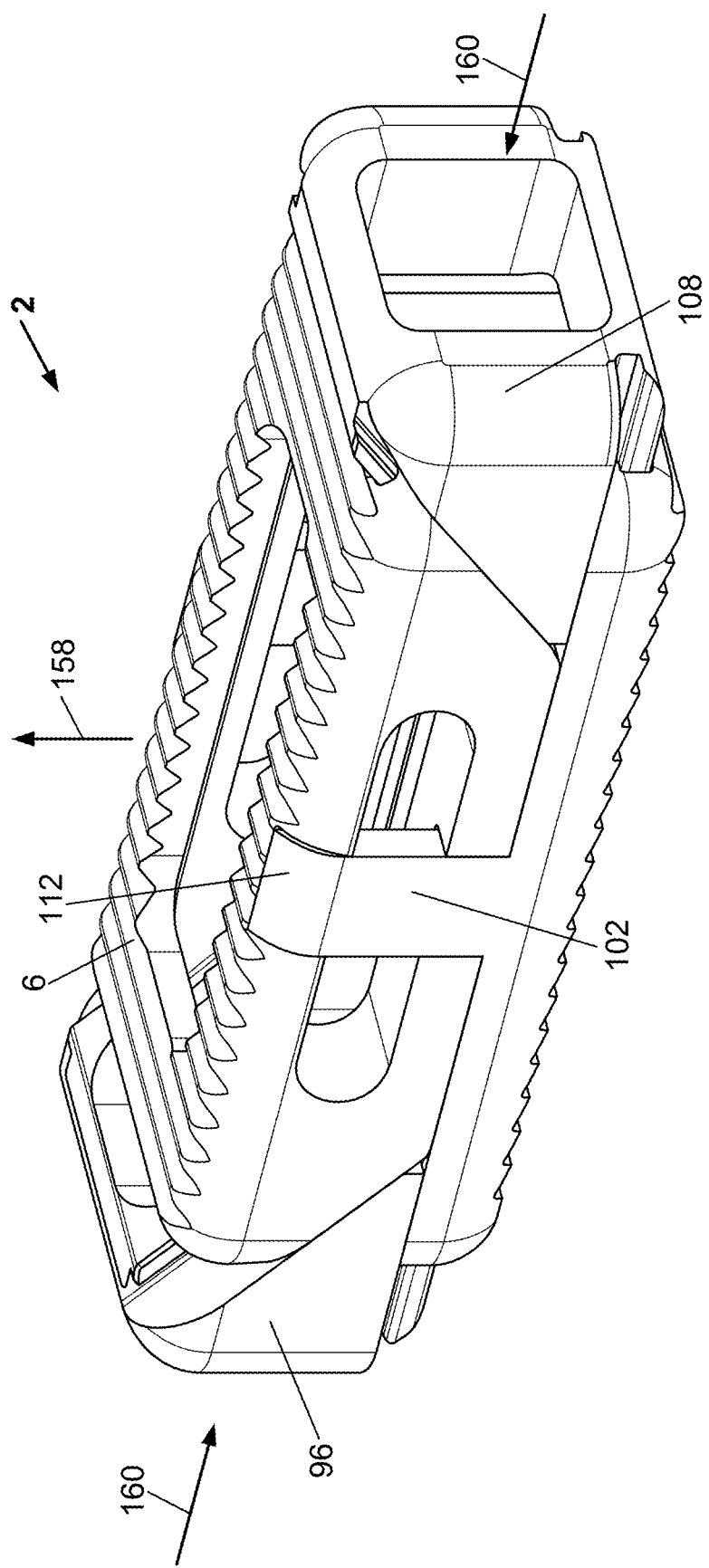
FIG. 42 illustrates a method of longitudinally compression and radially expanding the variation of the device of FIG. 36, for example after deployment at a target site.

FIG. 42 illustrates that the device 2 can be longitudinally compressed 160, as shown by arrows, resulting in radial and/or vertical expansion 158, as shown by arrow, for example performed after the device 2 is positioned within a vertebra or between vertebrae. The ramps 96, 108 can be slidably translated along the longitudinal axis 4 and inward and/or toward the center of the device 2. The expansion of the device 2 can increase the height and provide structure support for a compressed or otherwise damaged vertebra (e.g., when the device 2 is deployed within a vertebra) and/or return adjacent vertebrae to a more natural/physiological configuration (e.g., when the device 2 is deployed between adjacent vertebrae).

Figure 43:
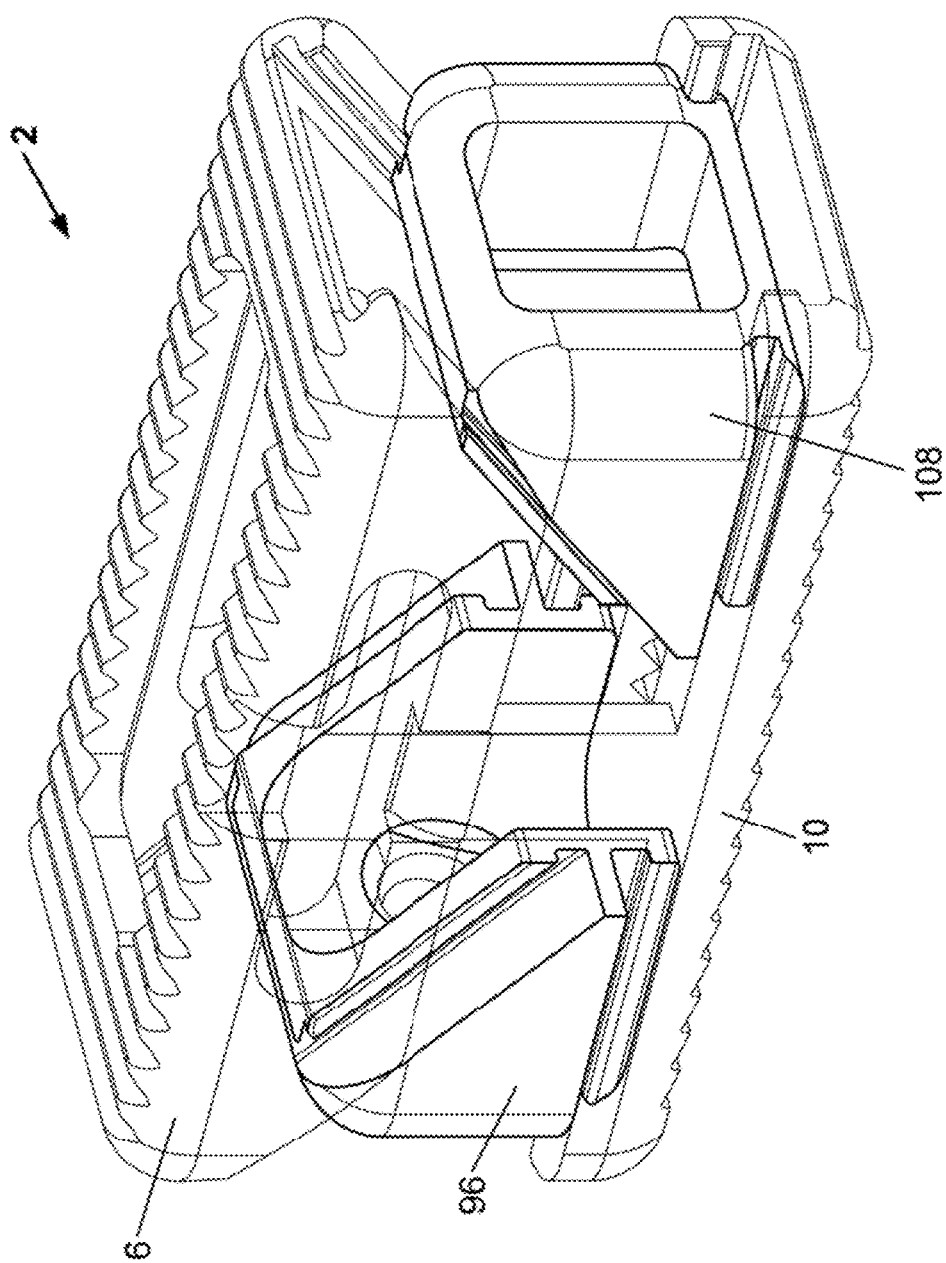
FIGS. 43 and 44 are perspective and top views, respectively, of the variation of the device of FIG. 20 in a deployed configuration.
Figure 44:
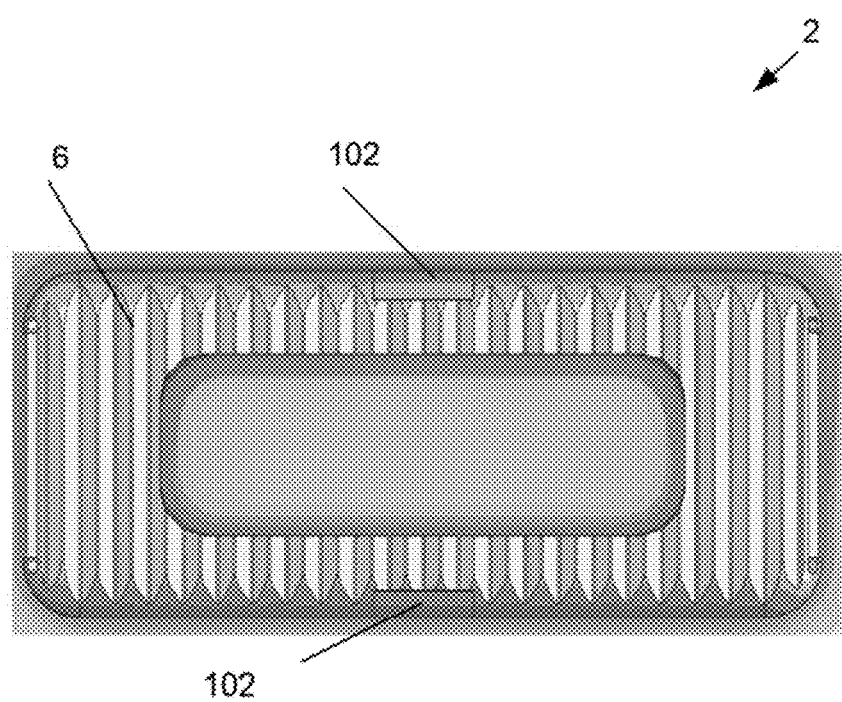

FIGS. 43 and 44 illustrate the device 2 in a deployed configuration, for example after completion of the longitudinal compression 160 and radial and/or vertical expansion 158 as shown in FIG. 42.

Figure 45:
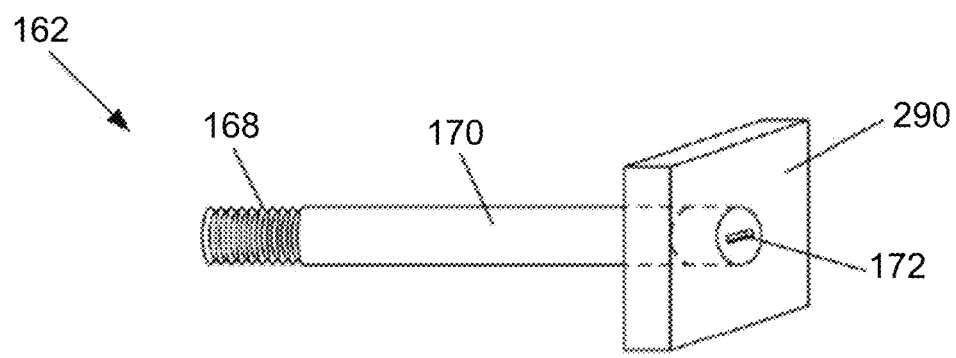
FIGS. 45 and 46 illustrate variations of the locking pin.

FIG. 45 illustrates a variation of the locking pin 162 that can have a pin shaft 170 with a driver slot 172, for example, configured to receive a screw driver or drill bit. The pin shaft 170 can have pin thread 168 configured to releasably or fixedly attach to one or both of the ramp ports. The pin thread 168 can extend along all or part of the length of the pin shaft 170. The pin shaft 170 can be rotatably or fixedly attached to or integral with a locking plate 290. The locking plate 290 can be at the end of the pin shaft 170 with the driver slot 172. The locking plate 290 can be at the same or opposite end of the pin shaft 170 from the thread 168.

Figure 46:
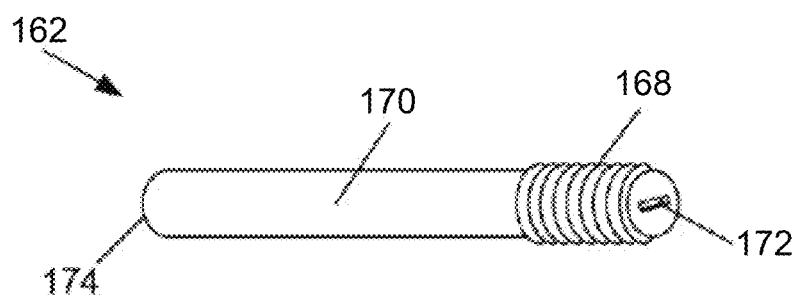

FIG. 46 illustrates that the pin shaft 170 can have no locking plate 290. The pin thread 168 can be at the end of the pin shaft 170 with the driver slot 172. One end of the pin shaft 170, for example opposite the driver slot 172, can be an abutment end 174.

Figure 47:
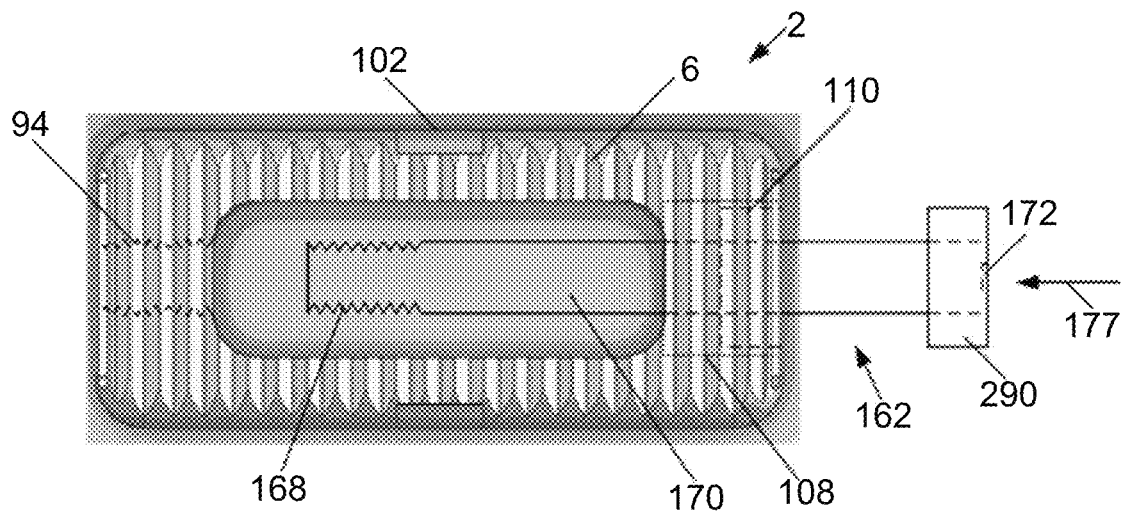
FIGS. 47 and 48 illustrate a variation of a method for using the variation of the locking pin of FIG. 45.
Figure 48:
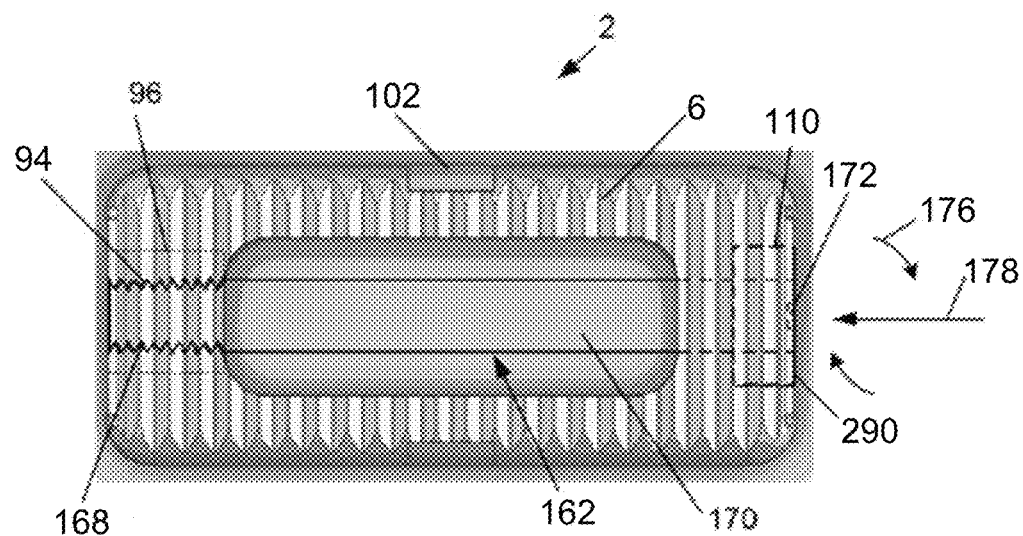

FIG. 47 illustrates that the locking pin 162 can be inserted, as shown by arrow 177, through the second side ramp 108. FIG. 48 illustrates that the pin shaft 170 can be translated and rotated, as shown by arrows, to screw the pin thread 168 into the threaded ramp port 94 in the first side ramp 96. The ramp locking plate 290 can fit into the ramp locking plate port 110. The locking pin 162 can be screwed tightly enough to substantially fix the locking pin 162.

Figure 49:
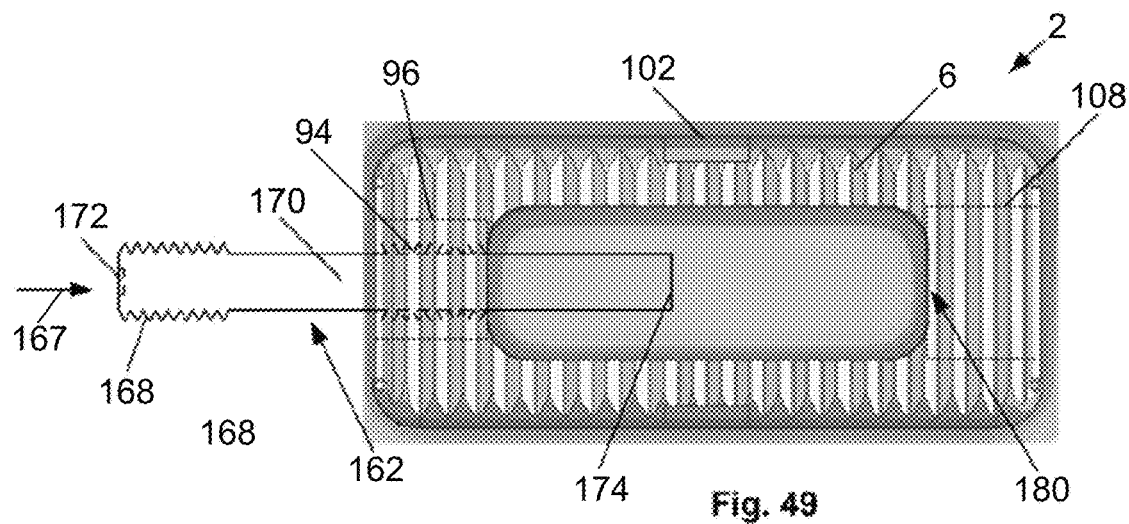
FIGS. 49 and 50 illustrate a variation of a method for using the variation of the locking pin of FIG. 46.

FIG. 49 illustrates that the locking pin 162 can be inserted, as shown by arrow 167, through the threaded ramp port 94. The second side ramp 108 and/or the top 6 and/or the bottom plates 10 can have a ramp abutment section 180. The ramp abutment section 180 can be configured to interference fit with and/or fixedly attach to the abutment end 174.

Figure 50:
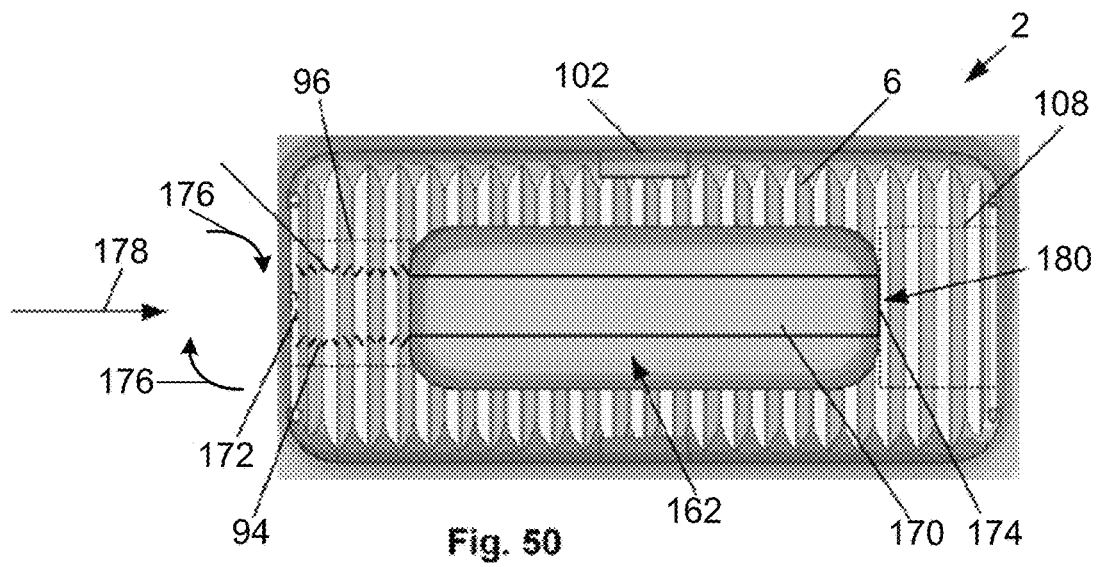

FIG. 50 illustrates that the pin shaft 170 can be translated and rotated 178, as shown by arrows. The abutment end 174 can interference fit and/or fixedly attach to the ramp abutment section 180.

A biocompatible adhesive or epoxy can be applied to the pin thread 168, threaded ramp port 94, abutment end 174, ramp abutment section 180, or combinations thereof.

FIGS. 51, 52 and 53 illustrate that one, two or more locking pin channels 164 can be defined longitudinally through the device 2. One, two or more locking pins 162 can be inserted in each locking pin channel 164, for example during or after deployment of the remainder of the device 2. The locking pins 162 can prevent overexpansion and/or overcompression and/or disassembly of the device 2.

The locking pin channel 164 can have locking pin ports 166 through the top 6, and/or bottom plates 10, and/or either or both side ramps 96, 108.

Two locking pin channel 164 can be located on opposite sides of the threaded ramp port. The locking pin channels 164 and ports 166 can have a circular cross-section (i.e., be cylindrical), as shown in FIG. 53.

Figure 54:
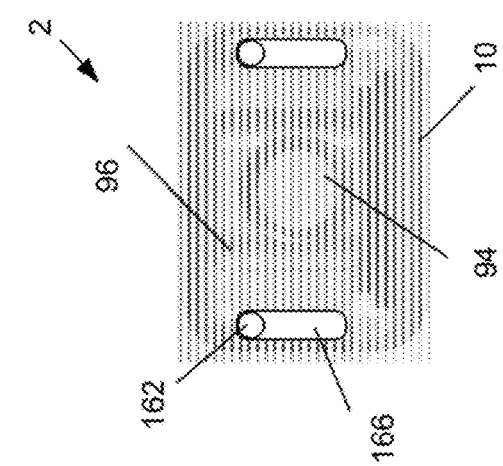
FIGS. 54 and 55 are side and end views, respectively, of a variation of the device with the locking pin.
Figure 55:
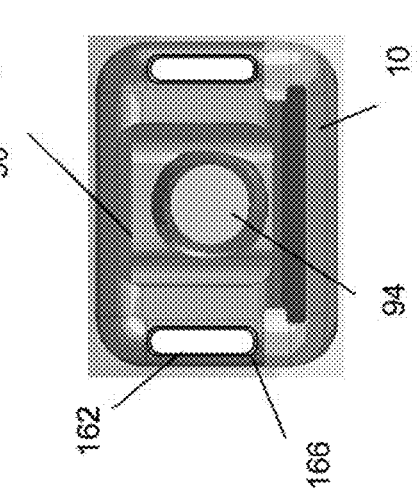

FIGS. 54 and 55 illustrates that the locking pin 162 can be cylindrical. The locking pin channel 164 and locking pin port 166 can have elongated cross-sections, such as an oval or rectangular or oblong cross-sections. The locking pin 162 can be free to move vertically within a range of motion within the locking pin port 166.

Figure 56:
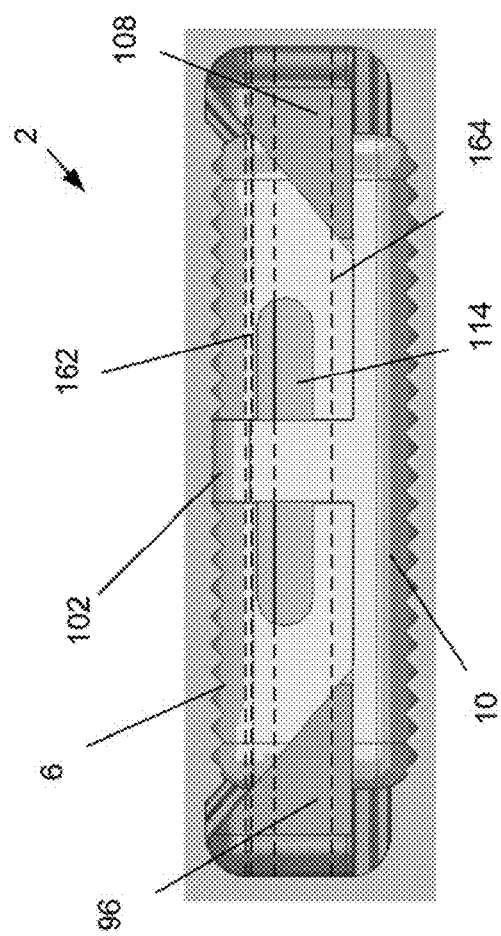
FIGS. 56 and 57 are side and end views, respectively, of a variation of the device with the locking pin.
Figure 57:
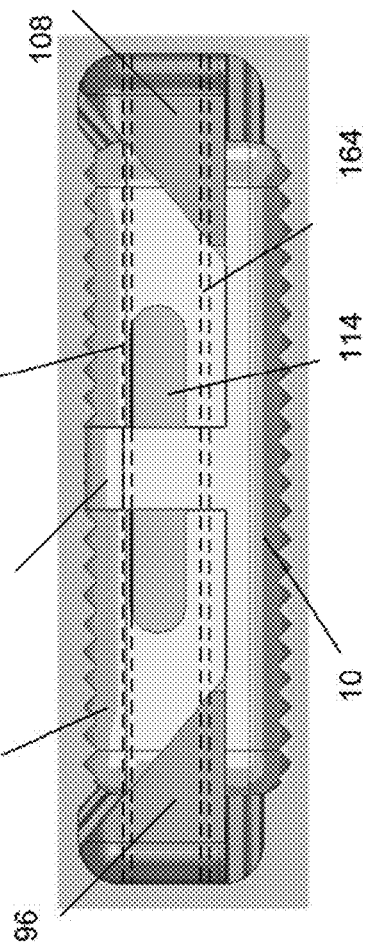

FIGS. 56 and 57 illustrate that the locking pin 162 can be a substantially similar shape and size as the locking pin channel 164. The locking pin 162 can be substantially unmovable within the locking pin port 166. The locking pin 162, locking pin channel 164 and locking pin port 166 can all have elongated cross-sections, such as an oval or rectangular or oblong cross-sections.

Figure 58:
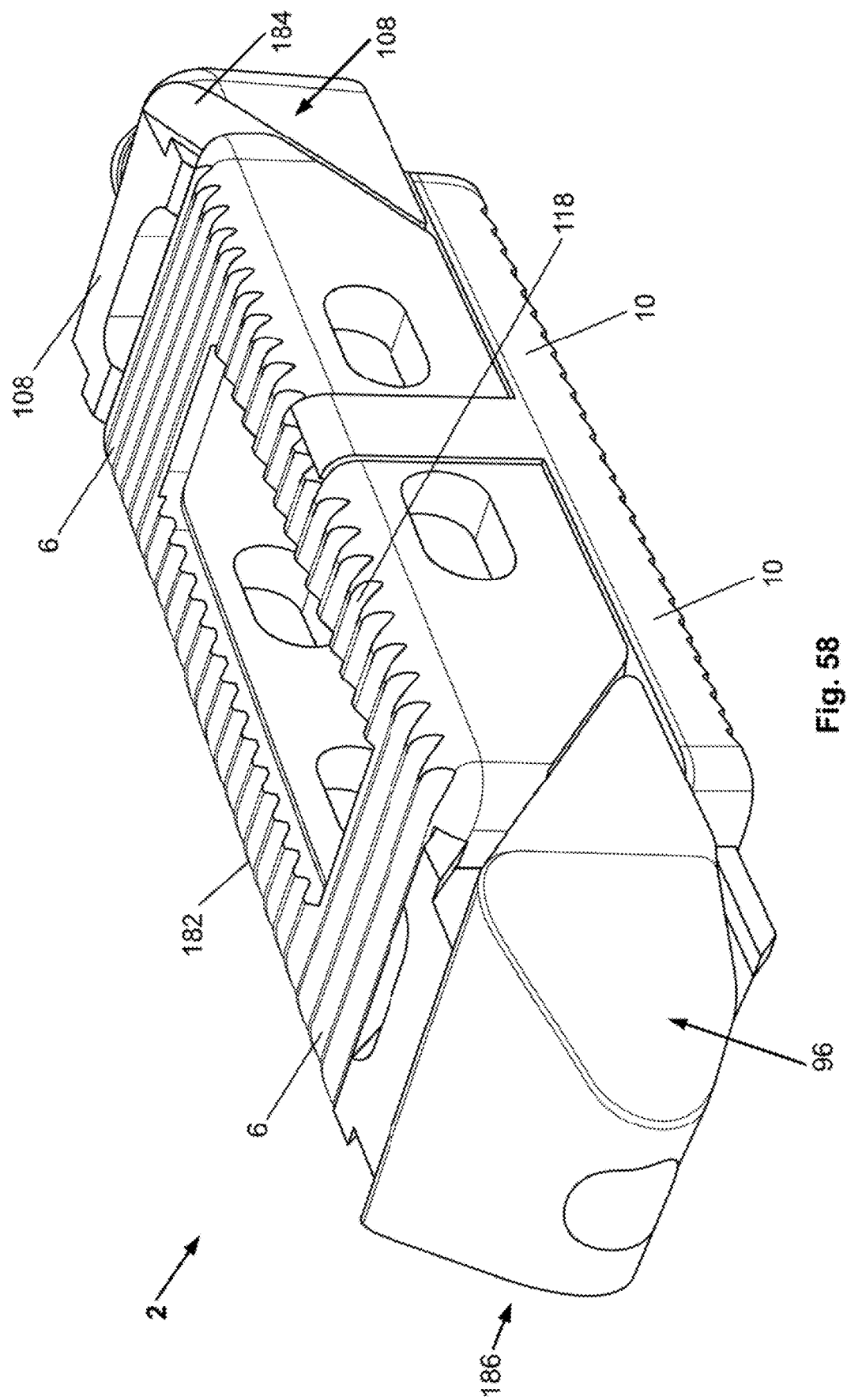
FIGS. 58 and 59 are perspective and side views, respectively, or a variation of the device in a radially unexpanded configuration.
Figure 59:
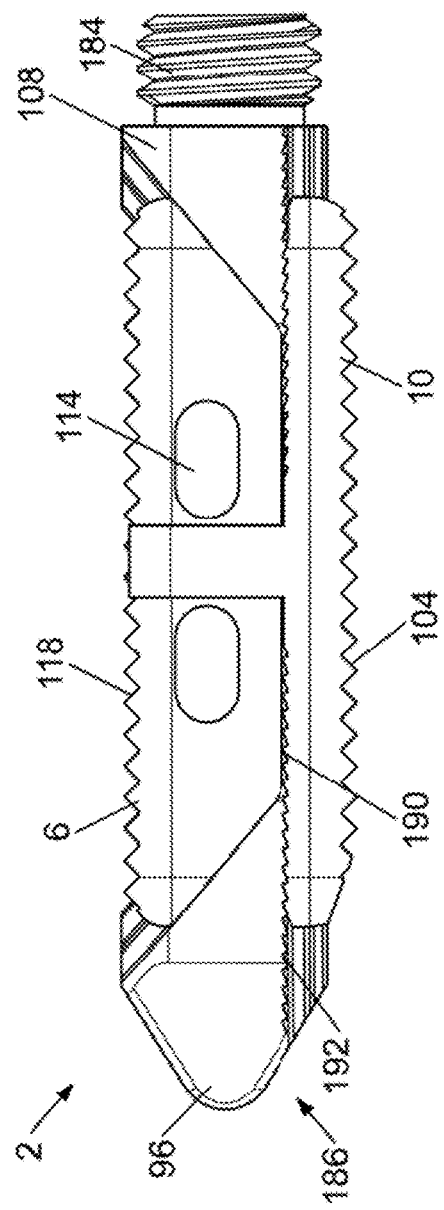

FIGS. 58 and 59 illustrate that one or both of the ramps 96, 108 can have first fixing teeth 192. The first fixing teeth 192 can be in contact with the top 6 and/or the bottom 10. The top 6 and/or the bottom (shown as bottom only) plates 10 can have second fixing teeth 190.

The first fixing teeth 192 can mechanically interact with the second fixing teeth 190 to allow relative translation in a first direction. The first fixing teeth 192 and the second fixing teeth 190 can interact to obstruct (e.g., by interference fitting the first fixing teeth against 192 the second fixing teeth 190) relative translation in a second direction. For example, the fixing teeth 192 can obstruct the side ramps 96 from moving longitudinally away from each other (i.e., and obstruct the top from moving closer to the bottom). Also for example, the fixing teeth 192 can allow relative translation of the side ramps 96, 108 toward each other (i.e., and allow the top to move away from the bottom).

The second side ramp 108 can have a first end 186. The first end 186 can be configured to dissect tissue. The first end 186 can have a blunt or sharp point.

The second side ramp 108 can have a tool connector 184, such as an externally and/or internally threaded cylinder extending longitudinally from the second side ramp 108 away from the first side ramp 96. The tool connector 184 can be configured to removably attach to a deployment tool.

Figure 60:
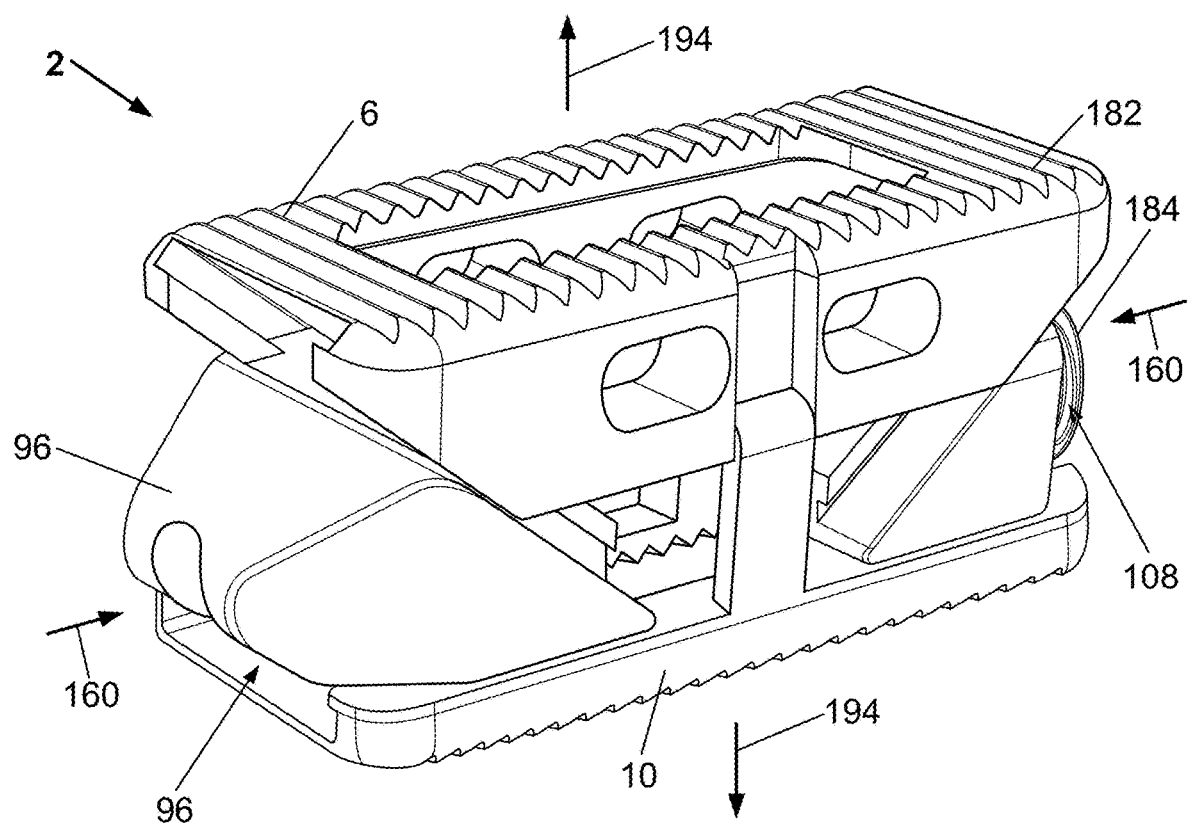
FIGS. 60 and 61 are perspective and side views, respectively, or the variation of the device of FIGS. 58 and 59 in a radially expanded configuration.
Figure 61:
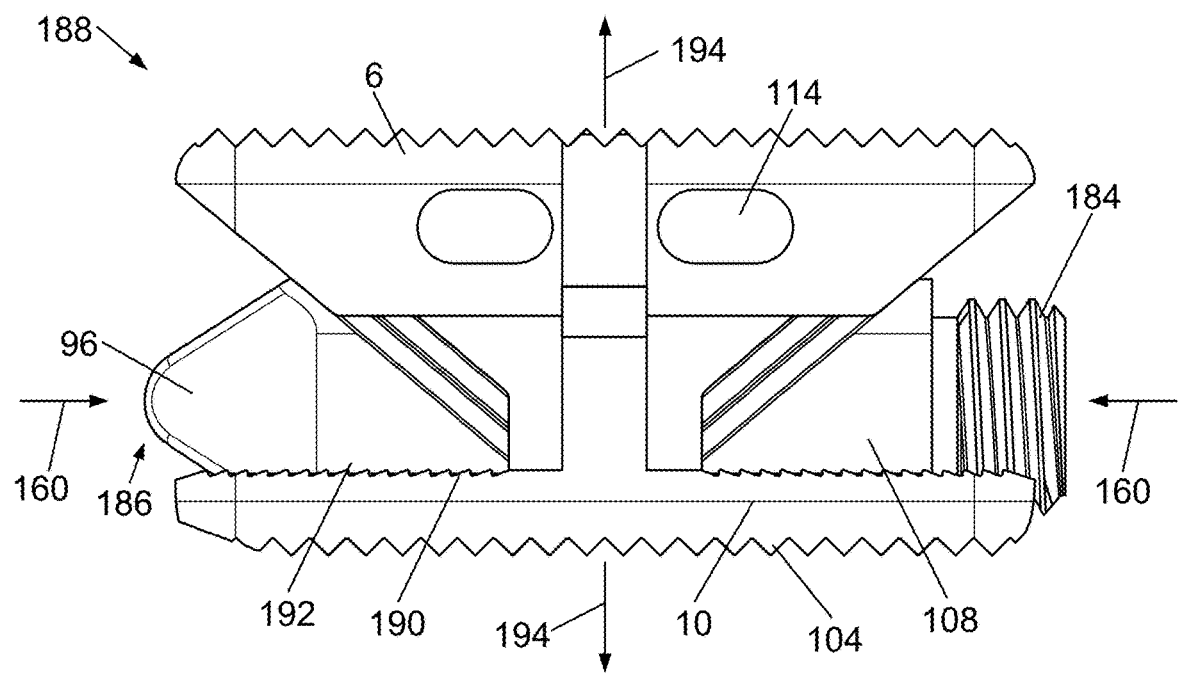

FIGS. 60 and 61 illustrate that the first side ramp 96 and second side ramp 108 can be longitudinally compressed 160, as shown by arrows, toward each other. For example, an external deployment tool can be attached to the first side ramp 96 and second side ramp 108 and apply a compressive force. The base 10 and top plates 6 can expand away from each other 194, as shown by arrows.

The first fixing teeth 192 can unidirectionally interference fit the second fixing teeth 190. The unidirectional interference fit of the first fixing teeth 192 and the second fixing teeth 190 can substantially impede or prevent the opposite ramps from moving longitudinally away from each other, for example, therefore impede or preventing compression of the top toward the bottom and vice versa.

The unidirectional interference fit of the first fixing teeth 192 and the second fixing teeth 190 can allow the opposite ramps to move longitudinally toward each other, for example, therefore allowing the top to expand away from the bottom and vice versa.

The expandable support devices 2 can have textured and/or porous surfaces for example, to increase friction against bone surfaces, and/or promote tissue ingrowth. The expandable support devices 2 can be coated with a bone growth factor, such as a calcium base.

Figure 62A:
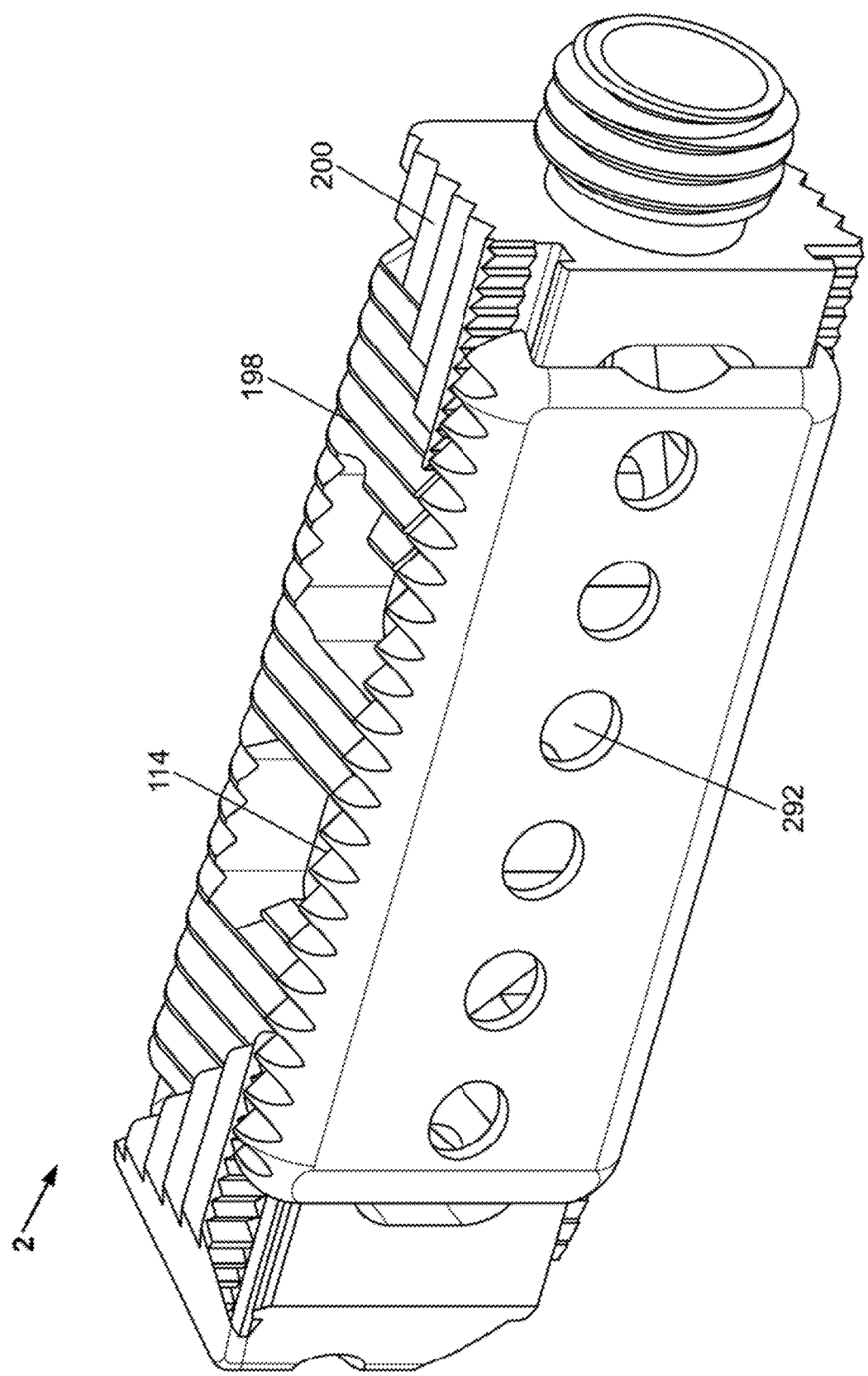
FIGS. 62a, 62b and 62c are bottom perspective, end and side views, respectively, of a variation of the device in a longitudinally expanded configuration.
Figure 62B:
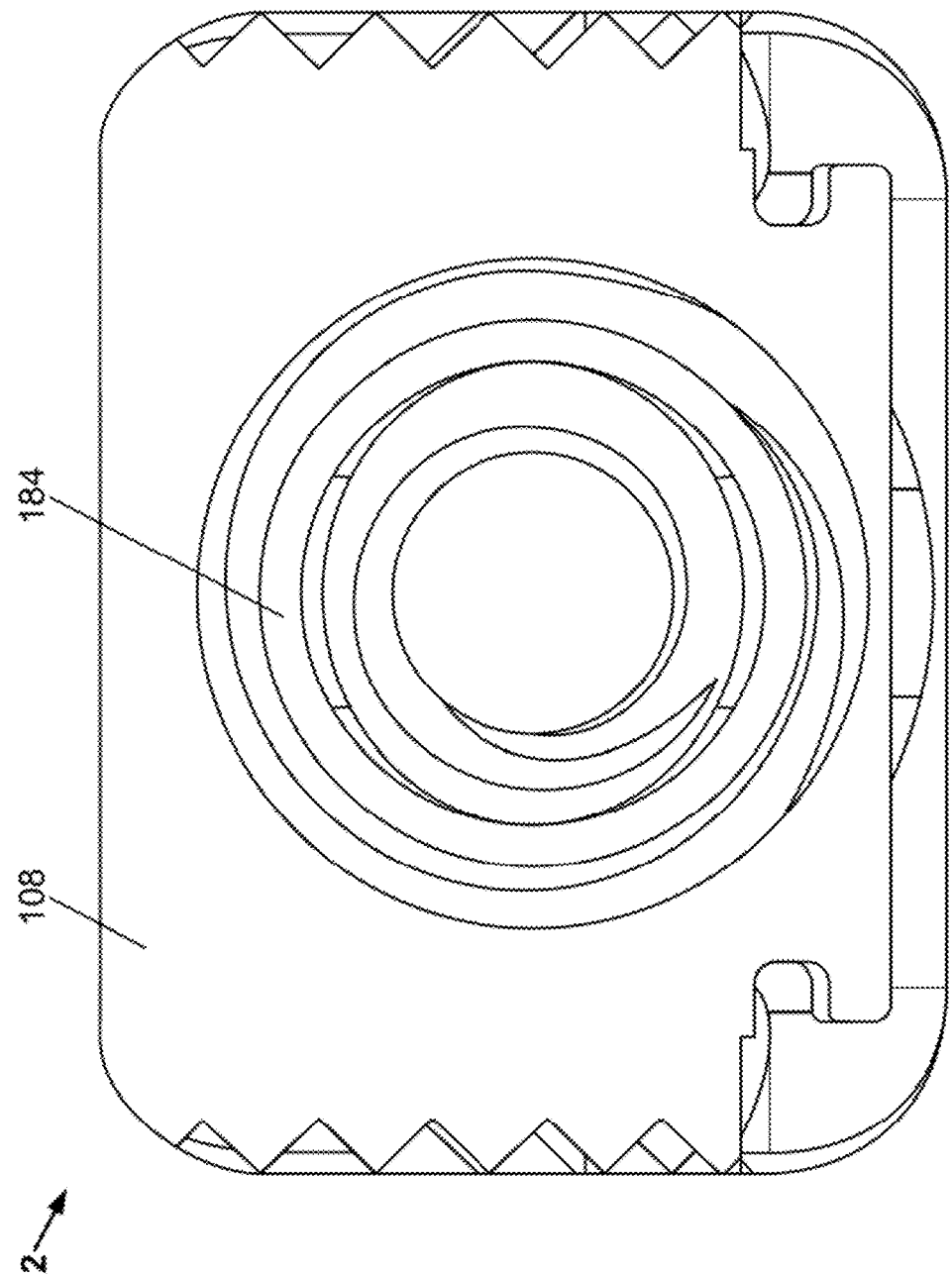
Figure 62C:
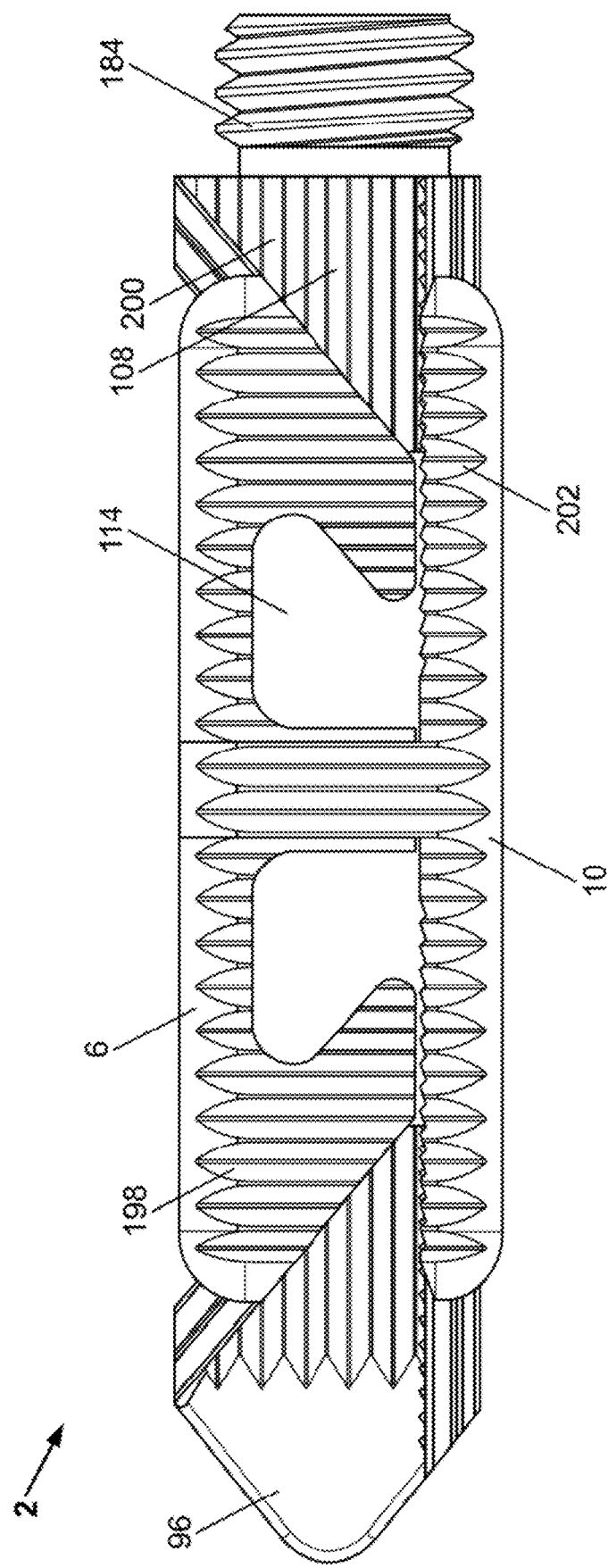

FIGS. 62a through 62c illustrate that the bottom ports 292 can be one or more circular ports, for example six ports. The bottom ports 292 can be aligned in a single row parallel with the longitudinal axis of the device 2.

The side ports 114 can open against the edge of the top plate 6 on one or more sides (e.g., the bottom sides, as shown) of the side ports 114.

The top plate 6 can have top plate side teeth 198 on the external lateral sides of the top plate 6. The bottom plate 10 can have bottom plate side teeth 202 on the external lateral sides of the bottom plate 10. The top plate side teeth 198 and/or the bottom plate side teeth 202 can be oriented from the top to the bottom of the device 2 (i.e., perpendicular to the longitudinal axis of the device 2). The top plate side teeth 198 can be aligned with the bottom plate side teeth 202.

The external lateral sides of the first side ramp 96 and/or second side ramp 108 can have ramp side teeth 200. The ramp side teeth 200 can be oriented parallel with the longitudinal axis of the device 2. The top plate side teeth 198 and/or the bottom plate side teeth 202 can be oriented perpendicular to the orientation of the ramp side teeth 200.

Figure 63A:
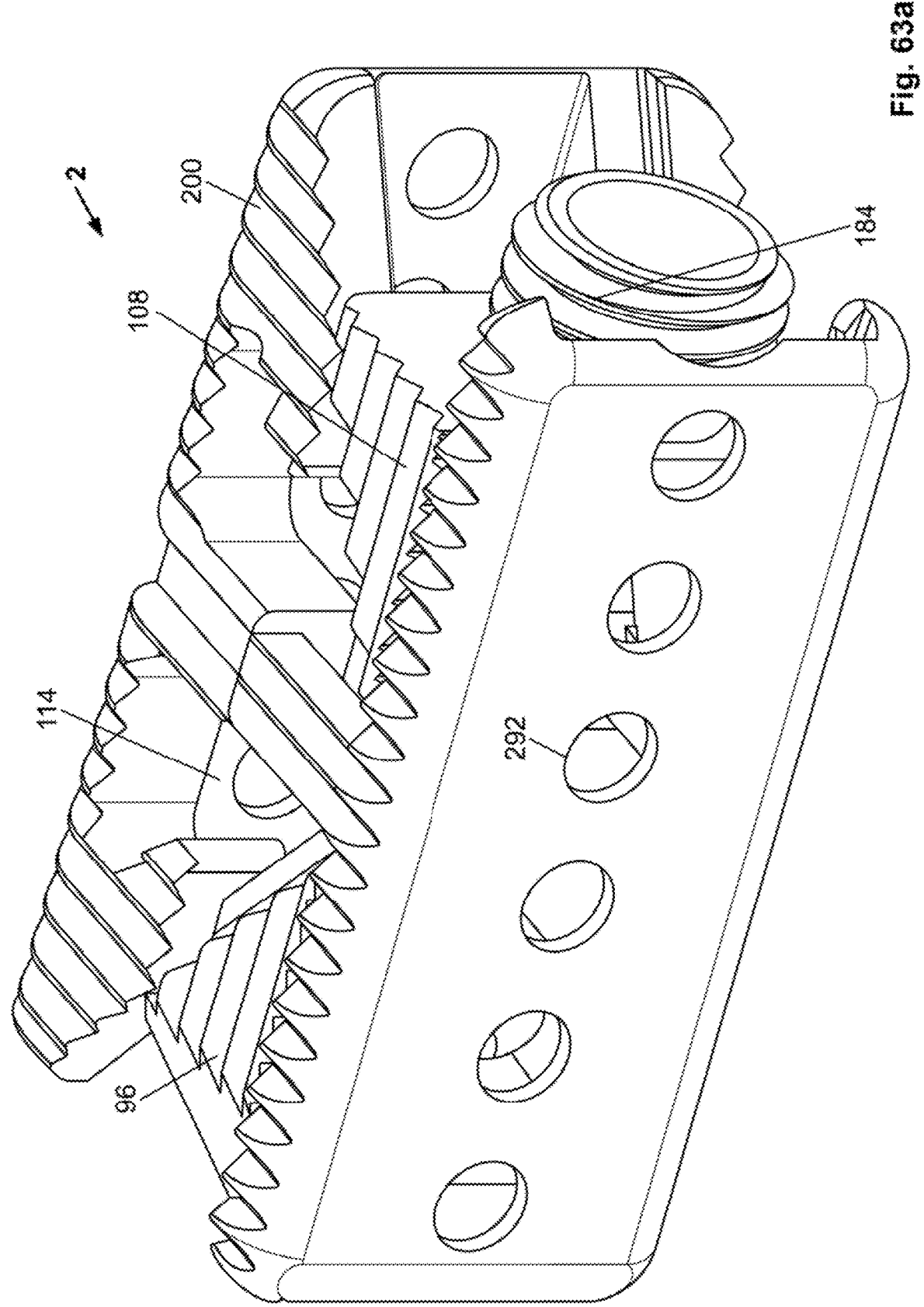
FIGS. 63a, 63b, and 63c are bottom perspective, end and side views, respectively, of the device of FIGS. 62a through 62c in a longitudinally compressed and radially expanded configuration.
Figure 63B:
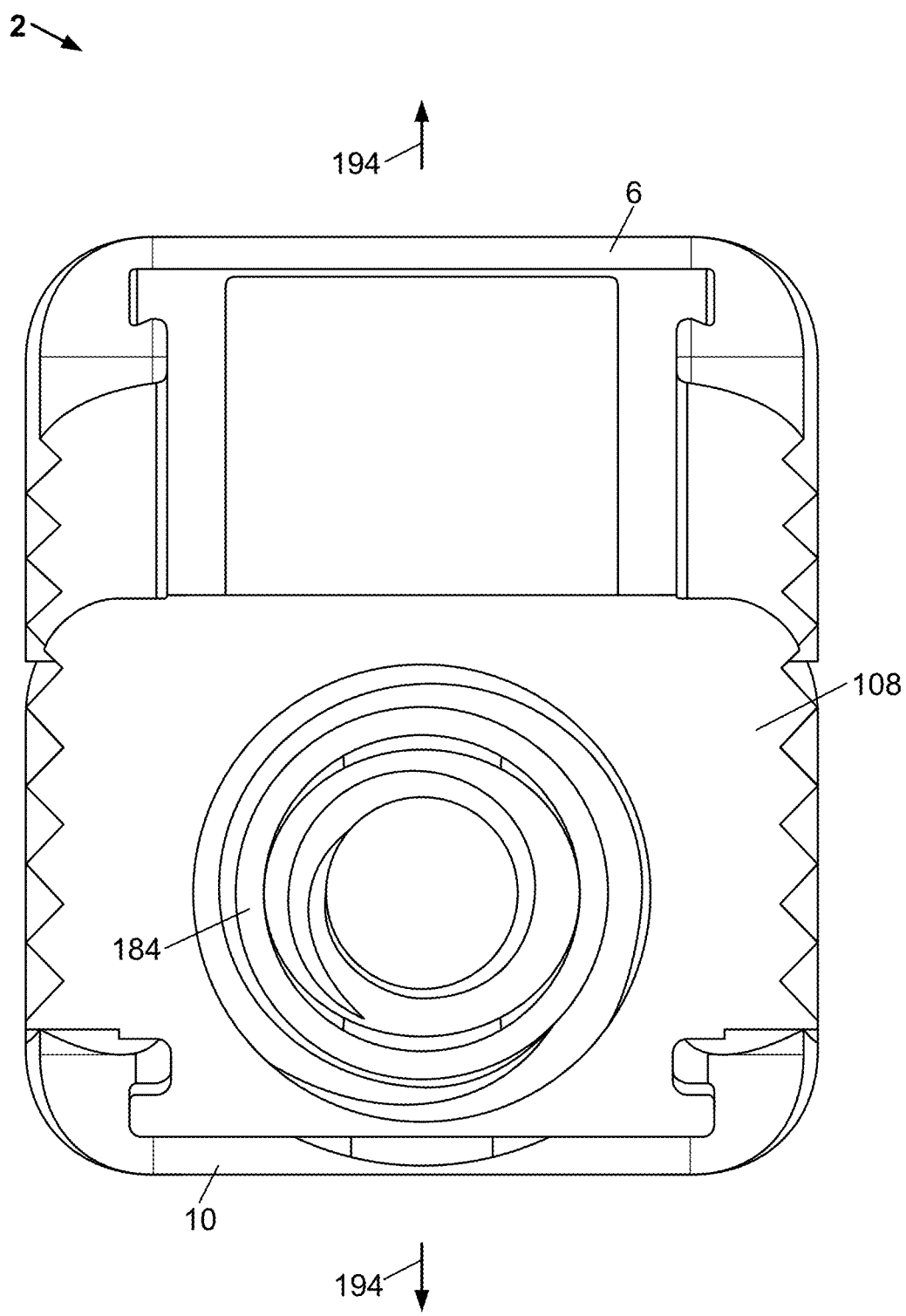
Figure 63C:
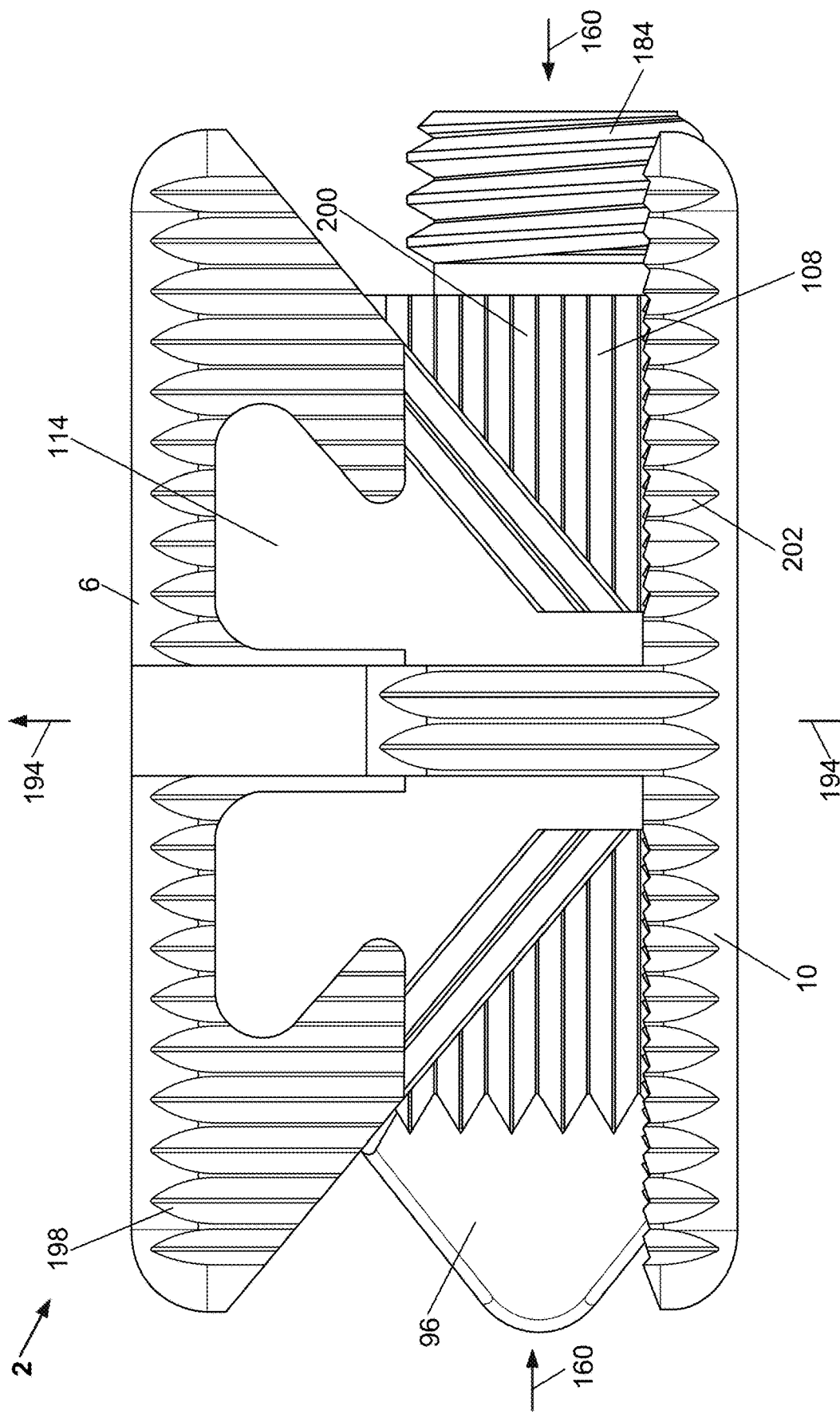

FIGS. 63a through 63c illustrate that the top plate 6 and/or bottom plate 10 can be expanded away from each other in the directions of the orientation of the longitudinal axes of the top plate side teeth 198 and the bottom plate side teeth 202. The first 96 and/or second side ramps 108 can be contracted toward one another in the direction of the orientation of the longitudinal axis of the ramp side teeth 200 of the first 96 and second side ramps 108. The top plate side teeth 198, bottom plate side teeth 202, and ramp side teeth 200 can act as low-friction rails against surrounding tissue when the device 2 is radially expanded 194 at the target site.

The side ports 114 that open to the bottom edge of the top plate 6 can create a single side port 114 that can extend to the bottom plate 10.

Figure 64:
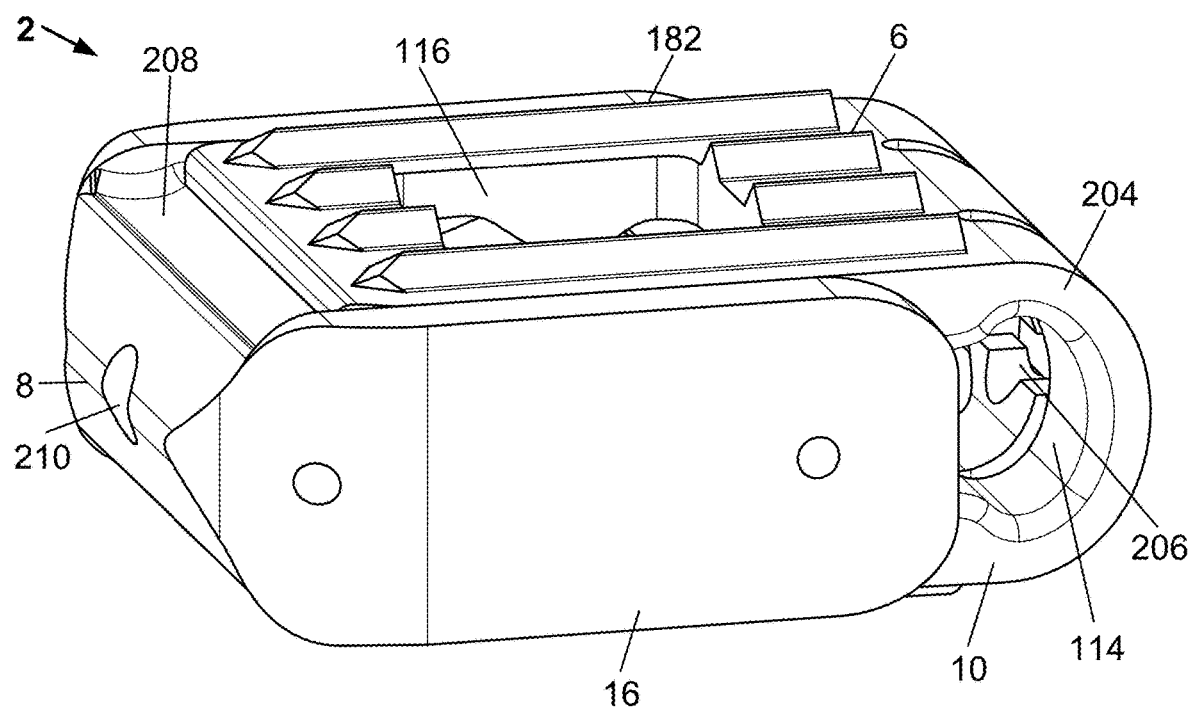
FIG. 64 illustrates a variation of the device in a longitudinally expanded configuration.

FIG. 64 illustrates that the top plate 6 can be rotatably attached to the bottom plate 10. The top plate 6 and the bottom plate 10 can be integral with or attached to a plate hinge 204. The top plate 6 and bottom plate 10 can be attached at a first end at the plate hinge 204. The top plate 6 and bottom plate 10 can be unattached at a second end away from the plate hinge 204.

The top plate 6 and bottom plate 10 can form a side port 114. The middle plate 8 can be slidably received by the side port 114. The middle plate 8 can have a side wall 16. The side wall 16 can obstruct, cover, and/or seal the external side of the side port 114.

The middle plate 8 can have a middle plate port 210. The plate hinge 204 can have a plate hinge port 206. The middle plate port 210 and the plate hinge port 206 can be aligned along the longitudinal axis of the device 2. A deployment tool can be releasably attached to the middle plate port and/or the plate hinge port. The deployment tool can compress the middle plate port 210 toward the plate hinge port 206.

The middle plate 8 can have one or more middle plate ramps 208, for example positioned adjacent to the inner surfaces of the top plate 6 and the bottom plate 10. When the middle plate 8 is longitudinally extended away from the top 6 and bottom plates 10, as shown in FIG. 64, the plane of the top plate 6 can be can be substantially parallel to the plane of the bottom plate 10.

Figure 65:
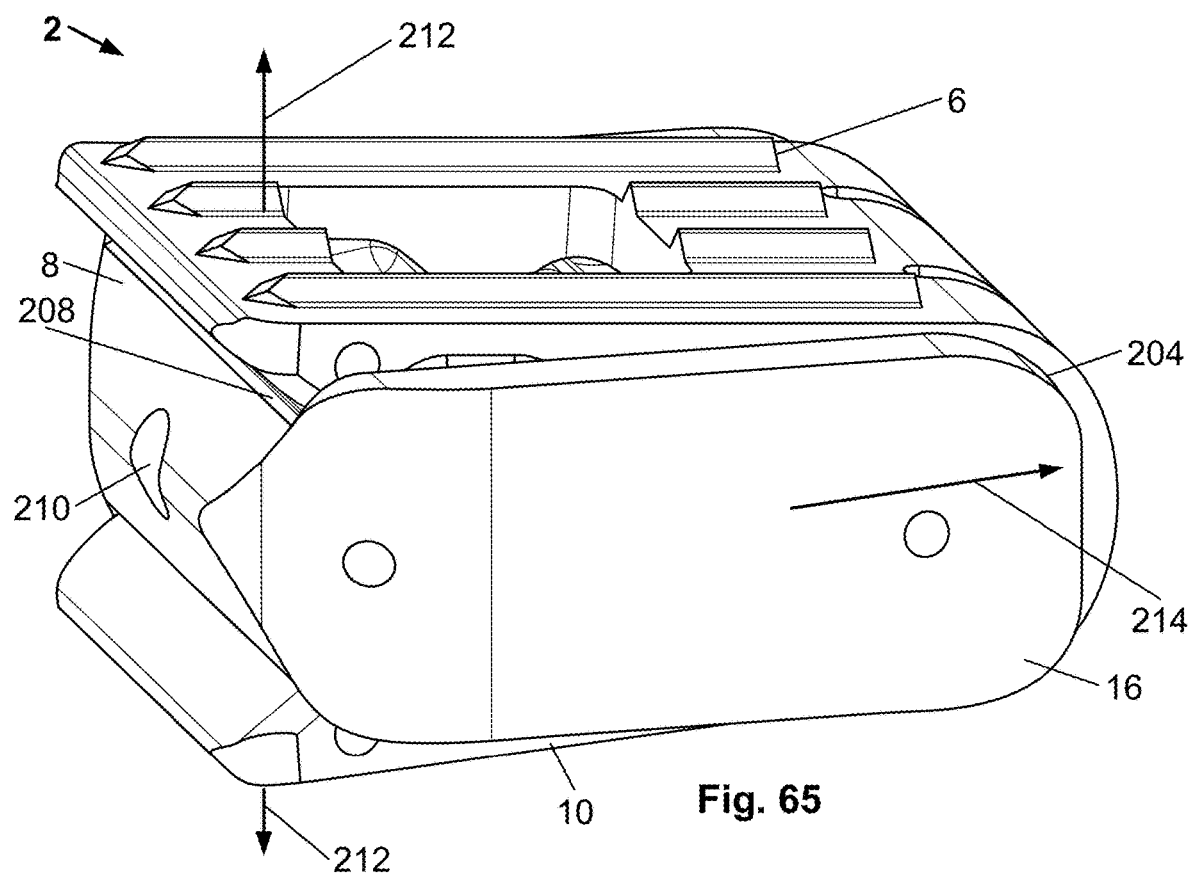
FIG. 65 illustrates the device of FIG. 64 is a longitudinally contracted and radially expanded configuration.

FIG. 65 illustrates that the middle plate 8 can be translated toward the plate hinge 204. For example, a deployment tool can exert a compression force on the plate hinge 204 and the middle plate 8, translating the middle plate 8 toward the middle plate ramp 208, as shown by arrow 212. The top plate ramps can rotate 212, the top plate 6 away from the bottom plate 10.

Figure 66C:
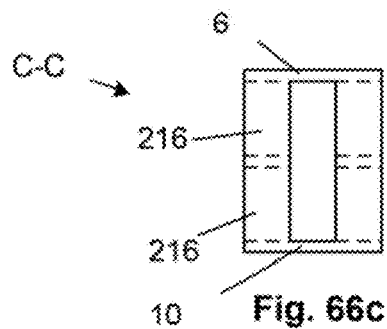
FIGS. 66c and 66d are variations of cross-section C-C of FIG. 66b.

FIGS. 66a and 66b illustrates that the device 2 can exhibit ductile or deformable expansion during deployment. For example, the device 2 can have struts 216 forming an internal strut system. The struts 216 can convert a longitudinally compressive force 160 into a radial expansion 194. The struts 216 can act as an internal support for the device 2. As the device radially expands 194, the cells 88 of the device 2 can expand. The device 2 can therefore become more porous. The device 2 can have a square or rectangular cross-section as shown in FIGS. 66a, 66b and 66c. The transverse cross section of the device 2 can be non-round.

Figure 66D:
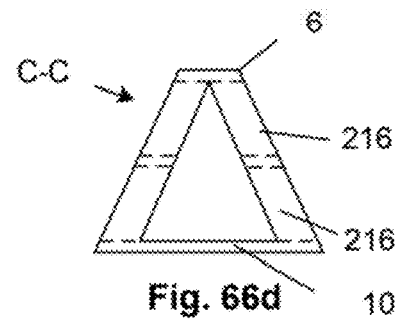

FIG. 66d illustrates that the device 2 can have a substantially triangular or quadrilateral (e.g., trapezoidal) cross-section. The device 2 can have a round, hexagonal, octagonal, or other cross-sectional configuration.

The device 2 can have one or more radiopaque and/or echogenic markers. For example, the device 2 can have aligned markers on the top plate 6, middle plate 8 and bottom plate 10. When the device 2 is in a contracted pre-deployment configuration, the markers can be located immediately adjacent to one another, for example appearing as a single marker. When the device 2 is in an expanded configuration, the markers can move apart from each other, indicating to a doctor performing the implantation and deployment procedure using visualization (e.g., x-ray or ultrasound-based) that the device 2 has expanded. Under visualization the markers can also indicate the location and orientation of the device 2.

Method of Using

The cartilage can be partially, substantially or completely removed from the inter facet joint. A three-dimensional cavity shape can be formed into the facet surfaces, for example to improve stability and fusion of the device when the device is implanted. A bone removal tool can be used on the facet surfaces prior to the insertion of the implant to remove and shape bone and/or other tissue. The bone removal tool can be cannulated and have guides to assure proper depth and orientation within the facet joint space. The bone removal tool (which can also remove cartilage and other tissue) can be round or non-round. The bone removal tool can be shaped to match the shape profile of the unexpanded implant.

Figure 67:
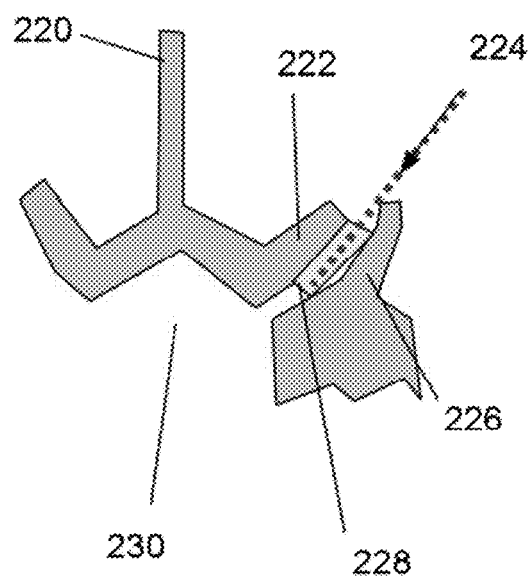
FIGS. 67 and 68 are transverse sectional views of a variation of a method for using the device.

FIG. 67 illustrates that the device 2 can be inserted along the implant pathway 224 into the target site, such as between the superior articular process 222 and inferior articular process 226 of a facet joint. The device 2 can be inserted into the facet joint without protruding into the vertebral foramen 230. (The spinous process 220 is shown as a landmark for illustrative purposes.) The device 2 can be partially or completely radially expanded before or after inserting the device 2 into the target site. An expanded bone cavity can optionally be drilled into the facet joint before insertion of the device 2 in which the device 2 can be inserted.

Figure 68:
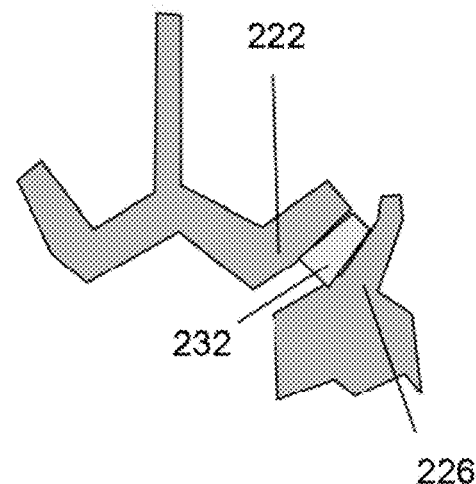

FIG. 68 illustrates that the device 2 can then be expanded and held in place by an interference or friction fit within the bone cavity in the facet joint. Regular spinal loads, such as compression of the facet joint, can provide additional anchoring and settling (i.e., stop migration) of the device 2. The device can expand into a reverse taper 232, as shown in FIG. 67. For example, the end of the device 2 closer to the vertebral foramen 230 can expand to a larger radius than the end of the device 2 further from the vertebral foramen 230.

The devices can be made from PEEK, any medical grade polymer or metal, or any other material disclosed herein. The device can be coated, for example with bone morphogenic protein (BMP), ceramic, and/or any other material disclosed herein.

FIGS. 69 through 75 illustrate a variation of the location of the device and the fusion location when this device is deployed in use. The device can be deployed less (e.g., minimally) invasively, over the wire, percutaneously, used with a vertebral body replacement or fusion cage, or combinations thereof. The device can be expandable and un-expandable for removal or repositioning.

Figure 69:
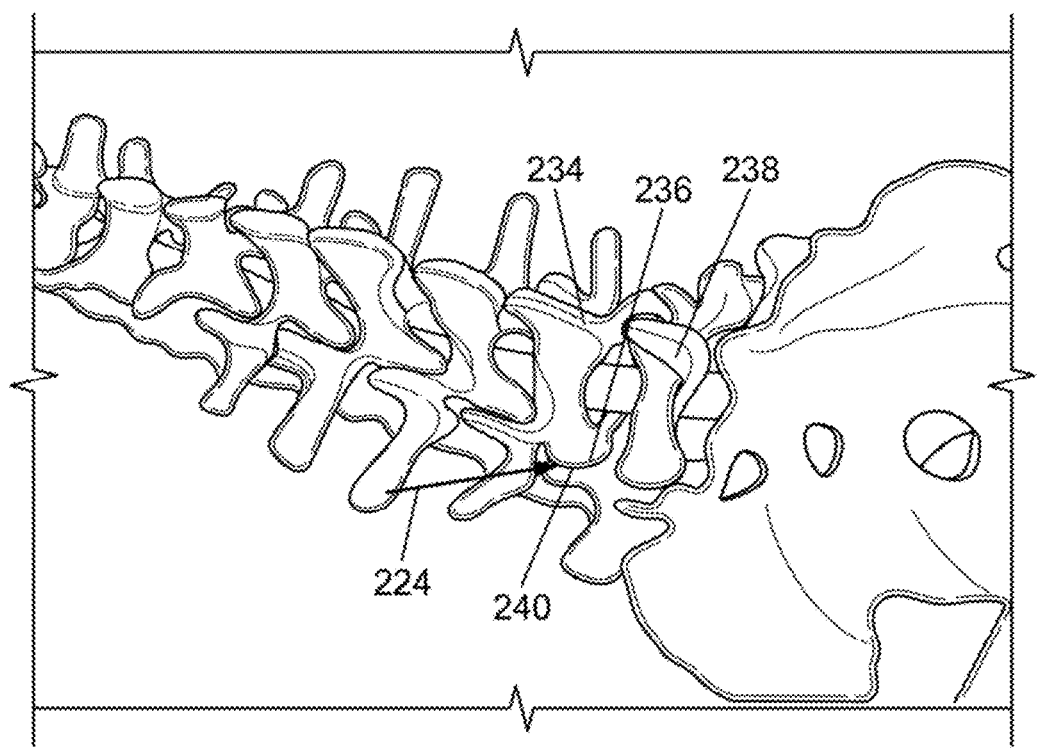
FIGS. 69 through 75 illustrate a variation of a method for using the device in a section of the spine.

FIG. 69 illustrates that a first vertebra 234 can have a first facet surface 236. A second vertebra 238 can be adjacent to the first vertebra 234. The second vertebra 238 can have a second facet surface 240 adjacent to the first facet surface 236. An implant pathway for the device can be substantially parallel with the first 236 and second facet surfaces 240. The device 2 can be pushed into the space between the first 236 and second facet surfaces 240.

Figure 70:
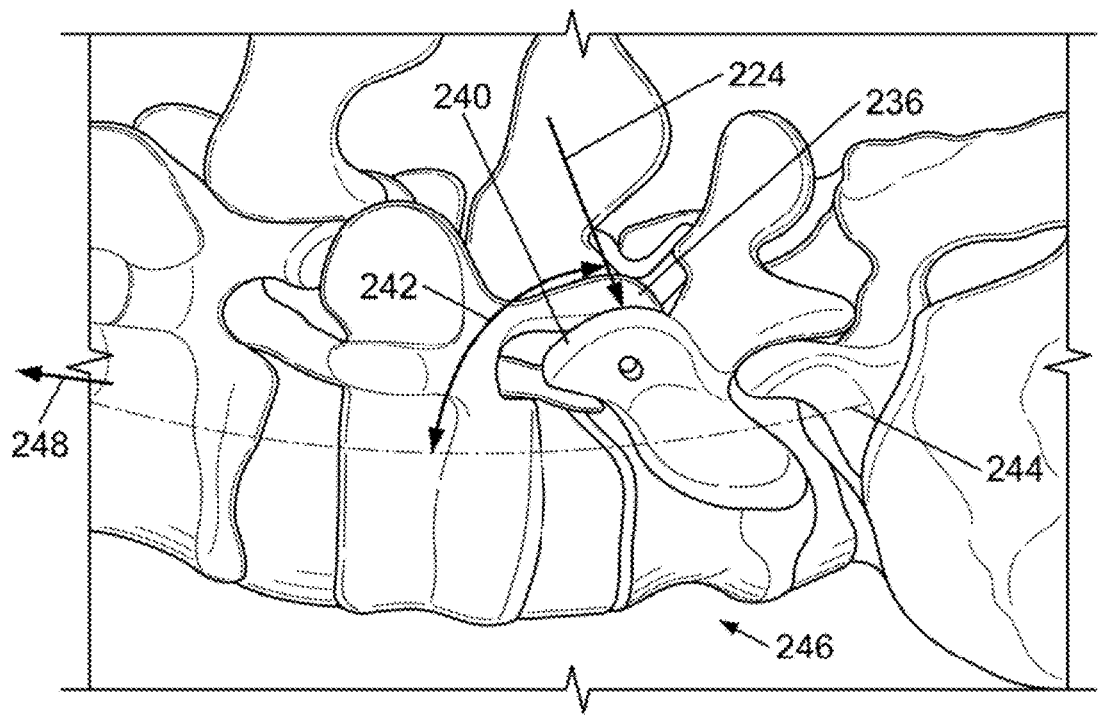

FIG. 70 illustrates that the implant angle can minimize the needle or punch from damaging the spinal cord 246. The spinal cord 246 is protected by the vertebral arch (lamina) just below the inferior articular process of the facet joint. The spine 246 can have a spinal longitudinal axis 244. The implant pathway 224 in the sagittal plane measured from the coronal side 248 of the longitudinal axis can have a sagittal implant pathway angle 242. The sagittal implant pathway angle 242 can be from about 40° to about 110°, for example about 60°.

Figure 71:
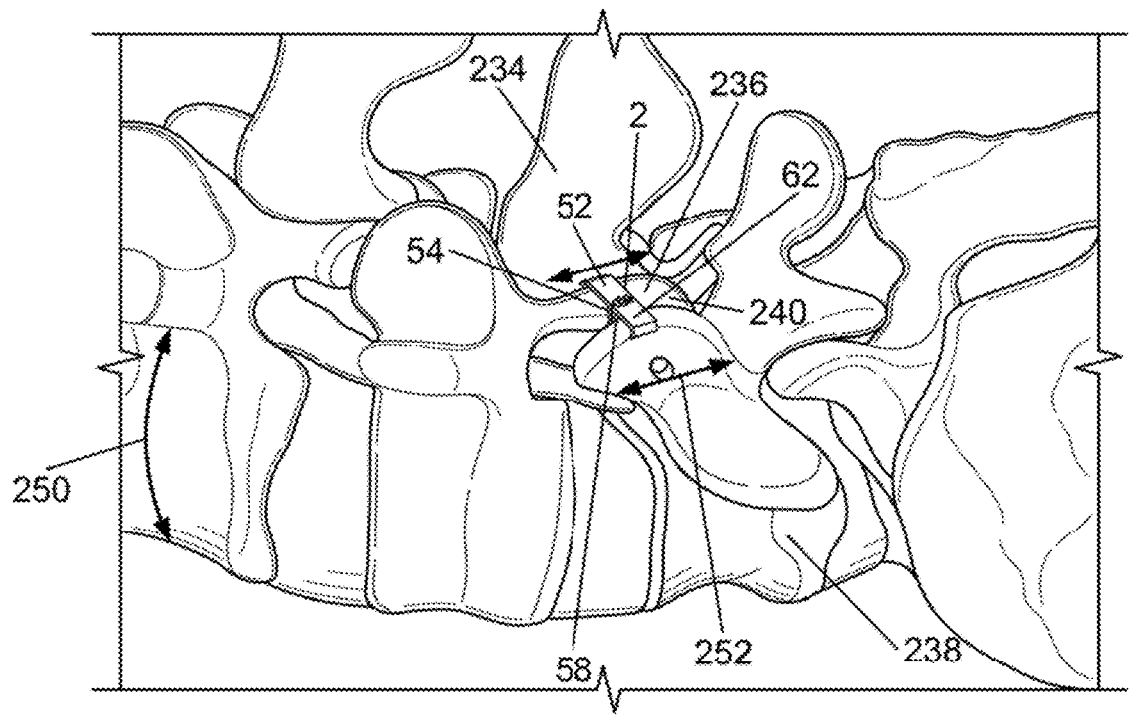

FIG. 71 illustrates that during spinal flexion or extension 250, as shown by arrows, the articular facet surfaces can experience shear forces 252 relative to each other. The device 2 can be oriented perpendicular to the shear motion, for example with the plane of the surface of the inner panels 54, 58 aligned with the shear forces 252.

Figure 72:
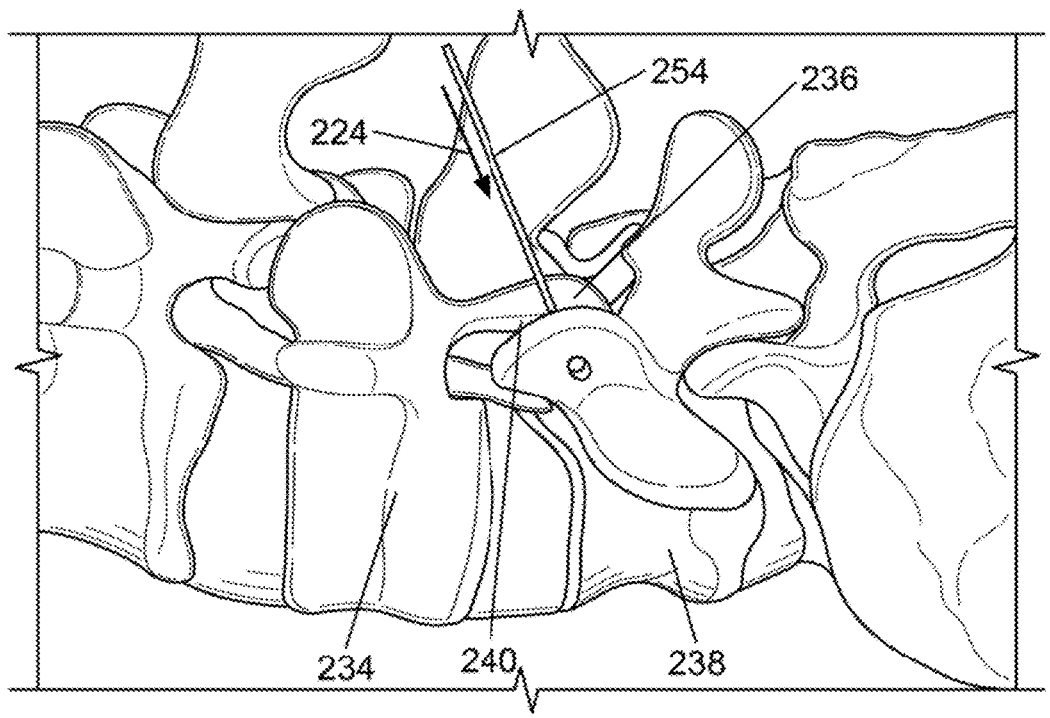

FIGS. 72 (and 78b, 78c and 78d) illustrates that a wire 254 can be inserted between the articular processes. The wire 254 can be a guidewire, lead, catheter, or combinations thereof. The wire 254 can be placed along the implant pathway 224. Deployment tools and/or the device 2 can be inserted along the wire 254. The wire 254 can be removed after positioning, expansion, or at any other time during deployment of the device 2 or deployment tools. The vertebral arch (lamina) can be stop the wire 254 (and device 2) insertion, for example, protecting the spinal cord and nerves.

Figure 73:
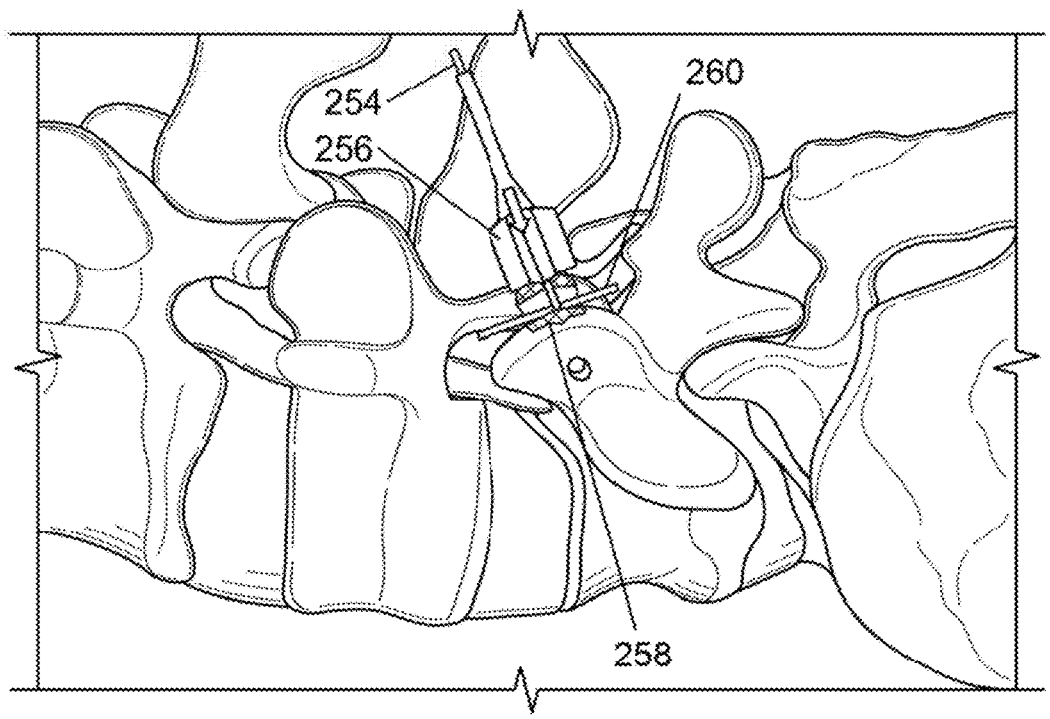

FIGS. 73 (and 78e, 78f and 78g) illustrate that a bone cavity 258 can be created. The bone shaping and removal can be performed with a drill 256 or other bone removal tool. The drill 256 can slide over and follow the wire 254 to the outer surface of the facet articular surface. The drill 256 can have a guide to orient the drill 256 with a cutting plane. The cutting plane can be the space between the inferior and superior articular process of the articular surfaces and sharp edges, for example the plain of the articular processes 260, as shown in FIG. 73. The drill 256 can cut, shape and remove tissue, such as bone and/or cartilage. The creation of the bone cavity 258 can create a bloody bone surface to aid in regrowth and fusing of the bones on which the cavity was created.

Figure 74:
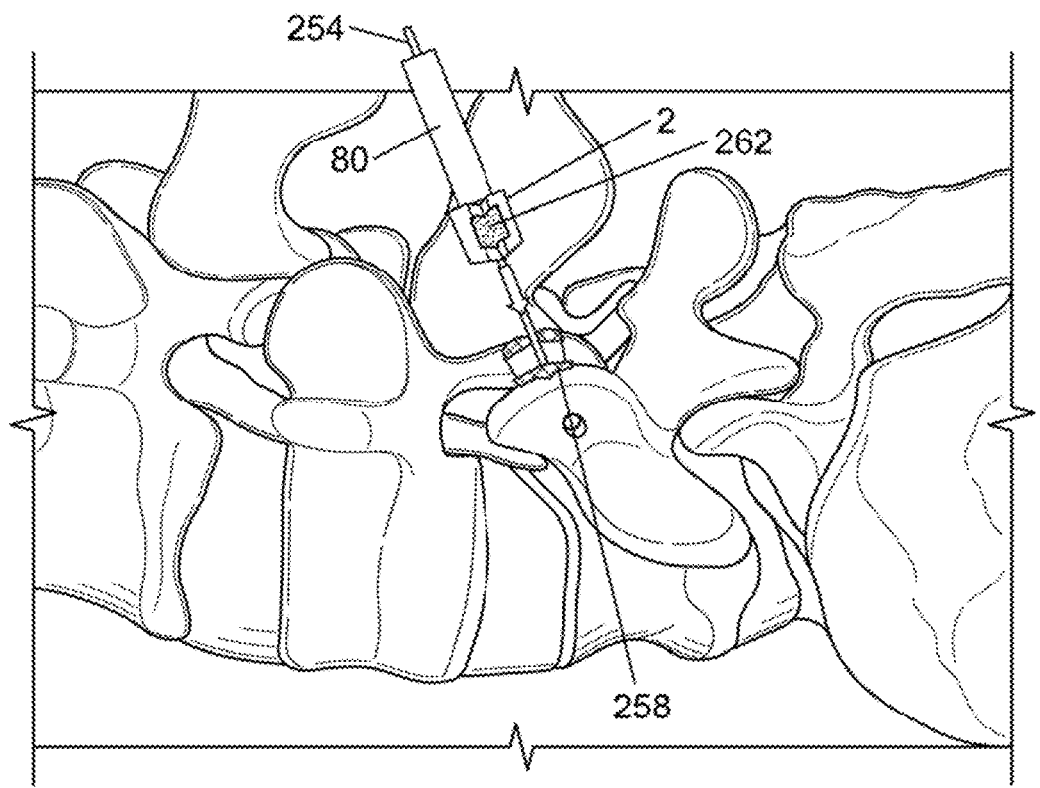

FIGS. 74 (and 76) illustrates that the device 2 can be removably attached to a delivery system or deployment tool

80. The deployment tool 80 can insert the device 2 into the target site. For example the deployment tool 80 can be pushed over the wire 254 as shown by arrow.

The device 2 can be positioned such that the first plate is against the first facet surface 236 and the second plate is against the second facet surface 240. For example, the inner panels can be against the facet surfaces 236, 240. Teeth or texturing on the panels and/or plates can be pressed against the facet surfaces 236, 240 and frictionally resist withdrawal from the deployed position. The stop panels and/or wing panels can abut bone and/or other tissue and stop insertion of the device 2 into the target site.

The opposed facet surfaces can compress against the device 2, for example, releasably fixing the device 2 in the facet joint.

When the device 2 is positioned as desired (e.g., into the drilled bone cavity and/or between unaltered surfaces forming the facet joint) and expanded and/or locked, the deployment tool 80 can then release the device 2. The device 2 can lock itself into place with outward expansion, wedging, or interference force when receiving a release force from the deployment tool 80 or otherwise.

Figure 75:
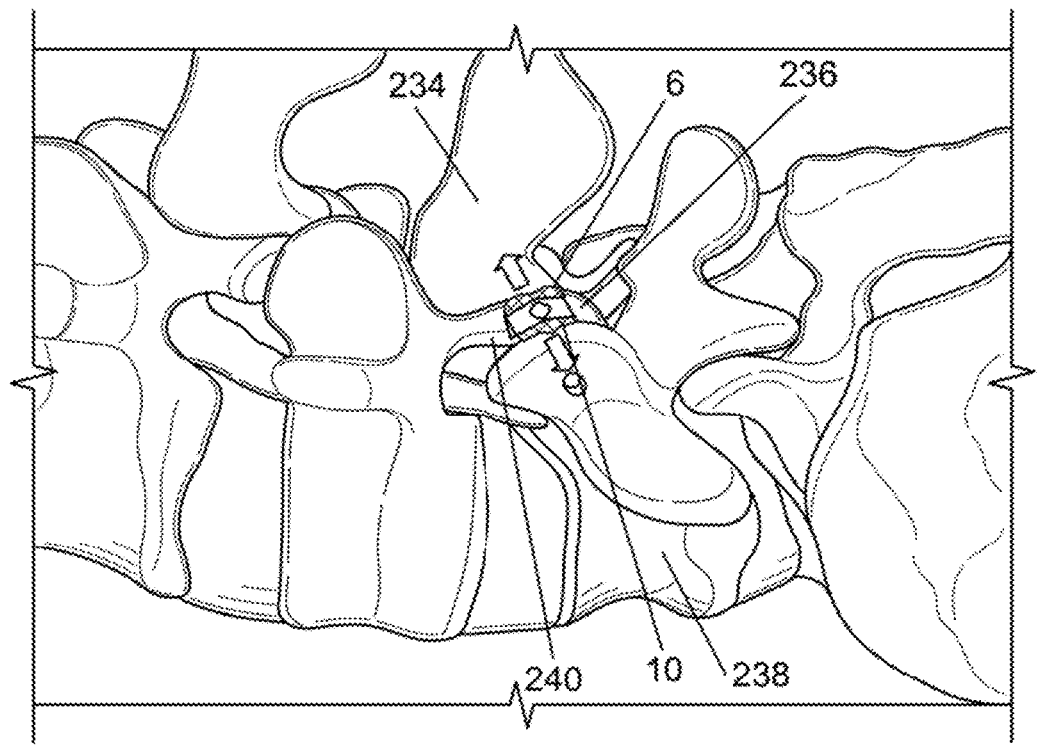

FIG. 75 illustrates that the device 2 can be expanded between the first and second articular process facet surfaces 236, 240. The device 2 can resist the shear forces shown in FIG. 71. The adjacent articular facet surfaces can regrow through and around the device 2 and fuse to each other (for example, with the cartilage removed).

Figure 76:
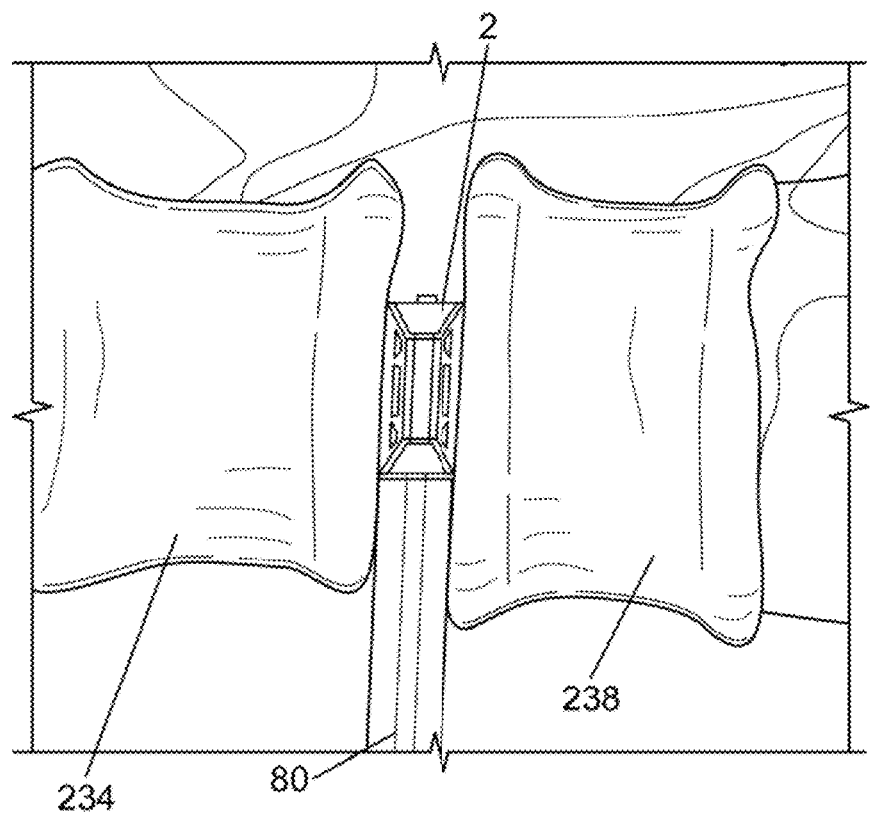
FIG. 76 illustrates a visualization of a variation of a method for deploying the device into the spine between adjacent vertebrae.

FIG. 76 illustrates the deployment tool 80 inserted to a target site in vivo between a first vertebra 234 and a second vertebra 238. For example, the device 2 can be placed at the target site after a partial or complete discectomy. When the device 2 is in a contracted configuration, the tool 80 can position the device 2 between a first vertebral body of the first vertebra 234 and a second vertebral body of the second vertebra 238. The device 2 can be inserted into the target site a direction substantially parallel to the surfaces of the vertebral body end plates. The device 2 can be placed between a first vertebral end plate of the first vertebral body and the adjacent second vertebral end plate of the second vertebral body. In this inter-vertebral location, the top plate of the device 2 can be in contact with or directly adjacent to the first vertebral end plate. The bottom plate of the device 2 can be in contact with or directly adjacent to the second vertebral end plate.

Figure 77A:
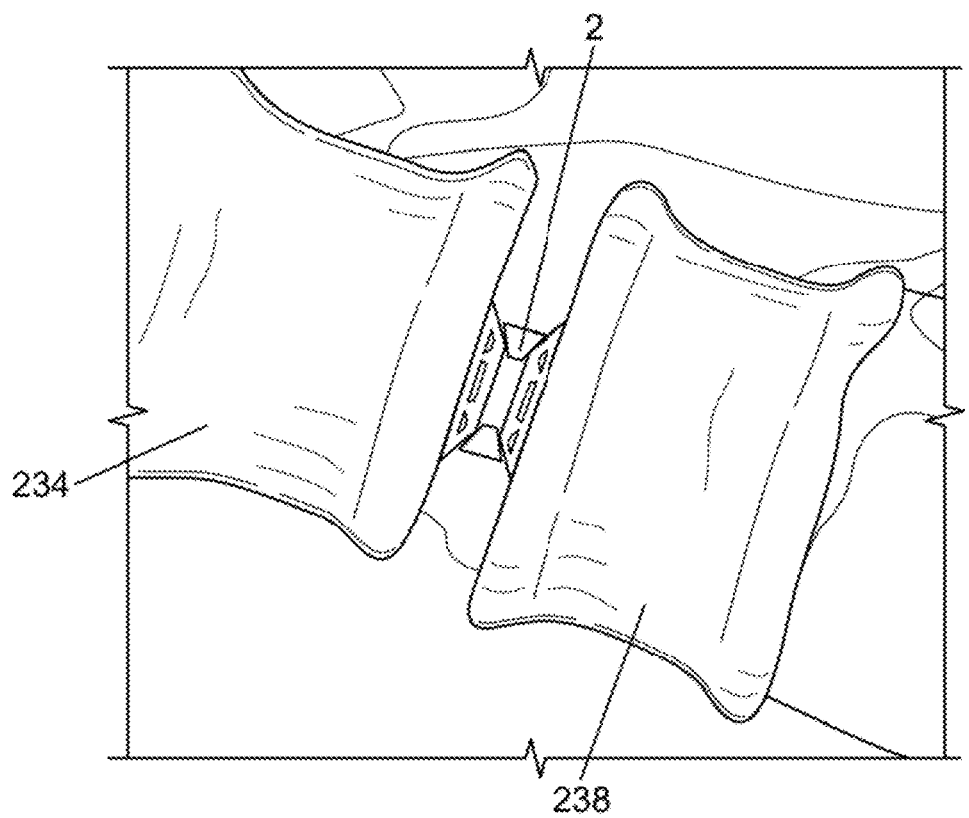
FIGS. 77a and 77b illustrate visualizations of variations of the device deployed into the spine between adjacent vertebrae.
Figure 77B:
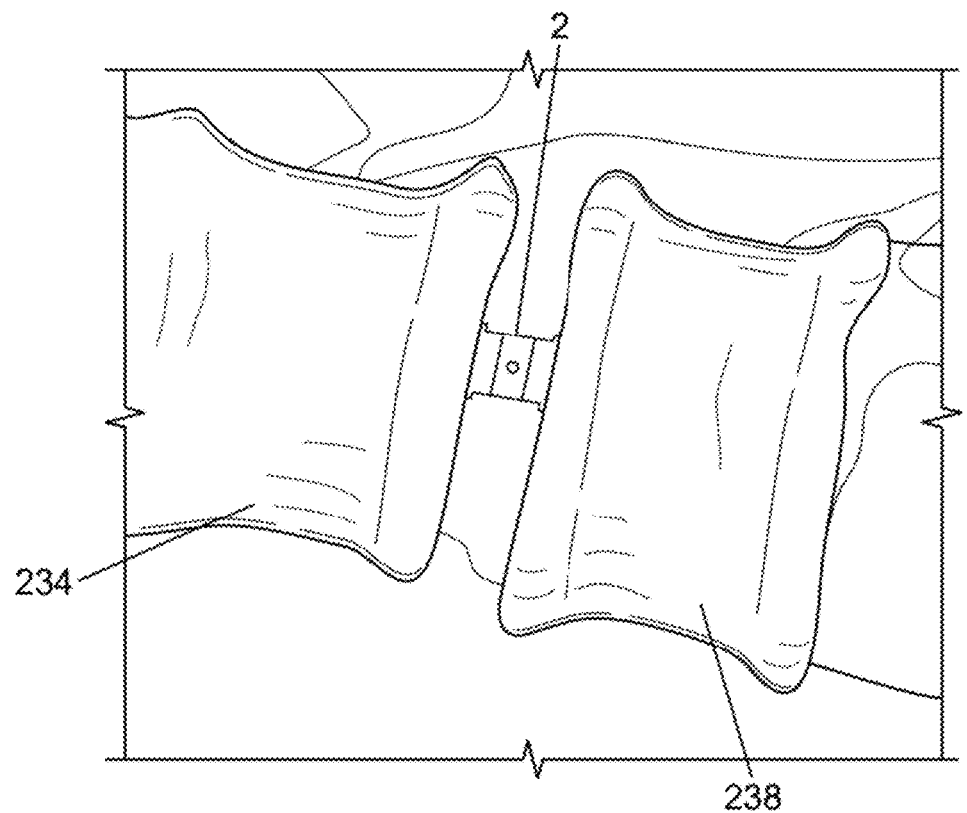

FIGS. 77a and 77b illustrate that the deployment tool 80 can radially expand the device 2 between the first vertebral end plate and the second vertebral end plate. The top plate can press against and/or embed into the first vertebral end plate. The bottom plate can press against and/or embed into the second vertebral end plate. The device can fuse the first vertebra 234 to the second vertebra 238.

The device 2 can be filled with a filled before or after radial expansion. Tissue ingrowth can occur into the top plate through the top ports, bottom plate through the bottom ports, and elsewhere through the device 2.

Figure 78A:
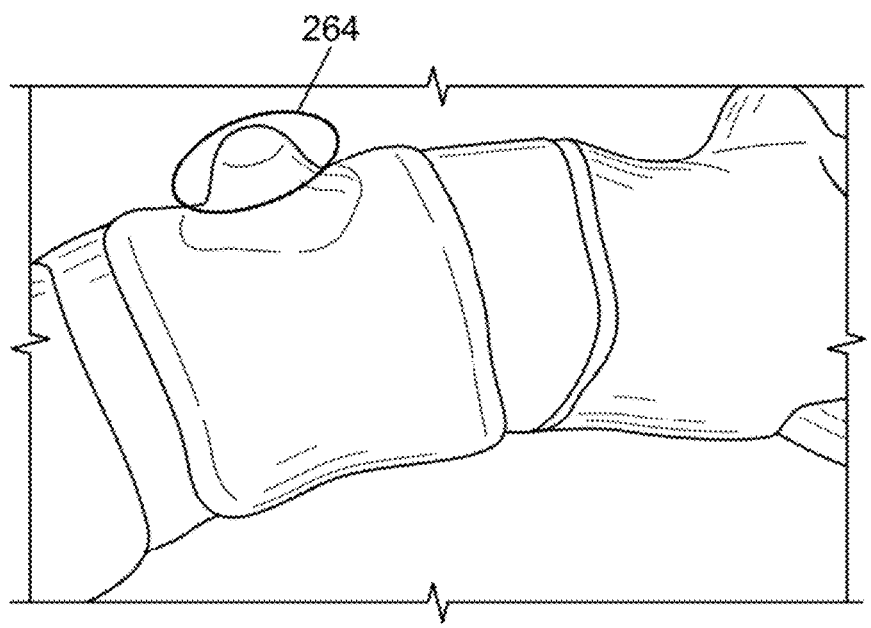
FIGS. 78a through 78g illustrate visualizations of a variation of a method for preparing the target site for the device.
Figure 78B:
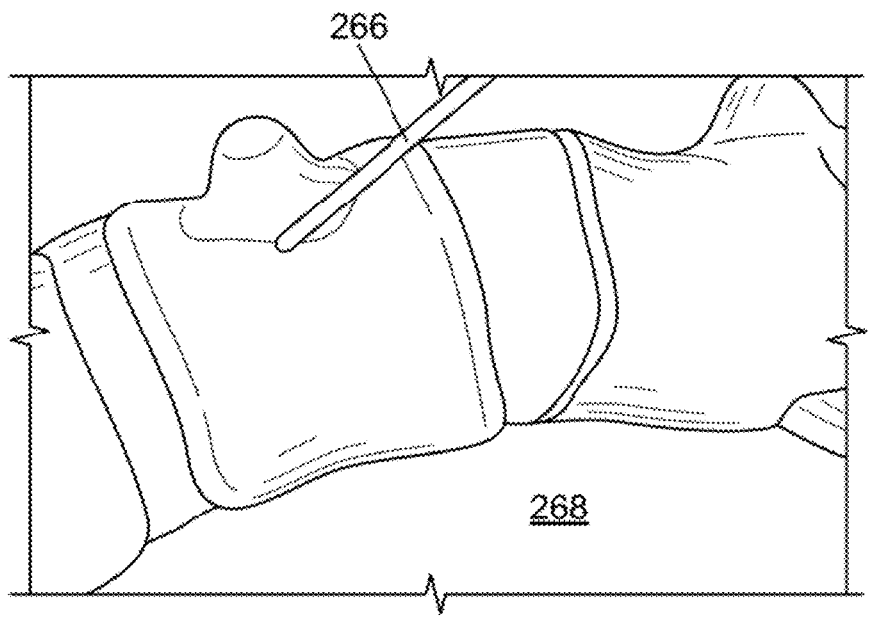
Figure 78C:
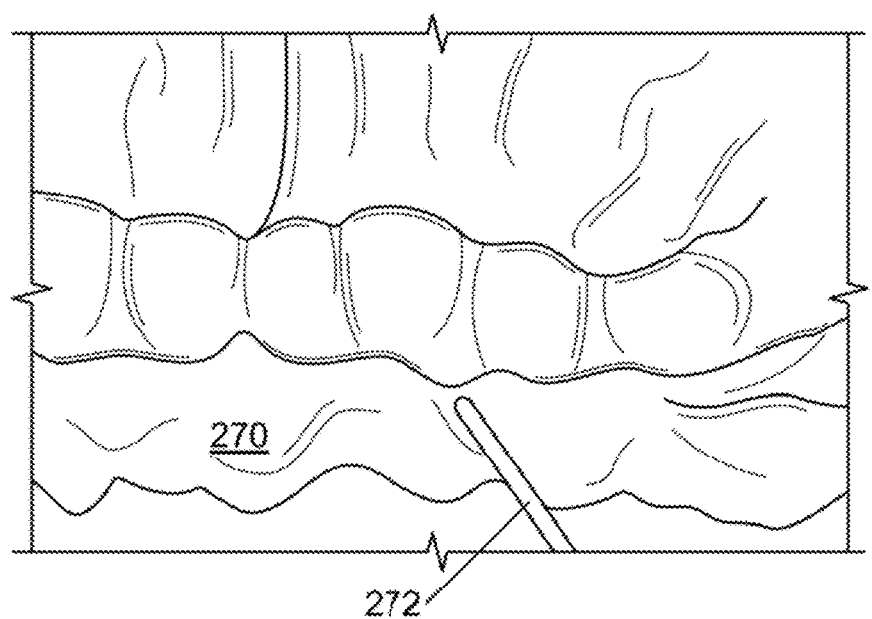

FIGS. 78a through 78g illustrate visualizations of a variation of a method for preparing the target site 264 for the device 2. FIG. 78a illustrate a visualization of the spine with the target site 264 identified, such as a facet joint. FIGS. 78b and 78c illustrates that a leader or wire 266, 272, such as a guidewire, can be inserted or otherwise deployed 270 into the target site 264, for example, the wire 266, 272 can be percutaneously inserted in a minimally invasive procedure. The wire 266, 272 can be inserted into the facet articular space 268, for example between the first facet surface and the adjacent second facet surface. The wire 266 can be anteriorly and/or posteriorly inserted, as shown in FIG. 78b. The 78c illustrates that the wire 272 can be laterally inserted.

Figure 78D:
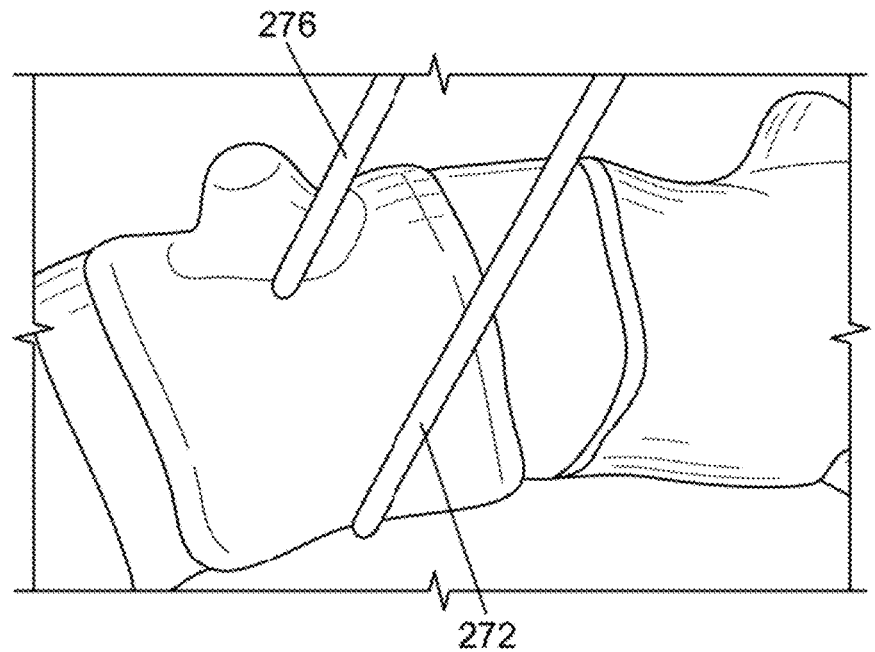

FIG. 78d illustrates that a first wire 276 can be inserted into the first facet joint. A second wire 272 can be inserted into the second facet joint. The first wire 276 can be inserted in an anteriorly/posteriorly direction, or a lateral direction. The second wire 272 can be inserted in an anteriorly/posteriorly direction, or a lateral direction.

Figure 78E:
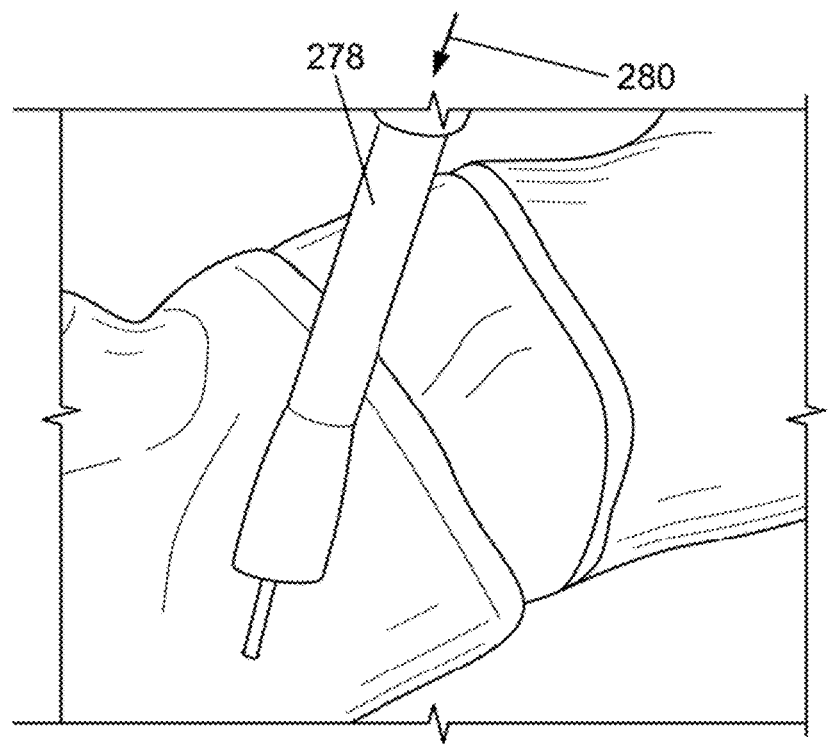
Figure 78F:
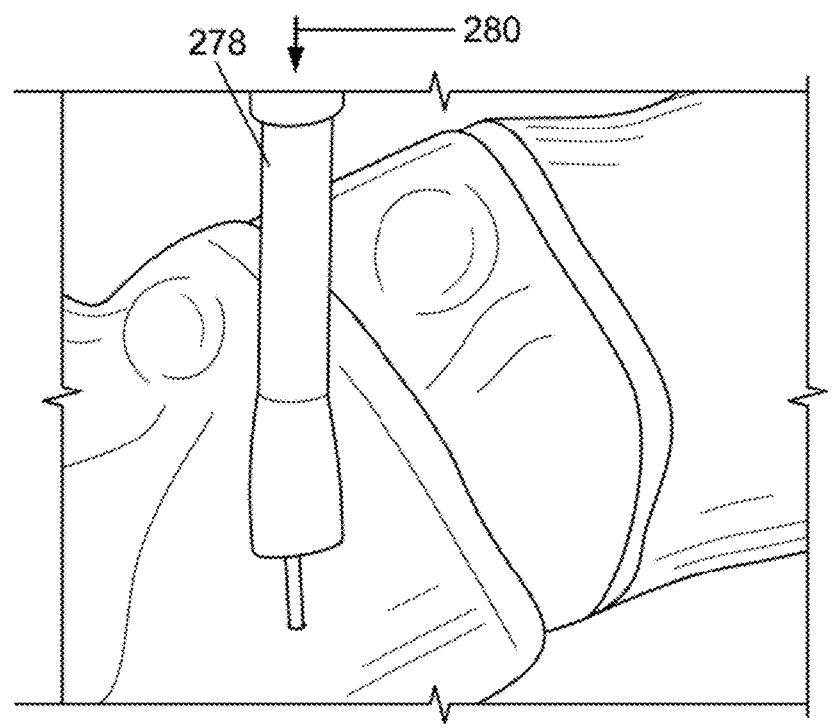
Figure 78G:
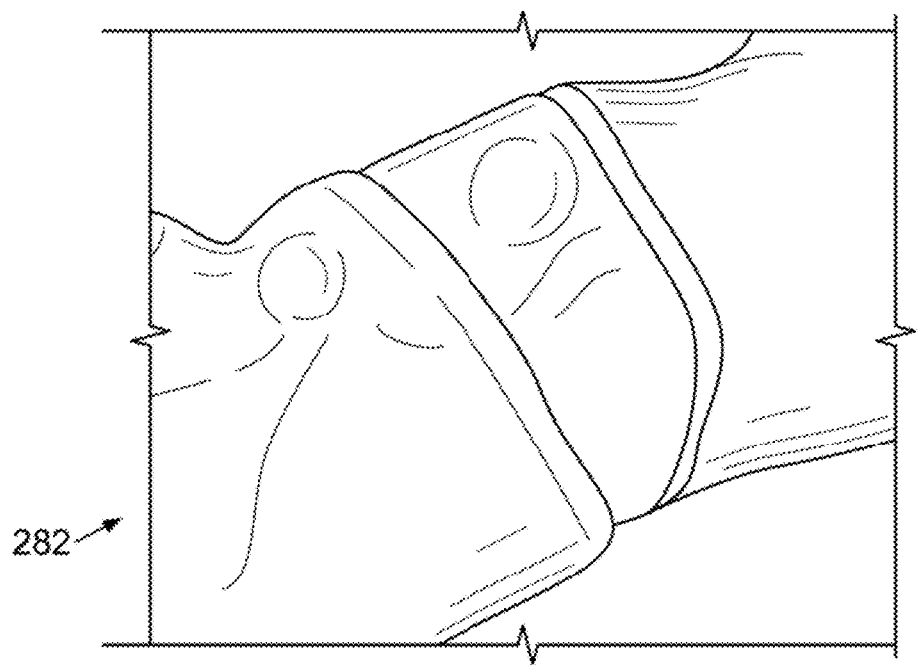

FIGS. 78e and 78f illustrate that the drill 278 can be inserted, as shown by arrow 280, over the wire to the target site, such as the pedicles. The drill 278 can then be used to drill away a portion of the bone 282, for example, creating a bone cavity as shown in FIG. 78g for insertion of the device.

Figure 79:
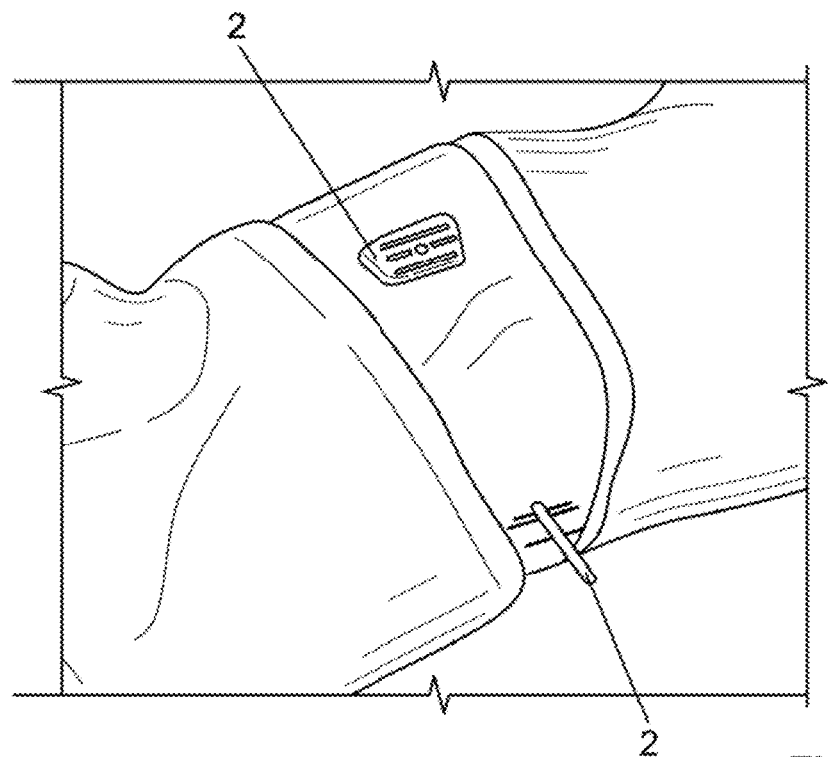
FIGS. 79 and 80 illustrate visualizations of variations of the device inserted in contracted configurations into the anterior/posterior and lateral bone cavity target sites of the spine, respectively, to provide facet fusion.
Figure 80:
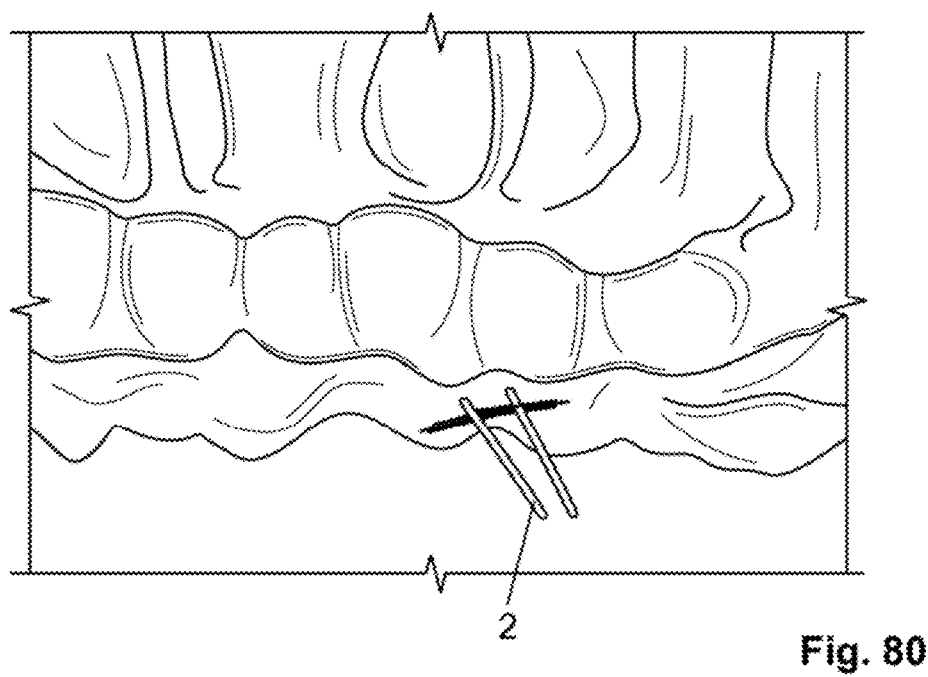

FIGS. 79 and 80 illustrate visualizations of variations of the device 2 inserted in contracted configurations into the anterior/posterior and lateral bone cavity target sites of the spine, respectively, to provide facet fusion. The devices 2 can have radiopaque and/or echogenic visualization markers, for example the markers can be along the top plate, bottom plate, and one or more panels of the plates. The deployment tool can also have one or more markers. The devices 2 can be inserted into multiple facet bone cavity target sites of the spine to provide facet fusion. A first device 2 can be inserted into a first facet joint and a second device 2 can be inserted into a second facet joint. The first and second devices 2 can be inserted bilaterally, for example both devices 2 can be inserted between the same first vertebra and second vertebra on opposite lateral sides.

Figure 81:
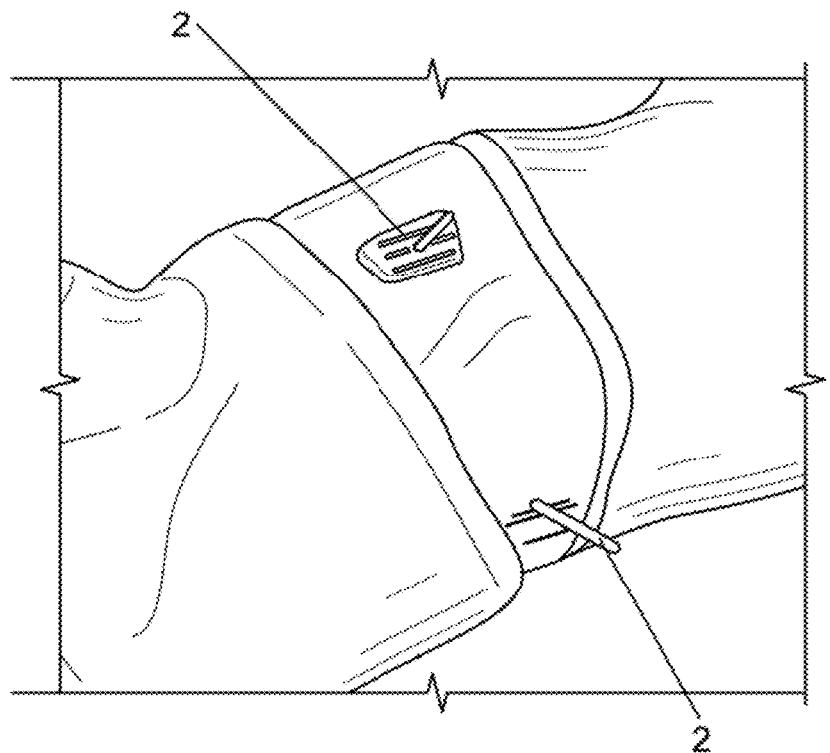
FIGS. 81 and 82 illustrate visualizations of variations of the device inserted in expanded configurations in the anterior/posterior and lateral bone cavity target sites of the spine, respectively, to provide facet fusion.
Figure 82:
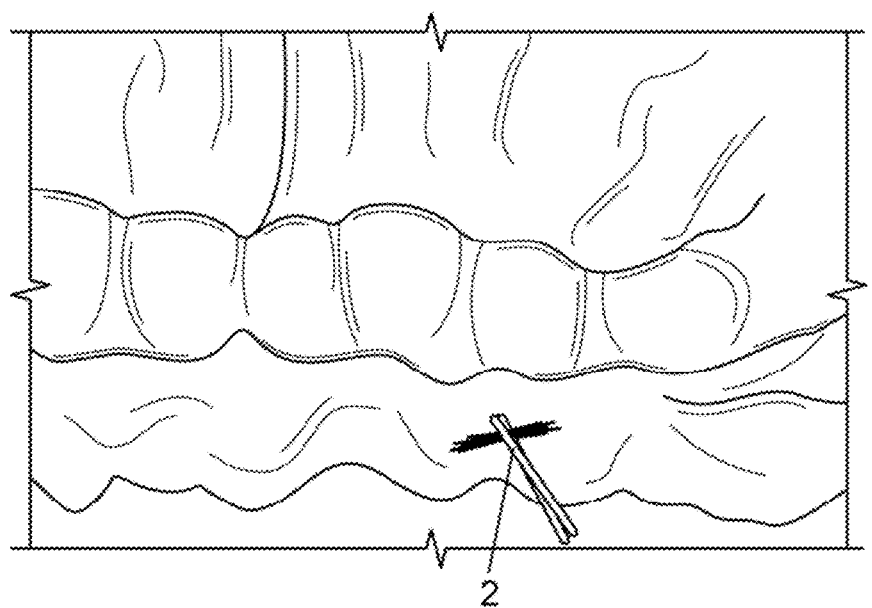

FIGS. 81 and 82 illustrate visualizations of variations of the devices 2 in expanded configurations in multiple facet bone cavity target sites of the spine to provide facet fusion. The first device 2 and second device 2 can be expanded in the first facet joint and the second device 2 can be inserted in the second facet joint.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The device can be made from substantially 100% PEEK, substantially 100% titanium or titanium alloy, or combinations thereof.

Any or all elements of the device and/or other devices or apparatuses described herein, can be, have, and/or be completely or partially coated with agents for cell ingrowth.

The device and/or elements of the device and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin E2 Synthesis in Abdominal Aortic Aneurysms, Circulation, Jul. 6, 1999, 48-54; Tambiah et al, Provocation of Experimental Aortic Inflammation Mediators and *Chlamydia Pneumoniae*, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

I claim:

1. An implantable orthopedic device, comprising:
   a first plate, having an outward-facing surface facing away from said device and an inward-facing surface opposed to said outward-facing surface, and having a plate longitudinal direction;
   a second plate opposed to the first plate; and
   a mechanism located between the first and second plates, the mechanism being capable of causing relative motion of the first and second plates toward or away from each other;
   wherein the first plate comprises, on the inward-facing surface of the first plate, a planar ramp surface, the planar ramp surface having a ramp direction inclined at an oblique ramp angle with respect to the plate longitudinal direction;
   wherein the oblique ramp angle with respect to the plate longitudinal direction is from 15 degrees to 75 degrees;
   wherein the planar ramp surface is bounded on respective sides by respective first and second grooves;
   wherein each groove defines a slot with an opening that faces toward a longitudinal center of the device;
   wherein the ramp surface and the first and second grooves in combination engage and capture a geometric feature of the mechanism while permitting sliding of the geometric feature relative to the planar ramp surface along the ramp direction;
   wherein an inward-facing surface of the second plate has a planar guide surface parallel to the plate longitudinal direction; and
   wherein the mechanism has a locking reception configuration at a proximal terminal end of the mechanism, the device further comprising a locking element configured to rotate with respect to the first plate and the second plate, and wherein the locking element is configured to fit into the locking reception configuration such that the locking reception configuration prevents rotation of the locking element.

2. The device of claim 1, wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region.

3. The device of claim 1, wherein each of the grooves has a pair of parallel sides and a planar connecting surface bottom between the two parallel sides.

4. The device of claim 1, wherein the first groove has a respective groove side not coincident with the planar ramp surface, and the second groove has a respective groove side not coincident with the planar ramp surface, and the respective groove sides are substantially coplanar with each other.

5. The device of claim 1, wherein one of the grooves has a groove side that is parallel to the planar ramp surface, and wherein one of the grooves has a groove side that is perpendicular to the planar ramp surface.

6. The device of claim 1, wherein the first plate comprises, on the inward-facing surface of the first plate, the planar ramp surface and an additional planar ramp surface.

7. An implantable orthopedic device, comprising:
a first plate, having an outward-facing surface facing away from said device and an inward-facing surface opposed to said outward-facing surface, and having a plate longitudinal direction;
a second plate opposed to the first plate; and
a mechanism located between the first and second plates, the mechanism being capable of causing relative motion of the first and second plates toward or away from each other;
wherein the first plate comprises, on the inward-facing surface of the first plate, a planar ramp surface, the planar ramp surface having a ramp direction inclined at an oblique ramp angle with respect to the plate longitudinal direction;
wherein the oblique ramp angle with respect to the plate longitudinal direction is from 15 degrees to 75 degrees;
wherein the planar ramp surface is bounded on respective sides by respective first and second grooves;
wherein each groove defines a slot with an opening that faces toward a longitudinal center of the device;
wherein the ramp surface and the first and second grooves in combination engage and capture a geometric feature of the mechanism while permitting sliding of the geometric feature relative to the planar ramp surface along the ramp direction;
wherein an inward-facing surface of the second plate has a planar guide surface parallel to the plate longitudinal direction; and
wherein the mechanism has a locking reception configuration at a proximal terminal end of the mechanism, the device further comprising a locking element configured to rotate with respect to the first plate and the second plate, and wherein the locking element is completely recessed within the locking reception configuration.

8. The device of claim 7, wherein the locking element is configured to fit into the locking reception configuration such that the locking reception configuration prevents rotation of the locking element.

9. An implantable orthopedic device, comprising:
a first plate, having an outward-facing surface facing away from said device and an inward-facing surface opposed to said outward-facing surface, and having a plate longitudinal direction;
a second plate opposed to the first plate; and
a mechanism located between the first and second plates, the mechanism being capable of causing relative motion of the first and second plates toward or away from each other;
wherein the first plate comprises, on the inward-facing surface of the first plate, a planar ramp surface, the planar ramp surface having a ramp direction inclined at an oblique ramp angle with respect to the plate longitudinal direction;
wherein the oblique ramp angle with respect to the plate longitudinal direction is from 15 degrees to 75 degrees;
wherein the planar ramp surface is bounded on respective sides by respective first and second grooves;
wherein each groove defines a slot with an opening that faces toward a longitudinal center of the device;
wherein the ramp surface and the first and second grooves in combination engage and capture a geometric feature of the mechanism while permitting sliding of the geometric feature relative to the planar ramp surface along the ramp direction;
wherein an inward-facing surface of the second plate has a planar guide surface parallel to the plate longitudinal direction; and
wherein the mechanism has a locking reception configuration at a proximal terminal end of the mechanism, the device further comprising a locking element configured to rotate with respect to the first plate and the second plate, and wherein the locking element is completely received by the locking reception configuration.

10. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other, wherein the mechanism has a locking reception configuration at a proximal terminal end of the mechanism, the device further comprising a locking element configured to rotate with respect to the first plate and the second plate;
wherein the first plate comprises, on the inward-facing surface of the first plate, a planar ramp surface, wherein the planar ramp surface is inclined at an oblique ramp angle with respect to the plate longitudinal direction and defining a ramp direction, and wherein the oblique ramp angle ramp angle is from 15 degrees to 75 degrees;
wherein the ramp surface the second plate in combination engage and capture the mechanism while permitting sliding of the mechanism relative to the planar ramp surface along the ramp direction; and
wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region.

11. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other, wherein the mechanism has a locking reception configuration at a proximal terminal end of the mechanism, the device further comprising a locking element configured to rotate with respect to the first plate and the second plate;
wherein the first plate comprises, on the inward-facing surface of the first plate, a planar ramp surface, wherein the planar ramp surface is inclined at an oblique ramp angle with respect to the plate longitudinal direction and defining a ramp direction, and wherein the oblique ramp angle ramp angle is from 15 degrees to 75 degrees;

wherein the ramp surface the second plate in combination engage and capture the mechanism while permitting sliding of the mechanism relative to the planar ramp surface along the ramp direction;

wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region; and wherein at least part of a radial perimeter of the locking element is surrounded by at least part of the remainder of the device prior to a locking by the locking element, and wherein the locking element is configured to fit into the locking reception configuration such that the locking reception configuration prevents rotation of the locking element.

12. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other, wherein the mechanism has a locking reception configuration at a proximal terminal end of the mechanism, the device further comprising a locking element configured to rotate with respect to the first plate and the second plate;
wherein the first plate comprises, on the inward-facing surface of the first plate, a planar ramp surface, wherein the planar ramp surface is inclined at an oblique ramp angle with respect to the plate longitudinal direction and defining a ramp direction, and wherein the oblique ramp angle ramp angle is from 15 degrees to 75 degrees;
wherein the ramp surface the second plate in combination engage and capture the mechanism while permitting sliding of the mechanism relative to the planar ramp surface along the ramp direction;
wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region; and
wherein at least part of a radial perimeter of the locking element is surrounded by at least part of the remainder of the device prior to a locking by the locking element, and wherein the locking element is completely recessed within the locking reception configuration.

13. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other, wherein the mechanism has a locking reception configuration at a proximal terminal end of the mechanism, the device further comprising a locking element configured to rotate with respect to the first plate and the second plate;
wherein the first plate comprises, on the inward-facing surface of the first plate, a planar ramp surface, wherein the planar ramp surface is inclined at an oblique ramp angle with respect to the plate longitudinal direction and defining a ramp direction, and wherein the oblique ramp angle ramp angle is from 15 degrees to 75 degrees;
wherein the ramp surface the second plate in combination engage and capture the mechanism while permitting sliding of the mechanism relative to the planar ramp surface along the ramp direction;
wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region; and
wherein at least part of a radial perimeter of the locking element is surrounded by at least part of the remainder of the device prior to a locking by the locking element, and wherein the locking element is completely received by the locking reception configuration.

14. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other;
wherein the first plate comprises, on the inward-facing surface of the first plate, a planar ramp surface bounded by two edges that are parallel to each other and generally coplanar with each other, the planar ramp surface having a ramp direction centerline midway between the two parallel edges, the centerline inclined at an oblique ramp angle with respect to the plate longitudinal direction and defining a ramp direction, and wherein the oblique ramp angle ramp angle is from 15 degrees to 75 degrees;
wherein, on each side, the planar ramp surface adjoins respective first side surfaces distinct from the planar ramp surface;
wherein the respective first side surfaces adjoin respective planar second surfaces distinct from the first side surfaces, the respective planar second surfaces being parallel to the planar ramp surface;
wherein the respective second surfaces adjoin respective third surfaces distinct from the second side surfaces;
wherein the planar ramp surface and the first side surfaces and the second surfaces and the third surfaces in combination engage and capture a geometric feature of the mechanism while permitting sliding of the geometric feature relative to the planar ramp surface along the ramp direction;

wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region;

wherein the second plate comprises, on an inward-facing surface of the second plate, a planar guide surface parallel to the plate longitudinal direction;

wherein the planar guide surface is bounded on respective sides by respective first and second grooves; and wherein the mechanism has a locking reception configuration at a proximal terminal end of the mechanism, the device further comprising a locking element configured to rotate with respect to the first plate and the second plate, wherein at least part of a radial perimeter of the locking element is surrounded by at least part of the remainder of the device prior to a locking by the locking element, and wherein the locking element is configured to fit into the locking reception configuration such that the locking reception configuration prevents rotation of the locking element.

15. The device of claim 14, wherein the respective first side surfaces are planar and parallel to each other.

16. The device of claim 14, wherein the respective third side surfaces are planar and parallel to each other.

17. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other;
wherein the first plate comprises, on the inward-facing surface of the first plate, a planar ramp surface bounded by two edges that are parallel to each other and generally coplanar with each other, the planar ramp surface having a ramp direction centerline midway between the two parallel edges, the centerline inclined at an oblique ramp angle with respect to the plate longitudinal direction and defining a ramp direction, and wherein the oblique ramp angle ramp angle is from 15 degrees to 75 degrees;
wherein, on each side, the planar ramp surface adjoins respective first side surfaces distinct from the planar ramp surface;
wherein the respective first side surfaces adjoin respective planar second surfaces distinct from the first side surfaces, the respective planar second surfaces being parallel to the planar ramp surface;
wherein the respective second surfaces adjoin respective third surfaces distinct from the second side surfaces;
wherein the planar ramp surface and the first side surfaces and the second surfaces and the third surfaces in combination engage and capture a geometric feature of the mechanism while permitting sliding of the geometric feature relative to the planar ramp surface along the ramp direction;
wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region;

wherein the second plate comprises, on an inward-facing surface of the second plate, a planar guide surface parallel to the plate longitudinal direction;

wherein the planar guide surface is bounded on respective sides by respective first and second grooves; and wherein the mechanism has a locking reception configuration at a proximal terminal end of the mechanism, the device further comprising a locking element configured to rotate with respect to the first plate and the second plate, wherein at least part of a radial perimeter of the locking element is surrounded by at least part of the remainder of the device prior to a locking by the locking element, and wherein the locking element is completely recessed within the locking reception configuration.

18. The device of claim 17, wherein the locking element is configured to fit into the locking reception configuration such that the locking reception configuration prevents rotation of the locking element.

19. An implantable orthopedic device, comprising:
a first plate, having an outward-facing surface facing away from the device and an inward-facing surface opposed to the outward-facing surface, and having a plate longitudinal direction;
a second plate opposed to the first plate; and
a mechanism located between the first and second plates, the mechanism being capable of causing relative motion of the first and second plates toward or away from each other;
wherein the first plate comprises, on the inward-facing surface of the first plate, a planar ramp surface bounded by two edges that are parallel to each other and generally coplanar with each other, the planar ramp surface having a ramp direction centerline midway between the two parallel edges, the centerline inclined at an oblique ramp angle with respect to the plate longitudinal direction and defining a ramp direction, and wherein the oblique ramp angle ramp angle is from 15 degrees to 75 degrees;
wherein, on each side, the planar ramp surface adjoins respective first side surfaces distinct from the planar ramp surface;
wherein the respective first side surfaces adjoin respective planar second surfaces distinct from the first side surfaces, the respective planar second surfaces being parallel to the planar ramp surface;
wherein the respective second surfaces adjoin respective third surfaces distinct from the second side surfaces;
wherein the planar ramp surface and the first side surfaces and the second surfaces and the third surfaces in combination engage and capture a geometric feature of the mechanism while permitting sliding of the geometric feature relative to the planar ramp surface along the ramp direction;
wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region;

wherein the second plate comprises, on an inward-facing surface of the second plate, a planar guide surface parallel to the plate longitudinal direction;

wherein the planar guide surface is bounded on respective sides by respective first and second grooves; and wherein the mechanism has a locking reception configuration at a proximal terminal end of the mechanism, the device further comprising a locking element configured to rotate with respect to the first plate and the second plate, wherein at least part of a radial perimeter of the locking element is surrounded by at least part of the remainder of the device prior to a locking by the locking element, and wherein the locking element is completely received by the locking reception configuration.

20. An implantable orthopedic device, comprising:

a first plate, having an outward-facing surface facing away from the device and an inward-facing surface opposed to the outward-facing surface, and having a plate longitudinal direction;

a second plate opposed to the first plate; and a mechanism located between the first and second plates, the mechanism being capable of causing relative motion of the first and second plates toward or away from each other;

wherein the first plate comprises, on the inward-facing surface of the first plate, a planar ramp surface bounded by two edges that are parallel to each other and generally coplanar with each other, the planar ramp surface having a ramp direction centerline midway between the two parallel edges, the centerline inclined at an oblique ramp angle with respect to the plate longitudinal direction and defining a ramp direction, and wherein the oblique ramp angle ramp angle is from 15 degrees to 75 degrees;

wherein, on each side, the planar ramp surface adjoins respective first side surfaces distinct from the planar ramp surface;

wherein the respective first side surfaces adjoin respective planar second surfaces distinct from the first side surfaces, the respective planar second surfaces being parallel to the planar ramp surface;

wherein the respective second surfaces adjoin respective third surfaces distinct from the second side surfaces;

wherein the planar ramp surface and the first side surfaces and the second surfaces and the third surfaces in combination engage and capture a geometric feature of the mechanism while permitting sliding of the geometric feature relative to the planar ramp surface along the ramp direction;

wherein the first plate has a centrally located first opening therethrough and the second plate has a centrally located second opening therethrough and wherein a window region of space connecting the first opening and the second opening is not crossed by any object extending within the window region continuously from a proximal edge of the window region to a distal edge of the window region;

wherein the second plate comprises, on an inward-facing surface of the second plate, a planar guide surface parallel to the plate longitudinal direction;

wherein the planar guide surface is bounded on respective sides by respective first and second grooves; and wherein the mechanism has a locking reception configuration at a proximal terminal end of the mechanism, the device further comprising a locking element configured to rotate with respect to the first plate and the second plate, wherein at least part of a radial perimeter of the locking element is surrounded by at least part of the remainder of the device prior to a locking by the locking element, and wherein the outer surface of the locking element is smooth.

* * * * *